United States Patent [19]
Arendsen et al.

[11] Patent Number: 5,831,115
[45] Date of Patent: Nov. 3, 1998

[54] INHIBITORS OF SQUALENE SYNTHASE AND PROTEIN FARNESYLTRANSFERASE

[75] Inventors: David L Arendsen, Libertyville, Ill.; William R. Baker, Bellevue, Wash.; Stephen A Fakhoury, Mundelein; Anthony K. L. Fung, Gurnee, both of Ill.; David S. Garvey, Dover, Mass.; William J. McClellan, Waukegan, Ill.; Stephen J. O'Connor, Wilmette, Ill.; Rajnandan N. Prasad, Vernon Hills, Ill.; Todd W. Rockway, Grayslake, Ill.; Saul H. Rosenberg, Grayslake, Ill.; Herman H. Stein, Highland Park, Ill.; Wang Shen, Skokie, Ill.; David M. Stout, Mettawa, Ill.; Gerard M. Sullivan, Round Lake Beach, Ill.; David J. Augeri, Kenosha, Wis.

[73] Assignee: Abbott Laboratories, Abbott Park, Ill.

[21] Appl. No.: 626,859

[22] Filed: Apr. 11, 1996

Related U.S. Application Data

[63] Continuation-in-part of Ser. No. 564,524, Nov. 29, 1995, abandoned, which is a continuation-in-part of Ser. No. 426,553, Apr. 21, 1995, abandoned, and a continuation-in-part of Ser. No. 428,357, Apr. 21, 1995, abandoned.

[51] Int. Cl.$^6$ .......................... C07C 229/00; A01N 37/10
[52] U.S. Cl. ........................... 560/41; 514/533; 514/563; 562/450; 562/451; 562/455
[58] Field of Search ................. 560/41; 562/450, 562/451, 455; 514/533, 563

[56] References Cited

FOREIGN PATENT DOCUMENTS

| 12572 | 5/1995 | WIPO . |
| 9512572 | 5/1995 | WIPO .......................... C07C 233/60 |

OTHER PUBLICATIONS

Ortiz De Mantellano, P. R. et al., "Prenyl Substituted Cyclobutanones as Squalene Synthetase Inhibitors", Tetrahedron Letters, No. 46, pp. 4115–4118, printed in Great Britain by Pergamon Press, 1976.

*Primary Examiner*—Paul J. Killos
*Attorney, Agent, or Firm*—Gregory W. Steele; Steven R. Crowley

[57] ABSTRACT

The present invention provides a compound of the formula

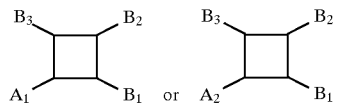

or a pharmaceutically acceptable salt thereof, which are useful for inhibiting protein farnesyltransferase and the farnesylation of the oncogene protein Ras or inhibiting de novo squalene production resulting in the inhibition of cholesterol biosynthesis, processes for the preparation of the compounds of the invention in addition to intermediates useful in these processes, a pharmaceutical composition, and to methods of using such compounds.

35 Claims, No Drawings

INHIBITORS OF SQUALENE SYNTHASE AND PROTEIN FARNESYLTRANSFERASE

This application is a continuation-in-part of U.S. patent application Ser. No. 08/564,524, filed Nov. 25, 1995, abandoned which is a continuation-in-part of U.S. patent application Ser. No. 08/426,553, filed Apr. 21, 1995 abandoned and is also a continuation-in-part of U.S. patent application Ser. No. 08/428,357 filed Apr. 21, 1995, abandoned.

TECHNICAL FIELD

The present invention relates to new cyclobutane mono-, di- or tri-carboxylic acid compounds which are useful for inhibiting de novo squalene production resulting in the inhibition of cholesterol biosynthesis and for inhibiting protein farnesyltransferase and the farnesylation of the oncogene protein Ras, compositions containing such compounds and to methods of using such compounds.

BACKGROUND OF THE INVENTION

Squalene synthase is a microsomal enzyme which catalyzes the reductive dimerization of two molecules of farnesyl pyrophosphate (FPP) in the presence of nicotinamide adenine dinucleotide phosphate, reduced form, (NADPH) to form squalene (Poulter, C. D., Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. Thus inhibitors of squalene synthase cause inhibition of cholesterol biosynthesis and thus act as a hypocholesterolemic agents. Thus squalene synthase inhibitors are useful for the treatment and prevention of hyperlipidemia or atherosclerosis or other disorders resulting from an excess of cholesterol.

Inhibition of squalene synthase also results in the inhibition of fungal growth.

Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase and, thereby, of farnesylation of the Ras protein, blocks the ability of transformed cells to proliferate.

Activation of Ras also partially mediates smooth muscle cell proliferation (Circulation, I-3: 88 (1993)). Inhibition of protein farnesyltransferase and, thereby, of farnesylation of the Ras protein, will also aid in the treatment or prevention of restenosis.

DISCLOSURE OF THE INVENTION

In accordance with the present invention there are provided cyclobutane compounds of formula (I) or (II):

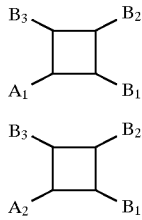

wherein $A_1$ is —C(O)NR$_1$R$_2$ wherein
$R_1$ is selected from the group consisting of (i) hydrogen, (ii) loweralkyl, (iii) alkenyl, (iv) alkynyl, (v) aryl, (vi) arylalkyl, and (vii) heterocyclicalkyl, and $R_2$ is

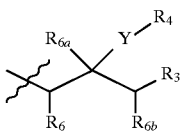

wherein $R_3$ is aryl, aryl substituted with aryl, aryl substituted with heterocyclic or heterocyclic; $R_4$ is aryl, aryl substituted with aryl, aryl substituted with heterocyclic or heterocyclic; $R_6$, $R_{6a}$ and $R_{6b}$ are independently selected from the group consisting of hydrogen and loweralkyl; and Y is a single covalent bond, —CH$_2$—, —CH$_2$CH$_2$—, —CH=CH—, —O—C(O)—, —C(O)—O—, —O—CH$_2$—, —CH$_2$—O—, —S—CH$_2$— or —CH$_2$—S—;

$A_2$ is
(1) —X—T—G
wherein T is selected from the group consisting of
  a) a covalent bond,
  b) —C(O)—,
  c) —C(S)— and
  d) —S(O)$_2$—,
X is selected from the group consisting of
  a) a covalent bond,
  b) —CH$_2$—,
  c) —O—,
  d) —S— and
  e) —N(R$_a$)— wherein R$_a$ is hydrogen, loweralkyl, cycloalkyl, cycloalkylalkyl or arylalkyl,
and G is selected from the group consisting of
  a) R$_{42}$,
  b) —N(R$_{41}$)(R$_{42}$)
wherein R$_{41}$ is selected from the group consisting of
  (i) —CH(R$_d$)C(O)OR$_e$ wherein R$_d$ is selected from the group consisting of loweralkyl, cycloalkyl, cycloalkylalkyl, alkoxyalkyl, thioalkoxyalkyl, hydroxyalkyl, aminoalkyl, carboxyalkyl, alkoxycarbonylalkyl, arylalkyl and alkylsulfonylalkyl and R$_e$ is selected from the group consisting of hydrogen and carboxy-protecting group,
  (ii) aryl,
  (iii) arylalkyl,
  (iv) heterocyclic,
  (v) (heterocyclic)alkyl,
  (vi) cycloalkylalkyl and
  (vii) aryl, heterocyclic, arylalkyl or (heterocyclic)alkyl wherein the aryl group, the aryl part of the arylalkyl group, the heterocyclic group or the heterocyclic part of the (heterocyclic) alkyl group is substituted with one or two substituents —W—R$_{43}$ wherein at each occurrence W is independently selected from the group consisting of
    (a) a covalent bond, (b) —C(O)—, (c) —CH$_2$—, (d) —O—, (e) —S(O)$_p$— wherein p is 0, 1 or 2, (f) —N(R$_c$)— wherein R$_c$ is hydrogen or loweralkyl, (g) —CH$_2$O—, (h) —CH$_2$S(O)$_p$— wherein p is 0, 1 or 2 and (i) —CH$_2$N(R$_c$)— wherein R$_c$ is hydrogen or loweralkyl and
at each occurrence R$_{43}$ is independently selected from the group consisting of
  (a) aryl, (b) arylalkyl,
  (c) cycloalkyl, (d) cycloalkylalkyl, (e) heterocyclic and (f) (heterocyclic)alkyl,
and $R_{42}$ is selected from the group consisting of
(i) aryl,
(ii) arylalkyl,
(iii) alkenyl,
(iv) alkynyl,
(v) arylalkenyl,
(vi) arylalkynyl,
(vii) (heterocyclic)alkyl,
(viii) aryloxyalkyl,
(ix) aryloxyalkenyl,
(x) arylal koxyalkenyl,
(xi) arylalkyl wherein the alkyl group is substituted with (a) —$OR_{10}$ wherein $R_{10}$ is hydrogen or alkanoyl or (b) —$C(O)OR_h$ wherein $R_h$ is hydrogen or a carboxy-protecting group,
(xii) aroyloxyalkyl, and
(xiii) aryl, arylalkyl or (heterocyclic)alkyl wherein the aryl group, the the aryl part of the arylalkyl group or the heterocyclic part of the (heterocyclic)alkyl group is substituted with one or two substituents —W'—$R_{44}$ wherein at each occurrence W' is independently selected from the group consisting of
(a) a covalent bond, (b) —C(O)—, (c) —$CH_2$—, (d) —O—, (e) —$S(O)_m$— wherein m is 0, 1 or 2, (f) —$N(R_b)$— wherein $R_b$ is hydrogen or loweralkyl, (g) —$CH_2O$—, (h) —$CH_2S(O)_m$— wherein m is 0, 1 or 2 and
(i) —$CH_2N(R_b)$— wherein $R_b$ is hydrogen or loweralkyl and at each occurrence $R_{44}$ is independently selected from the group consisting of (a) aryl, (b) arylalkyl, (c) cycloalkyl, (d) cycloalkylalkyl, (e) heterocyclic and (f) (heterocyclic)alkyl, and
c) —$NHR_{42a}$ or —$OR_{42a}$
wherein $R_{42a}$ is selected from the group consisting of
(i) arylalkyl and
(ii) heterocyclicalkyl,
wherein the alkyl part of the arylalkyl group or the heterocyclicalkyl group is substituted with an arylalkyl group and wherein the aryl part of the arylalkyl group or the heterocyclic part of the heterocyclicalkyl group is substituted with one or two substituents —W"—$R_{45}$ wherein at each occurrence W" is independently selected from the group consisting of (a) a covalent bond, (b) —C(O)—, (c) —$CH_2$—, (d) —O—, (e) —$S(O)_{m'}$— wherein m' is 0, 1 or 2, (f) —$N(R_{b'})$— wherein $R_{b'}$ is hydrogen or loweralkyl, (g) —$CH_2O$—, (h) —$CH_2S(O)_{m'}$ wherein m' is 0, 1 or 2 and (i) —$CH_2N(R_{b'})$— wherein $R_{b'}$ is hydrogen or loweralkyl and at each occurrence $R_{45}$ is independently selected from the group consisting of (a) aryl, (b) arylalkyl, (c) cycloalkyl, (d) cycloalkylalkyl, (e) heterocyclic and (f) (heterocyclic)alkyl;
(2) —$C(O)R_{42a}$ wherein at each occurrence $R_{42a}$ is independently defined as above;
(3) —$CH(OH)R_{42a}$ wherein at-each occurrence $R_{42a}$ is independently defined as above;
(4) —$CH=C(R_{42b})(R_{42c})$ wherein at each occurrence $R_{42b}$ is independently selected from arylalkyl and at each occurrence $R_{42c}$ is independently selected from the group consisting of aryl and heterocyclic wherein the aryl or heterocyclic ring is subsubstituted with —W"—$R_{45}$ wherein at each occurrence W" and $R_{45}$ are independently defined as above; or
(5) —C(O)—$CH(R_{42a})CH(R_{42d})C(O)OR_g$ wherein at each occurrence $R_{42a}$ is independently defined as above, at each occurrence $R_{42d}$ is independently selected from aryl and at each occurrence $R_g$ is independently selected from the group consisting of hydrogen and a carboxy-protecting group;

and $B_1$, $B_2$ and $B_3$ are independently selected from the group consisting of
(1) hydrogen,
(2) —Q—D wherein at each occurrence D is independently selected from the group consisting of
(i) —$C(O)R_{46}$ wherein at each occurrence $R_{46}$ is independently selected from the group consisting of (a) —$OR_{46a}$ wherein at each occurrence $R_{46a}$ is independently selected from the group consisting of hydrogen, a carboxy-protecting group and arylalkyl wherein the alkyl part is substituted with an aryl group, (b) an alpha-amino acid or a beta-amino acid which is bonded via the alpha- or beta-amino group and (c) a di-, tri- or tetrapeptide which is bonded via the amino terminal amino group,
(ii) —C(O)H,
(iii) —$CH_2OH$,
(iv) —$C(O)CF_3$,
(v) —$CH(OH)CF_3$,
(vi) —$C(OH)(CF_3)_2$,
(vii) —$C(O)NH_2$,
(viii) —C(O)NHOH,
(ix) —CH(=NOH),
(x) —$S(O)_2NH_2$,
(xi) —$NHS(O)_2CH_3$ or —$NHS(O)_2CF_3$,
(xii) 5-tetrazolyl,

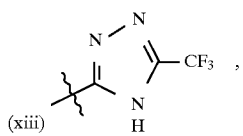
(xiii)

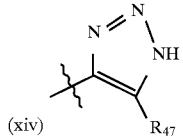
(xiv)

wherein $R_{47}$ is —CN, —$NO_2$, or —$CO_2R_{48}$ wherein $R_{48}$ is hydrogen, aryl or loweralkyl,

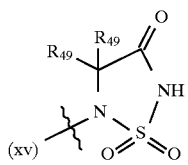
(xv)

wherein at each occurrence $R_{49}$ is independently selected from the group consisting of hydrogen and loweralkyl,

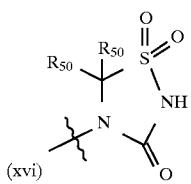
(xvi)

wherein at each occurrence R₅₀ is independently selected from the group consisting of hydrogen and loweralkyl,

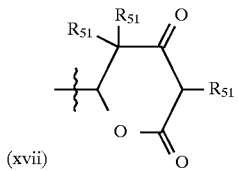
(xvii)

wherein at each occurrence R₅₁ is independently selected from the group consisting of hydrogen, loweralkyl, alkenyl, alkoxyalkyl and benzyl,

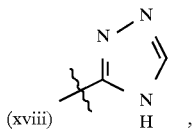
(xviii)

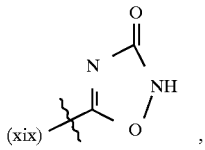
(xix)

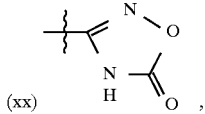
(xx)

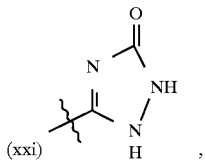
(xxi)

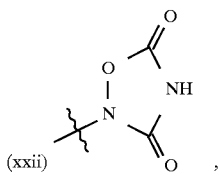
(xxii)

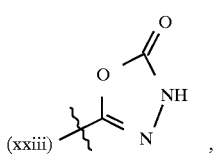
(xxiii)

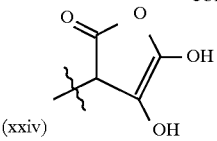
(xxiv)

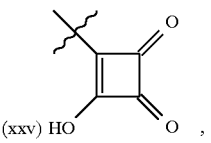
(xxv)

and
wherein at each occurrence Q is independently selected from the group consisting of (i) a covalent bond, (ii) —OCH₂—, (iii) alkylene, (iv) alkenylene, (v) —C(O)NH, (vi) —NHC(O)NH—, (vii) —CH(OH)— and (viii) —NHC(O)(CH₂)$_r$— wherein r is 0 to 4;

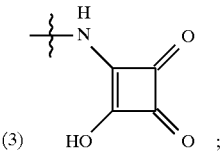
(3)

(4) —CH₂—N(OH)—C(O)—R₅₂ wherein R₅₂ is hydrogen, methyl or trifluoromethyl; and
(5) —C(O)—NH—S(O)₂—R₅₃ wherein R₅₃ is aryl, heterocyclic, arylalkyl, (heterocyclic)alkyl, C₃–C₇-cycloalkyl, C₁–C₈-alkyl or perfluoro-C₁–C₄-alkyl;
with the proviso that only one or two of B₁, B₂ and B₃ can be hydrogen; or a pharmaceutically acceptable salt thereof.

One embodiment of the present invention is a cyclobutane compound of formula (I):

$$\begin{array}{c} B_3 \quad\quad B_2 \\ \square \\ A_1 \quad\quad B_1 \end{array} \quad (I)$$

wherein
A₁ is —C(O)NR₁R₂ wherein
R₁ is selected from the group consisting of (i) hydrogen, (ii) loweralkyl, (iii) alkenyl, (iv) alkynyl, (v) aryl, (vi) arylalkyl, and (vii) heterocyclicalkyl, and
R₂ is

[structure with R₆ₐ, Y, R₄, R₃, R₆, R₆ᵦ]

wherein R₃ is aryl, aryl substituted with aryl, aryl substituted with heterocyclic or heterocyclic; R₄ is aryl, aryl substituted with aryl, aryl substituted with heterocyclic or heterocyclic; R₆, R₆ₐ and R₆ᵦ are independently selected from the group consisting of hydrogen and loweralkyl; and Y is a single covalent bond, —CH₂—, —CH₂CH₂—, —CH=CH—, —O—C(O)—, —C(O)—O—, —O—CH₂—, —CH₂—O—, —S—CH₂— or —CH₂—S—;
and
B₁, B₂ and B₃ are independently selected from
(1) hydrogen, (2) —Q—D wherein at each occurrence D is independently selected from the group consisting of (i) —C(O)R$_{46}$ wherein at each occurrence R$_{46}$ is independently selected from the group consisting of (a) —OR$_{46a}$ wherein at each occurrence R$_{46a}$ is independently selected from the group consisting of hydrogen, a carboxy-protecting group and arylalkyl wherein the alkyl part is substituted with an aryl group, (b) an alpha-amino acid or a beta-amino acid which is bonded via the alpha- or beta-amino group and (c) a di-, tri- or tetrapeptide which is bonded via the amino terminal amino group, (ii) —C(O)H,
(iii) —CH$_2$OH,
(iv) —C(O)CF$_3$,
(v) —CH(OH)CF$_3$,
(vi) —C(OH)(CF$_3$)$_2$,
(vii) —C(O)NH$_2$,
(viii) —C(O)NHOH,
(ix) —CH(=NOH),
(X) —S(O)$_2$NH$_2$,
(xi) —NHS(O)$_2$CH$_3$ or —NHS(O)$_2$CF$_3$,
(xii) 5-tetrazolyl,

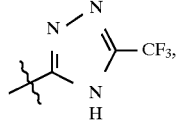

(xiii)

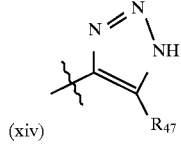

(xiv)

wherein R$_{47}$ is —CN, —NO$_2$, or —CO$_2$R$_{48}$ wherein R$_{48}$ is hydrogen, aryl or loweralkyl,

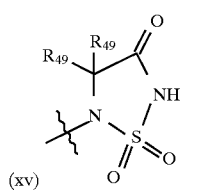

(xv)

wherein at each occurrence R$_{49}$ is independently selected from the group consisting of hydrogen and loweralkyl,

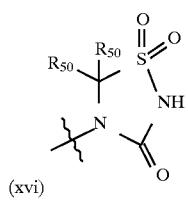

(xvi)

wherein at each occurrence R$_{50}$ is independently selected from the group consisting of hydrogen and loweralkyl,

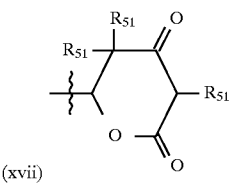

(xvii)

wherein at each occurrence R$_{51}$ is independently selected from the group consisting of hydrogen, loweralkyl, alkenyl, alkoxyalkyl and benzyl,

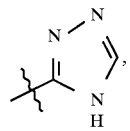

(xviii)

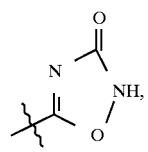

(xix)

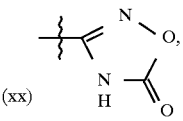

(xx)

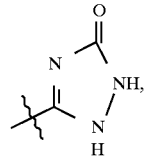

(xxi)

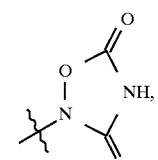

(xxii)

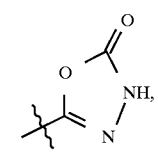

(xxiii)

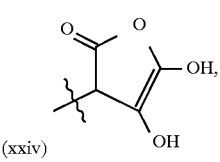

(xxiv)

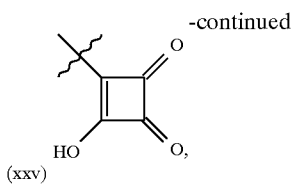

(xxv)

and wherein at each occurrence Q is independently selected from the group consisting of (i) a covalent bond, (ii) —OCH2—, (iii) alkylene, (iv) alkenylene, (v) —C(O)NH, (vi) —NHC(O)NH—, (vii) —CH(OH)— and (viii) —NHC(O)(CH$_2$)$_r$— wherein r is 0 to 4;

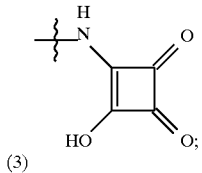

(3)

(4) —CH$_2$—N(OH)—C(O)—R$_{52}$ wherein R$_{52}$ is hydrogen, methyl or trifluoromethyl; and (5) —C(O)—NH—S(O)$_2$—R$_{53}$ wherein R$_{53}$ is aryl, heterocyclic, arylalkyl, (heterocyclic)alkyl, C$_3$–C$_7$-cycloalkyl, C$_1$–C$_8$-alkyl or perfluoro-C$_1$–C$_4$-alkyl;

with the proviso that only one or two of B$_1$, B$_2$ and B$_3$ can be hydrogen; or a pharmaceutically acceptable salt thereof.

Preferred compounds of the invention are compounds of formula (I) wherein A$_1$ is —C(O)NR$_1$R$_2$ wherein R$_1$ is selected from (i) hydrogen, (ii) loweralkyl, (iii) arylalkyl and (iv) heterocyclicalkyl and R$_2$ is

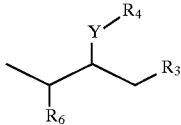

wherein R$_3$ aryl, aryl substituted with aryl, aryl substituted with aryl, aryl substituted with heterocyclic or heterocyclic; R$_4$ is aryl, aryl substituted with aryl, aryl substituted with aryl, aryl substituted with heterocyclic or heterocyclic; R$_6$ is hydrogen or lower alkyl; and Y is a single covalent bond, —CH$_2$—, —CH$_2$CH$_2$—, —CH=CH—, —O—C(O)—, —C(O)—O—, —O—CH$_2$—, —CH$_2$—O—, —S—CH$_2$— or —CH$_2$—S—; and B$_1$, B$_2$ and B$_3$ at each occurrence are independently selected from hydrogen, —CH$_2$OH, and —C(O)—OR$_{46a}$ wherein at each occurrence R$_{46a}$ is independently selected from the group consisting of (i) hydrogen, (ii) arylalkyl wherein the alkyl part is substituted with aryl and (iii) a carboxy protecting group, with the proviso that only one or two of B$_1$, B$_2$ and B3 can be hydrogen; or a pharmaceutically acceptable salt thereof.

More preferred compounds of the invention are compounds of formula (I) wherein A$_1$ is —C(O)NR$_1$R$_2$ wherein R$_1$ is selected from (i) hydrogen, (ii) lower alkyl, and (iii) arylalkyl and R$_2$

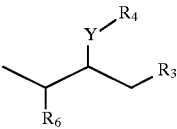

wherein R$_3$ and R$_4$ are independently selected from (i) phenyl, (ii) phenyl substituted with one or two substituents independently selected from loweralkyl, halo, hydroxy, alkoxy, and aryl or heterocyclic wherein the aryl or heterocyclic group is unsubstituted or substituted with one or two substituents independently selected from loweralkyl, halo and alkoxy, (iii) naphthyl and (iv) naphthyl substituted with one or two substituents independently selected from loweralkyl, halo, hydroxy, alkoxy and aryl or heterocyclic wherein the aryl or heterocyclic group is unsubstituted or substituted with one or two substituents independently selected from loweralkyl, halo and alkoxy; R$_6$ is lower alkyl; and Y is a single covalent bond, —CH$_2$—, —CH$_2$CH$_2$—, —CH=CH—, —O—C(O)—, —C(O)—O—, —O—CH$_2$—, —CH$_2$—O—, —S—CH$_2$— or —CH$_2$—S—; and B$_1$, B$_2$ and B$_3$ at each occurrence are independently selected from hydrogen, —CH$_2$OH, and —C(O)—OR$_{46a}$ wherein at each occurrence R$_{46a}$ is independently selected from the group consisting of hydrogen and a carboxy protecting group, with the proviso that only one or two of B$_1$, B$_2$ and B$_3$ can be hydrogen; or a pharmaceutically acceptable salt thereof.

Even more preferred compounds of the invention are compounds of formula (I) wherein A$_1$ is —C(O)NR$_1$R$_2$ wherein R$_1$ is selected from hydrogen, methyl, benzyl, naphthylmethyl and (heterocyclic)methyl and R$_2$ is

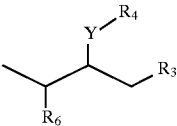

wherein R$_3$ is phenyl, 3-chlorophenyl, 4-chlorophenyl, 4-fluorophenyl, 4-methylphenyl, 3,4-dichlorophenyl, 4-methoxyphenyl, 3-bromophenyl, 3-biphenylyl, 4-biphenylyl, 4'-chloro-4-biphenylyl, 2-fluoro-4-biphenylyl, 6-fluoro-3-biphenylyl, 3-(2-naphthyl)phenyl, 3-(1-naphthyl)phenyl, 4-(2-naphthyl)phenyl, 1-naphthyl, 2-naphthyl, pyridyl, thienyl, quinolinyl, benzothiophenyl, or 3-(3-thienyl)phenyl; R$_4$ is 4-biphenylyl, 4-chlorophenyl, 4-methylphenyl, 4-bromophenyl, 4-t-butylphenyl, 4-methoxyphenyl, 3-chlorophenyl, 2-naphthyl, 4'-chloro-4-biphenylyl, 4-(3-thienyl)phenyl, 4-(3-pyridyl)phenyl, 3'-chloro-4-biphenylyl, 3,4-dichlorophenyl, 3,4-difluorophenyl, 3,4-dimethylphenyl, 3-chloro-4-methylphenyl, 4-chlro-3-methylphenyl, 3,4-dimethoxyphenyl, 3,4,-methylenedioxphenyl, 3-bromophenyl, 4-(2-naphthyl)phenyl, 2-fluoro-4-biphenylyl, 4-(2-furyl)phenyl, 3', 4'-methylenedioxy-4-biphenylyl, 2'-fluoro-4-biphenylyl, 2'-methoxy-4-biphenylyl, 4-(5-oxazolyl)phenyl or 2-naphthyl; R$_6$ is loweralkyl; and Y is a single covalent bond, —CH$_2$—, —CH$_2$CH$_2$—, —CH=CH—, —O—C(O)—, —C(O)—O—, —O—CH$_2$—, —CH$_2$—O—, —S—CH$_2$— or —CH$_2$—S—; and B$_1$, B$_2$ and B$_3$ at each occurrence are independently selected from hydrogen, —CH$_2$OH, and —C(O)—OR$_{46a}$ wherein at each occurrence R$_{46a}$ is independently selected from hydrogen and a carboxy protecting group, with the proviso that only one or two of B$_1$, B$_2$ and B$_3$ can be hydrogen; or a pharmaceutically acceptable salt thereof.

Most preferred compounds of the invention are compounds of formula (I) wherein $A_1$ is —C(O)NR$_1$R$_2$ wherein $R_1$ is hydrogen and $R_2$ is —CH(CH$_3$)CH(OC(O)—2-naphthyl)(3,4-dichlorobenzyl) or —CH(CH$_3$)CH(4-biphenylyl)(4-chlorobenzyl); and $B_1$, $B_2$ and $B_3$ at each occurrence are independently selected from hydrogen, —CH$_2$OH, and —C(O)—OR$_{46a}$ wherein at each occurrence $R_{46a}$ is independently selected from hydrogen and a carboxy protecting group, with the proviso that only one or two of $B_1$, $B_2$ and $B_3$ can be hydrogen; or a pharmaceutically acceptable salt thereof.

Another embodiment of the present invention is a cyclobutane compound of formula (II):

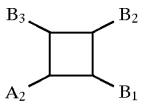

wherein $A_2$ is (1) —X—T—G wherein T is selected from the group consisting of
a) a covalent bond,
b) —C(O)—,
c) —C(S)— and
d) —S(O)$_2$—, X is selected from the group consisting of
a) a covalent bond,
b) —CH$_2$—,
c) —O—,
d) —S— and
e) —N(R$_a$)— wherein R$_a$ is hydrogen, loweralkyl, cycloalkyl, cycloalkylalkyl or arylalkyl, and G is selected from the group consisting of
a) R$_{42}$,
b) —N(R$_{41}$)(R$_{42}$)

wherein $R_{41}$ is selected from the group consisting of
(i) —CH(R$_d$)C(O)OR$_e$ wherein R$_d$ is selected from the group consisting of loweralkyl, cycloalkyl, cycloalkylalkyl, alkoxyalkyl, thioalkoxyalkyl, hydroxyalkyl, aminoalkyl, carboxyalkyl, alkoxycarbonylalkyl, arylalkyl and alkylsulfonylalkyl and R$_e$ is selected from the group consisting of hydrogen and carboxy-protecting group,
(ii) aryl,
(iii) arylalkyl,
(iv) heterocyclic,
(v) (heterocyclic)alkyl,
(vi) cycloalkylalkyl and
(vii) aryl, heterocyclic, arylalkyl or (heterocyclic)alkyl wherein the aryl group, the aryl part of the arylalkyl group, the heterocyclic group or the heterocyclic part of the (heterocyclic)alkyl group is substituted with one or two substituents —W—R$_{43}$ wherein at each occurrence W is independently selected from the group consisting of
(a) a covalent bond, (b) —C(O)—, (c) —CH$_2$—, (d) —O—, (e) —S(O)$_p$— wherein p is 0, 1 or 2, (f) —N(R$_c$)— wherein R$_c$ is hydrogen or loweralkyl, (g) —CH$_2$O—, (h) —CH$_2$S(O)$_p$— wherein p is 0, 1 or 2 and (i) —CH$_2$N(R$_c$)— wherein R$_c$ is hydrogen or loweralkyl and at each occurrence $R_{43}$ is independently selected from the group consisting of (a) aryl, (b) arylalkyl,
(c) cycloalkyl, (d) cycloalkylalkyl, (e) heterocyclic and
(f) (heterocyclic)alkyl, and $R_{42}$ is selected from the group consisting of
(i) aryl,
(ii) arylalkyl,
(iii) alkenyl,
(iv) alkynyl,
(v) arylalkenyl,
(vi) arylalkynyl,
(vii) (heterocyclic)alkyl,
(viii) aryloxyalkyl,
(ix) aryloxyalkenyl,
(x) arylalkoxyalkenyl,
(xi) arylalkyl wherein the alkyl group is substituted with
(a) —OR$_{10}$ wherein R$_{10}$ is hydrogen or alkanoyl or (b) —C(O)OR$_h$ wherein R$_h$ is hydrogen or a carboxy-protecting group,
(xii) aroyloxyalkyl, and
(xiii) aryl, arylalkyl or (heterocyclic)alkyl wherein the aryl group, the the aryl part of the arylalkyl group or the heterocyclic part of the (heterocyclic)alkyl group is substituted with one or two substituents —W'—R$_{44}$ wherein at each occurrence W' is independently selected from the group consisting of
(a) a covalent bond, (b) —C(O)—, (c) —CH$_2$—, (d) —O—, (e) —S(O)$_m$— wherein m is 0, 1 or 2, (f) —N(R$_b$)— wherein R$_b$ is hydrogen or loweralkyl, (g) —CH$_2$O—, (h) —CH$_2$S(O)$_m$— wherein m is 0, 1 or 2 and
(i) —CH$_2$N(R$_b$)— wherein R$_b$ is hydrogen or loweralkyl and at each occurrence R$_{44}$ is independently selected from the group consisting of (a) aryl, (b) arylalkyl, (c) cycloalkyl, (d) cycloalkylalkyl, (e) heterocyclic and (f) (heterocyclic)alkyl, and c) —NHR$_{42a}$ or —OR$_{42a}$
wherein R$_{42a}$ is selected from the group consisting of
(i) arylalkyl and
(ii) heterocyclicalkyl,
wherein the alkyl part of the arylalkyl group or the heterocyclicalkyl group is substituted with an arylalkyl group and wherein the aryl part of the arylalkyl group or the heterocyclic part of the heterocyclicalkyl group is substituted with one or two substituents —W"—R$_{45}$ wherein at each occurrence W" is independently selected from the group consisting of (a) a covalent bond, (b) —C(O)—, (c) —CH$_2$—, (d) —O—, (e) —S(O)$_{m'}$— wherein m' is 0, 1 or 2, (f) —N(R$_{b'}$)— wherein R$_{b'}$ is hydrogen or loweralkyl, (g) —CH$_2$O—, (h) —CH$_2$S(O)$_{m'}$— wherein m' is 0, 1 or 2 and (i) —CH$_2$N(R$_{b'}$)— wherein R$_{b'}$ is hydrogen or loweralkyl and at each occurrence R$_{45}$ is independently selected from the group consisting of (a) aryl, (b) arylalkyl, (c) cycloalkyl, (d) cycloalkylalkyl, (e) heterocyclic and (f) (heterocyclic)alkyl;

(2) —C(O)R$_{42a}$ wherein at each occurrence R$_{42a}$ is independently defined as above;

(3) —CH(OH)R$_{42a}$ wherein at each occurrence R$_{42a}$ is independently defined as above;

(4) —CH=C(R$_{42b}$)(R$_{42c}$) wherein at each occurrence R$_{42b}$ is independently selected from arylalkyl and at each occurrence R$_{42c}$, is independently selected from the group consisting of aryl and heterocyclic wherein the aryl or heterocyclic ring is subsubstituted with —W"—R$_{45}$ wherein at each occurrence W" and R$_{45}$ are independently defined as above; or (5) —C(O)—CH(R$_{42a}$)CH(R$_{42d}$)C(O)OR$_g$ wherein at each occurrence R$_{42a}$ is independently defined as above, at each occurrence R$_{42d}$ is independently selected from aryl and at each occurrence R$_g$ is independently selected from the group consisting of hydrogen and a carboxy-protecting group; and B$_1$, B$_2$ and B$_3$ are independently selected from (1) hydrogen, (2) —Q—D wherein at each occurrence D is independently selected from the group consisting of (i) —C(O)R$_{46}$ wherein at each occurrence R$_{46}$ is independently selected from the group consisting of (a) —OR$_{46a}$ wherein at each occurrence R$_{46a}$ is independently selected from the group consisting of hydrogen, a carboxy-protecting group and arylalkyl wherein the alkyl part is substituted with an aryl group, (b) an alpha-amino acid or a beta-amino acid which is bonded via the alpha- or beta-amino group and (c) a di-, tri- or tetrapeptide which is bonded via the amino terminal amino group, (ii) —C(O)H,
(iii) —CH$_2$OH,
(iv) —C(O)CF$_3$,
(v) —CH(OH)CF$_3$,
(vi) —C(OH)(CF$_3$)$_2$,
(vii) —C(O)NH$_2$,
(viii) —C(O)NHOH,
(ix) —CH(=NOH),
(X) —S(O)$_2$NH$_2$,
(xi) —NHS(O)$_2$CH$_3$ or —NHS(O)$_2$CF$_3$,
(xii) 5-tetrazolyl,

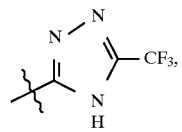

(xiii)

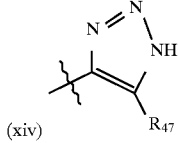

(xiv)

wherein R$_{47}$ is —CN, —NO$_2$, or —CO$_2$R$_{48}$ wherein R$_{48}$ is hydrogen, aryl or loweralkyl,

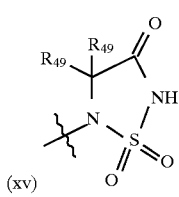

(xv)

wherein at each occurrence R$_{49}$ is independently selected from the group consisting of hydrogen and loweralkyl,

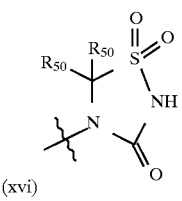

(xvi)

wherein at each occurrence R$_{50}$ is independently selected from the group consisting of hydrogen and loweralkyl,

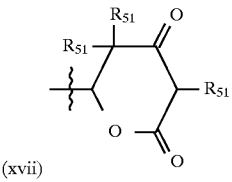

(xvii)

wherein at each occurrence R$_{51}$ is independently selected from the group consisting of hydrogen, loweralkyl, alkenyl, alkoxyalkyl and benzyl,

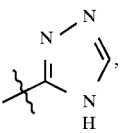

(xviii)

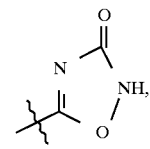

(xix)

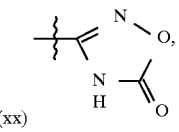

(xx)

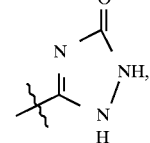

(xxi)

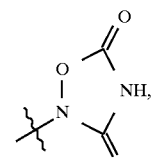

(xxii)

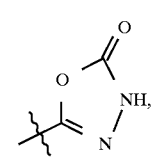

(xxiii)

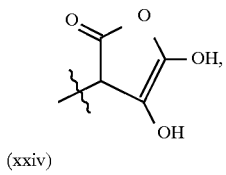

(xxiv)

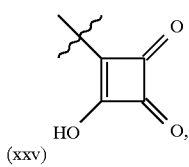

(xxv)

and
wherein at each occurrence Q is independently selected from the group consisting of (i) a covalent bond, (ii) —OCH$_2$—, (iii) alkylene, (iv) alkenylene, (v) —C(O)NH, (vi) —NHC(O)NH—, (vii) —CH(OH)— and (viii) —NHC(O)(CH$_2$)$_r$— wherein r is 0 to 4;

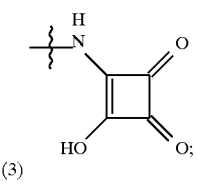

(3)

(4) —CH$_2$—N(OH)—C(O)—R$_{52}$ wherein R$_{52}$ is hydrogen, methyl or trifluoromethyl; and (5) —C(O)—NH—S(O)$_2$—R$_{53}$ wherein R$_{53}$ is aryl, heterocyclic, arylalkyl, (heterocyclic)alkyl, C$_3$–C$_7$-cycloalkyl, C$_1$–C$_8$-alkyl or perfluoro-C$_1$–C$_4$-alkyl;

with the proviso that only one or two of B$_1$, B$_2$ and B$_3$ can be hydrogen;

or a pharmaceutically acceptable salt thereof.

Preferred compounds of the invention are compounds of formula (II) wherein A$_2$ is —C(O)NR$_{41}$R$_{42}$, —N(R$_a$)—C(O)NR$_{41}$R$_{42}$ wherein R$_a$ is hydrogen, loweralkyl, cycloalkyl, cycloalkylalkyl or arylalkyl, —O—C(O)NR$_{41}$R$_{42}$ or —CH$_2$—C(O)NR$_{41}$ R$_{42}$ wherein R$_{41}$ is selected from the group consisting of (i) aryl, (ii) arylalkyl, (iii) heterocyclic, and (iv) (heterocyclic)alkyl, and R$_{42}$ is selected from (i) aryl, (ii) arylalkyl, (iii) alkenyl, (iv) alkynyl, (v) arylalkenyl, (vi) arylalkynyl, (vii) (heterocyclic)alkyl, (viii) aryloxyalkyl, (ix) aryloxyalkenyl, (x) arylalkoxyalkenyl, (xi) arylalkyl wherein the alkyl group is substituted with —OR$_{10}$ wherein R$_{10}$ is hydrogen or alkanoyl, and (xii) aryl, arylalkyl or (heterocyclic)alkyl wherein the aryl group, the the aryl part of the arylalkyl group or the heterocyclic part of the (heterocyclic)alkyl group is substituted with —W'—R$_{44}$ wherein W' is selected from the group consisting of (a) a covalent bond, (b) —C(O)—, (c) —CH$_2$—, (d) —O—, (e) —S(O)$_p$— wherein p is 0, 1 or 2, (f) —N(R$_b$)— wherein R$_b$ is hydrogen or loweralkyl, (g) —CH$_2$O—, (h) —CH$_2$S(O)$_m$— wherein m is 0, 1 or 2 and (i) —CH$_2$N(R$_b$)— wherein R$_b$ is hydrogen or loweralkyl and R$_{44}$ is selected from the group consisting of (a) aryl, (b) arylalkyl, (c) cycloalkyl, (d) cycloalkylalkyl, (e) heterocyclic and (f) (heterocyclic)alkyl;

and B$_1$, B$_2$ and B$_3$ at each occurrence are independently —C(O)—OR$_{46a}$ wherein at each occurrence R$_{46a}$ is independently selected from the group consisting of (i) hydrogen, (ii) arylalkyl wherein the alkyl part is substituted with aryl and (iii) a carboxy protecting group;

or a pharmaceutically acceptable salt thereof.

More preferred compounds of the invention are compounds of formula (II) wherein A$_2$ is —C(O)NR$_{41}$R$_{42}$ wherein R$_{41}$ is (i) arylalkyl or (ii) (heterocyclic)alkyl and R$_{42}$ is selected from the group consisting of (i) arylalkyl, (ii) arylalkenyl, (iii) aryloxyalkyl, (iv) aryloxyalkenyl, (v) arylalkoxyalkenyl, (vi) arylalkyl wherein the alkyl group is substituted with —OR$_{10}$ wherein R$_{10}$ is hydrogen or alkanoyl, and (vii) aryl, arylalkyl or (heterocyclic)alkyl wherein the aryl group, the the aryl part of the arylalkyl group or the heterocyclic part of the (heterocyclic)alkyl group is substituted with —W'—R$_{44}$ wherein W' is selected from the group consisting of (a) a covalent bond, (b) —CH$_2$—, and (c) —O— and R$_{44}$ is selected from (a) aryl, (b) arylalkyl, (c) heterocyclic and (d) (heterocyclic)alkyl; and B$_1$, B$_2$ and B$_3$ at each occurrence are independently —C(O)—OR$_{46a}$ wherein at each occurrence R$_{46a}$ is independently selected from the group consisting of hydrogen and a carboxy protecting group;

or a pharmaceutically acceptable salt thereof.

Even more preferred compounds of the invention are compounds of formula (II) wherein A$_2$ is —C(O)NR$_{41}$R$_{42}$ wherein R$_{41}$ is benzyl or (heterocyclic)methyl and R$_{42}$ is selected from the group consisting of 4-(phenoxy)benzyl, (4-hydroxy-5-methyl)-6-phenylhexyl, 4-acetoxy-5-methyl-6-phenylhexyl, 5-phenyl-2,4-pentadienyl, and 3-phenyl-2-propenyl; and B$_1$, B$_2$ and B$_3$ at each occurrence are independently —C(O)—OR$_{46a}$ wherein at each occurrence R$_{46a}$ is independently selected from the group consisting of hydrogen and a carboxy protecting group;

or a pharmaceutically acceptable salt thereof.

Most preferred compounds of the invention are compounds of formula (II) wherein A$_2$ is —C(O)NR$_{41}$ R$_{42}$ wherein R$_{41}$ is benzyl or thien-2-ylmethyl and R$_{42}$ is 3-chloro-4-(phenoxy)benzyl, 4-(phenoxy)benzyl, (4-hydroxy-5-methyl)-6-phenylhexyl, 4-acetoxy-5-methyl)-6-phenylhexyl, 5-phenyl-2,4-pentadienyl, or 3-phenyl-2-propenyl; and B$_1$, B$_2$ and B$_3$ at each occurrence are independently —C(O)—OR$_{46a}$ wherein at each occurrence R$_{46a}$ is independently selected from the group consisting of hydrogen and a carboxy protecting group; or a pharmaceutically acceptable salt thereof.

The present invention also relates to processes for preparing the the compounds of formula (I) and formula (II) and to the synthetic intermediates useful in such processes.

In a further aspect of the present invention are disclosed pharmaceutical compositions which comprise a compound of the formula (I) or (II) of the present invention in combination with a pharmaceutically acceptable carrier.

In yet another aspect of the present invention are disclosed pharmaceutical compositions which comprise a compound of the formula (I) of the present invention in combination with another antihyperlipoproteinemic agent and/or with one or more other serum cholesterol lowering agents or HMG CoA reductase inhibitors and a pharmaceutically acceptable carrier.

In yet another aspect of the present invention is disclosed a method for inhibiting squalene synthase in a human or lower mammal, comprising administering to the patient a therapeutically effective amount of a compound of the formula (I) of the present invention.

In yet another aspect of the present invention is disclosed a method for inhibiting or treating atherosclerosis or inhibiting or treating hyperlipidemia which would inhibit the development of atherosclerosis in a human or lower mammal, comprising administering to the patient a therapeutically effective amount of a compound of the formula (I) of the invention alone or in combination with another cardiovascular agent.

Also disclosed is a method for treating fungal infections in a human or lower mammal, comprising administering to the patient a therapeutically effective amount of a compound of the formula (I) of the invention.

Also disclosed is a method for treating acne in humans, comprising administering to the patient a therapeutically effective amount of a compound of the formula (I) of the present invention.

In yet another aspect of the present invention are disclosed pharmaceutical compositions which comprise a compound of the formula (I) or (II) of the present invention in combination with another chemotherapeutic agent and a pharmaceutically acceptable carrier.

In yet another aspect of the present invention is disclosed a method of inhibiting protein farnesyltransferase in a human or lower mammal, comprising administering to the patient a therapeutically effective amount of a compound of the formula (I) or (II) of the present invention.

In yet another aspect of the present invention is disclosed a method of treating cancer in a human or lower mammal, comprising administering to the patient a therapeutically effective amount of a compound of the formula (I) or (II) of the present invention alone or in combination with another chemotherapeutic agent.

In yet another aspect of the present invention is disclosed a method of treating or preventing restenosis in a human or lower mammal, comprising administering to the patient a therapeutically effective amount of a compound of the formula (I) or (II) of the present invention.

The compounds of the invention comprise asymmetrically substituted carbon atoms. As a result, all stereoisomers of the compounds of the invention are meant to be included in the invention, including racemic mixtures, mixtures of diastereomers, as well as single diastereomers of the compounds of the invention. Methods for preparing various stereoisomers are described in E. M. White and H. C. Dunathan, J. Amer. Chem. Soc., 78: 6055–6057 (1956), R. Crigee and H. Hover, Chem. Ber., 93: 2521–2524 (1960) and R. Crigee and W. Funke, Chem Ber., 94: 2538–2539 (1961). The terms "S" and "R" configuration, as used herein, are as defined by the IUPAC 1974 Recommendations for Section E, Fundamental Stereochemistry, Pure Appl. Chem. (1976) 45, 13–30.

The terms α and β are employed to describe relative orientation for ring substituents on cyclic compounds, i.e., substituted cyclobutanes in the present invention. The ax-side of the reference plane (the plane formed by the cyclobutane ring) is that side on which the highest ranking substituent (according to the Cahn-lngold-Prelog Sequence Rule) lies at the lowest-numbered stereogenic carbon atom. All substituents lying on the same side of the reference plane as the highest-ranking substituent are assigned an α descriptor. Those substituents lying on the opposite side of the reference plane are assigned a β descriptor. It should be noted that this usage does not describe absolute configuration. The terms α and β configuration, as used herein, are as defined by the Chemical Abstracts Index Guide-Appendix IV (1987)¶ 203.

The term "α-amino acid" or "alpha-amino acid" refers to an α-amino acid selected from the group consisting of alanine, arginine, asparagine, aspartic acid, cysteine, glutamine, glutamic acid, glycine, histidine, isoleucine, leucine, lysine, methionine, norleucine, ornithine, phenylalanine, proline, sarcosine, serine, threonine, tryptophan, tyrosine and valine. The stereochemistry at the asymmetric center can be of the D- or L- configuration.

The term "β-amino acid" or "beta-amino acid" refers to an amino acid wherein the amino group is β to the carboxylic acid functionality. Examples of β-amino acids include β-alanine, β-phenylalanine and the like.

The term "dipeptide" as used herein refers to $AA_1$-$AA_2$ wherein $AA_1$ and $AA_2$ are independently selected from α- and β-amino acids as described above coupled together by an amide bond (—C(O)—NH—) between the carboxy terminus of $AA_1$, and the amino terminus of $AA_2$. Examples of dipeptides include H—Glycyl-Alanine—OH, H—Glycyl-β-Alanine—OH, H—Leucyl-Glycine—OH and the like.

The term "tripeptide" as used herein refers to $AA_1$-$AA_2$-$AA_3$ wherein $AA_1$, $AA_2$ and $AA_3$ are independently selected from α- and β-amino acids as described above coupled together by amide bonds (—C(O)—NH—) between the carboxy terminus of $AA_1$ and the amino terminus of $AA_2$ and the carboxy terminus of $AA_2$ and the amino terminus of $AA_3$. Examples of tripeptides include H—Glycyl-Alanyl-Leucine—OH, H—Glycyl-β-Alanyl—Sarcosine—OH, H—Leucyl-Glycyl-Alanine—OH and the like.

The term "tetrapeptide" as used herein refers to $AA_1$-$AA_2$-$AA_3$-$AA_4$ wherein $AA_1$, $AA_2$, $AA_3$ and $AA_4$ are independently selected from α- and β-amino acids as described above coupled together by amide bonds (—C(O)—NH—) between the carboxy terminus of $AA_1$ and the amino terminus of $AA_2$, the carboxy terminus of $AA_2$ and the amino terminus of $AA_3$, and the carboxy terminus of $AA_3$ and the amino terminus of $AA_4$.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. No. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy)ethyl, 2-(5-indanyloxycarbonyloxy)ethyl and the like; alkoxyalkylcarbonyloxyalkyl, such as 2-(1-methoxy-2-methylpropan-2-oyloxy)ethyl and like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "alkanoyl" as used herein refers to $R_{85}C(O)$— wherein $R_{85}$ is a loweralkyl group.

The term "alkanoylaminoalkyl" as used herein refers to a loweralkyl radical to which is appended $R_{86}$—NH— wherein $R_{86}$ is an alkanoyl group.

The term "alkanoyloxy" as used herein refers to $R_{87}C(O)$—O— wherein $R_{87}$ is a loweralkyl group.

The term "alkanoyloxyalkyl" as used herein refers to a loweralkyl radical to which is appended an alkanoyloxy group.

The term "alkenyl" as used herein refers to a branched or straight hydrocarbon chain comprising two to twenty carbon atoms which also comprises one or more carbon-carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "alkenylene" denotes a divalent group derived from a straight or branched chain hydrocarbon containing from 2 to 10 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkoxy" as used herein refers to RO— wherein R is a lower alkyl group. Representative examples of alkoxy groups include methoxy, ethoxy, t-butoxy and the like.

The term "alkoxyalkoxy" as used herein refers to $R_{80}O$—$R_{81}O$— wherein $R_{80}$ is loweralkyl as defined above and $R_{81}$ is an alkylene group. Representative examples of alkoxyalkoxy groups include methoxymethoxy, ethoxymethoxy, t-butoxymethoxy and the like.

The term "alkoxyalkyl" as used herein refers to an alkoxy group as previously defined appended to an alkyl radical as previously defined. Examples of alkoxyalkyl include, but are not limited to, methoxymethyl, methoxyethyl, isopropoxymethyl and the like.

The term "alkoxyalkylcarbonyloxyalkyl" as used herein refers to a loweralkyl radical to which is appended $R_{96}$—C(O)—O— wherein $R_{96}$ is an alkoxyalkyl group.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylalkyl" as used herein refers to an alkoxylcarbonyl group as previously defined appended to a lower alkyl radical. Examples of alkoxycarbonylalkyl include methoxycarbonylmethyl, 2-ethoxycarbonylethyl and the like.

The term "alkoxycarbonylaminoalkyl" as used herein refers to a loweralkyl radical to which is appended $R_{97}$—NH— wherein $R_{97}$ is an alkoxycarbonyl group.

The term "alkoxycarbonyloxyalkyl" as used herein refers to a loweralkyl radical to which is appended $R_{93}$—O— wherein $R_{93}$ is an alkoxycarbonyl group.

The term "alkylamino" as used herein refers to $R_{51}$ NH— wherein $R_{51}$ is a lower alkyl group, for example, methylamino, ethylamino, butylamino, and the like.

The term "alkylaminocarbonylaminoalkyl" as used herein refers to a loweralkyl radical to which is appended $R_{98}$—C(O)—NH— wherein $R_{98}$ is an alkylamino group.

The term "alkylsulfonyl" as used herein refers to $R_{82}S(O)_2$— wherein $R_{82}$ is a loweralkyl group.

The term "alkylene" denotes a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "alkylsulfonylalkyl" as used herein refers to a loweralkyl radical to which is appended an alkylsulfonyl group.

The term "alkynyl" as used herein refers to a branched or straight hydrocarbon chain comprising two to twenty carbon atoms which also comprises one or more carbon-carbon triple bonds. Representative alkynyl groups include ethynyl, 2-propynyl (propargyl), 1-propynyl and the like.

The term "amino" as used herein refers to —$NH_2$.

The term "aminoalkyl" as used herein refers a loweralkyl radical to which is appended an amino group.

The term "aroyloxyalkyl" as used herein refers to an alkyl radical which is substituted with $R_{20}C(O)$—O— where $R_{20}$ is an aryl group. Examples of aroyloxyalkyl groups include benzoyloxymethyl, 1-naphthoyloxymethyl, 2-naphthoyloxymethyl and the like.

The term "aryl" as used herein refers to a mono-, bi- or tricyclic carbocyclic ring system comprising 6–14 carbon atoms and having one, two or three aromatic rings including, but not limited to, phenyl, naphthyl, tetrahydronaphthyl, indanyl, indenyl, fluorenyl, anthracenyl, dihydroanthracenyl and the like. Aryl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. In addition, substituted aryl groups include tetrafluorophenyl and pentafluorophenyl.

The term "arylalkenyl" as used herein refers to an aryl group as previously defined appended to an alkenyl radical as previously defined. Examples of arylalkenyl include styryl (i.e., 2-phenylethenyl), 2-(1-naphthyl)ethenyl and the like.

The term "arylalkenyloxycarbonyloxyalkyl" as used herein refers to a loweralkyl radical to which is appended $R_{95}$—O—C(O)—O— wherein $R_{95}$ is an arylalkenyl group.

The term "arylalkoxy" as used herein refers to $R_{84}$O— wherein $R_{84}$ is an arylalkyl group.

The term "arylalkoxyalkenyl" as used herein refers to an alkenyl radical to which is appended an arylalkoxy group.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylcarbonyloxyalkyl" as used herein refers to a lower alkyl radical to which is appended an arylalkylcarbonyloxy group (i.e., $R_{91}C(O)O$— wherein $R_{91}$ is an arylalkyl group).

The term "arylalkyloxycarbonyloxyalkyl" as used herein refers to a loweralkyl radical to which is appended $R_{92}$—O—C(O)—O— wherein $R_{92}$ is an arylalkyl group.

The term "arylalkynyl" as used herein refers to an alkynyl radical to which is appended an aryl group.

The term "aryloxy" as used herein refers to $R_{83}$O— wherein $R_{83}$ is an aryl group.

The term "aryloxyalkenyl" as used herein refers to an alkenyl radical to which is appended an aryloxy group.

The term "aryloxyalkyl" as used herein refers to a loweralkyl radical to which is appended an aryloxy group.

The term "aryloxycarbonyloxyalkyl" as used herein refers to a lower alkyl radical to which is appended $R_{94}$—O—C(O)—O— wherein $R_{94}$ is an aryl group.

The term "aryl-substituted cycloalkylalkyl" as used herein refers to a cycloalkylalkyl radical in which the alkyl portion of the radical is substituted with an aryl group. Examples of aryl-substituted cycloalkylalkyl include α-(cyclopropylmethyl)benzyl, α-(cyclobutylmethyl)benzyl and the like.

The term "carboxaldehyde" as used herein refers to the group —C(O)H.

The term "carboxamide" as used herein refers to the group —$C(O)NH_2$.

The term "carboxyalkyl" as used herein refers to a loweralkyl radical to which is appended a carboxy (—COOH) group.

The term "cycloalkanoyloxyalkyl" as used herein refers to a loweralkyl radical to which is appended a cycloalkanoyloxy group (i.e., $R_{88}$—C(O)O— wherein $R_{88}$ is a cycloalkyl group).

The term "cycloalkyl" as used herein refers to an alicyclic group comprising from 3 to 10 carbon atoms including, but not limited to, cyclopropyl, cyclobutyl, cyclopentyl, cyclohexyl, norbornyl, adamantyl and the like.

The term "cycloalkylalkyl" as used herein refers to a lower alkyl radical to which is appended a cycloalkyl group. Representative examples of cycloalkylalkyl include cyclopropylmethyl, cyclohexylmethyl, 2-(cyclopropyl)ethyl, adamantylmethyl and the like.

The term "cycloalkyloxycarbonylalkyl" as used herein refers to a lower alkyl radical to which is appended $R_{89}$—O—C(O)— wherein $R_{89}$ is a cycloalkyl group.

The term "cycloalkyloxycarbonyloxyalkyl" as used herein refers to a loweralkyl radical to which is appended $R_{90}$—O—C(O)—O— wherein $R_{90}$ is a cycloalkyl group.

The term "dialkylamino" as used herein refers to $R_{56}R_{57}N$— wherein $R_{56}$ and $R_{57}$ are independently selected from loweralkyl, for example dimethylamino, diethylamino, methyl propylamino, and the like.

The term "dialkylaminoalkyl" as used herein refers to a loweralkyl radical to which is appended a dialkylamino group.

The term "dialkyaminocarbonylalkyl" as used herein refers to a loweralkyl radical to which is appended $Rg_{99}$—C(O)— wherein $R_{99}$ is a dialkylamino group.

The term "haloalkyl" as used herein refers to a lower alkyl radical, as defined above, bearing at least one halogen substituent, for example, chloromethyl, fluoroethyl or trifluoromethyl and the like.

The term "halogen" or "halo" as used herein refers to I, Br, Cl or F.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

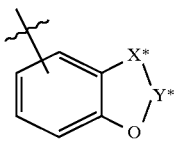

where $X^*$ is —$CH_2$— or —O— and $Y^*$ is —C(O)— or [—$C(R'')_2$—]$_v$ where R'' is hydrogen or $C_1$–$C_4$-alkyl and v is 1, 2 or 3 such as 1,3-benzodioxolyl, 1,4-benzodioxanyl and the like.

Heterocyclics can be unsubstituted or monosubstituted or disubstituted with substituents independently selected from hydroxy, halo, oxo (=O), alkylimino ($R^*N$= wherein $R^*$ is a lower alkyl group), amino, alkylamino, dialkylamino, alkoxy, alkoxyalkoxy, haloalkyl, cycloalkyl, aryl, arylalkyl, —COOH, —$SO_3H$ and loweralkyl. In addition, nitrogen containing heterocycles can be N-protected.

The term "(heterocyclic)alkyl" as used herein refers to a heterocyclic group as defined above appended to a lower alkyl radical as defined above. Examples of heterocyclic alkyl include 2-pyridylmethyl, 4-pyridylmethyl, 4-quinolinylmethyl and the like.

The term "heterocycliccarbonyloxyalkyl" as used herein refers to a lower alkyl radical to which is appended $R_{100}$—C(O)—O— wherein $R_{100}$ is a heterocyclic group.

The term "heterocyclic-substituted cycloalkylalkyl" as used herein refers to a cycloalkylalkyl radical in which the alkyl portion of the radical is substituted with a heterocyclic group. Examples of heterocyclic-substituted cycloalkylalkyl include α-(cyclopropylmethyl)furan-2-ylmethyl, α-(cyclobutylmethyl)thien-2-ylmethyl and the like.

The term "hydroxyalkyl" as used herein refers to a lower alkyl radical to which is appended a hydroxy (—OH) group.

The term "lower alkyl" as used herein refers to branched or straight chain alkyl groups comprising one to ten carbon atoms, including methyl, ethyl, propyl, isopropyl, n-butyl, t-butyl, neopentyl and the like.

The term "thioalkoxy" as used herein refers to $R_{70}S$— wherein $R_{70}$ is loweralkyl. Examples of thioalkoxy include, but are not limited to, methylthio, ethylthio and the like.

The term "thioalkoxyalkyl" as used herein refers to a thioalkoxy group as previously defined appended to a lower alkyl radical as previously defined. Examples of thioalkoxyalkyl include thiomethoxymethyl, 2-thiomethoxyethyl and the like.

The term "1,2,3,4-cyclobutanetetracarboxylic dianhydride" as used herein refers to the (1.2/3.4) compound wherein the two anhydride rings are trans (i.e., on opposite sides of the plane formed by the cyclobutane ring) to one another. The relative stereochemistry is as shown.

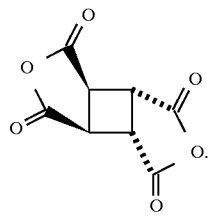

The term "(heterocyclic)carbonyl" as used herein refers to $R_{23}$—C(O)— where $R_{23}$ is a heterocyclic radical. Examples of heterocycliccarbonyl include quinoline-2-carbonyl, isoquinolin-1-carbonyl and the like.

The term "tetrazolyl" or "5-tetrazolyl" as used herein refers to a radical of the formula

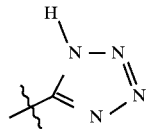

or a tautomer thereof.

Representative compounds of the invention include:
(1α,2β,3β,4α)-1-[N-Benzyl-N-{(4S*,5S*)-(4-hydroxy-5-methyl)-6-phenylhexyl}aminocarbonyl]cyclobutane-2,3,4-tricarboxylic acid;
(1α,2β,3β,4α)-1-[N-Benzyl-N-{(4S*,5S*)-(4-acetoxy-5-methyl)-6-phenylhexyl}aminocarbonyl]cyclobutane-2,3,4-tricarboxylic acid;
(1α,2β,3β,4α)-1-[N-Benzyl-N-(4-phenoxybenzyl)aminocarbonyl]-2,4-di(benzyloxycarbonyl)cyclobutane-3-carboxylic acid;
(1α,2β,3β,4α)-1-[N-Benzyl-N-(4-phenoxybenzyl)aminocarbonyl]-cyclobutane-2,3,4-tricarboxylic acid;
(1α,2β,3β,4α)-1-[N-(Thien-2-ylmethyl)-N-(4-phenoxybenzyl)-aminocarbonyl]-2,4-di(benzyloxycarbonyl)cyclobutane-3-carboxylic acid;
(1α,2β,3β,4α)-1-[N-(Thien-2-ylmethyl)-N-(4-phenoxybenzyl)-aminocarbonyl]cyclobutane-2,3,4-tricarboxylic acid;
(1α,2β,3β,4α)-1-[N-Benzyl-N-(4-phenoxybenzyl)aminocarbonyl]-2,4-di(benzyloxycarbonyl)-3-(methyloxycarbonyl)cyclobutane;
(1α,2β,3β,4α)-1-[N-Benzyl-N-(4-phenoxybenzyl)aminocarbonyl]-3-(methyloxycarbonyl)cyclobutane-2,4-dicarboxylic acid;
(1α,2β,3β,4α)-1-[N-Benzyl-N-(4-phenoxybenzyl)aminocarbonyl]-3,4-di(benzyloxycarbonyl)cyclobutane-2-carboxylic acid;
(1α,2β,3β,4α)-1-[N-Benzyl-N-(4-phenoxybenzyl)aminocarbonyl]-4-(methyloxycarbonyl)cyclobutane-2,3-dicarboxylic acid;
(1α,2β,3β,4α)-1-[N-Benzyl-N-(4-phenoxybenzyl)aminocarbonyl]-2,3-di(methoxycarbonyl)-4-(diphenylmethyloxycarbonyl)cyclobutane;

(1α,2β,3β,4α)-1-[N-Benzyl-N-(4-phenoxybenzyl)aminocarbonyl]-2,3-di(methoxycarbonyl)cyclobutane-4-carboxylic acid;

(1α,2β,3β,4α)-1-[N-Benzyl-N-(4-phenoxybenzyl)aminocarbonyl]-2-(methyloxycarbonyl)cyclobutane-3,4-dicarboxylic acid;

(1α,2β,3β,4α)-1-[N-Benzyl-N-(trans-3-phenyl-2-propenyl)aminocarbonyl]cyclobutane-2,3,4-tricarboxylic acid;

(1α,2β,3β,4α)-1-[N-Benzyl-N-(trans,trans-5-phenyl-2,4-pentadienyl)aminocarbonyl]cyclobutane-2,3,4-tricarboxylic acid;

(1α,2β,3β,4α)-1-[N-Benzyl-N-(cis-4-benzyloxy-2-butenyl)aminocarbonyl]cyclobutane-2,3,4-tricarboxylic acid;

(1α,2β,3β,4α)-1-[N-Benzyl[-N-(4-phenoxy-cis-2-butenyl)aminocarbonyl]cyclobutane-2,3,4-tricarboxylic acid;

(−)-(1α,2β,3β,4α)-1-[N-Benzyl-N-(4-phenoxybenzyl)aminocarbonyl]-cyclobutane-2,3,4-tricarboxylic acid;

(+)-(1α,2β,3β,4α)-1-[N-Benzyl-N-(4-phenoxybenzyl)aminocarbonyl]-cyclobutane-2,3,4-tricarboxylic acid;

(1S,2S,3S,4S)-2,3-Di(benzyloxycarbonyl)-4-[N-{(2S,3R)-4-(3,4-dichlorophenyl)-3-(2-naphthoyloxy)-2-butyl}aminocarbony]-cyclobutane-1-carboxylic acid;

(1R,2R,3R,4R)-2,3-Di(benzyloxycarbonyl)-4-[N-{(2S,3R)-4-(3,4-dichlorophenyl)-3-(2-naphthoyloxy)-2-butyl}aminocarbonyl]-cyclobutane-1-carboxylic acid;

(1S,2R,3R,4R)-3-Methoxycarbonyl-4-[N-{(2S,3R)-4-(3,4-dichlorophenyl)-3-naphthoyloxy)-2-butyl}aminocarbonyl]cyclobutane-1,2-dicarboxylic acid;

(1R,2S,3S,4S)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;

(1S,2R,3R,4R)-4-[N-{(2S,3R)-4-(3,4-Dichlorophenyl)-3-(2-naphthoyloxy)-2-butyl}aminocarbonyl]cyclobutane-1,2,3-tricarboxylic acid;

(1R,2S,3S,4S)-4-[N-{(2S,3R)-4-(3,4-Dichlorophenyl)-3-(2-naphthoyloxy)-2-butyl}aminocarbonyl]cyclobutane-1,2,3-tricarboxylic acid;

(1S,2S,3S,4S)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;

(1α,2α,3β,4β)-4-[N-{(2S,3R)-4-(4-chlorophenyl)-3-(4-biphenylyi)-2-butyl}aminocarbonyl]cyclobutane-1,2,3-tricarboxylic acid;

(1α,2β,3β,4α)-2-Carbomethoxy-4-[N-{(1S,2R)-4-(3,4-dichlorophenyl)-3-(2-naphthoyloxy)-2-butyl}aminocarbonyl]-1,3-dicarboxylic acid;

(1β,2α,3α,4β)-2-Carbomethoxy-4-[N-{(1S,2R)-4-(3,4-dichlorophenyl)-3-(2-naphthoyloxy)-2-butyl}aminocarbony]-1,3-dicarboxylic acid;

(1α,2β,3β)-3-[N-{(2S,3R)-4-(3,4-Dichlorophenyl)-3-(2-naphthoyloxy)-2-butyl}aminocarbony]-1,2-dicarboxylic acid;

(1α,2β,3β)-3-[N-{2S,3R}-4-(3,4-Dichlorophenyl)-3-(2-naphthoyloxy)-2-butyl}aminocarbony]cyclobutane-1,2-dicarboxylic acid;

(1β,2β,3α)-3-[N-{2S,3R}-4-(3,4-Dichlorophenyl)-3-(2-naphthoyloxy)-2-butyl}aminocarbony]cyclobutane-1,2-dicarboxylic acid;

(1β,2α,3α)-3-[N-{(2S,3R)-4-(4-chlorophenyl)-3-(4-biphenylyl)-2-butyl}aminocarbonyl]cyclobutane-1,2-dicarboxylic acid;

(1β,2β,3α,4α)-4-[N-Benzyl-N-(10-phenyldecyl)aminocarbonyl]cyclobutane-1,2,3-tricarboxylic acid;

(1β,2β,3α,4α)-4-[N-Benzyl-N-(8-phenylocyl)aminocarbonyl]cyclobutane-1,2,3-tricarboxylic acid;

2-[N-{(2S,3R)-4-(4-Chlorophenyl)-3-(4-biphenylyl)-2-butyl}aminocarbonyl]-cyclobutane-1-carboxylic acid;

(1β,2β,3α,4α)-4-[N-Benzyl-N-(4-(3-chlorophenoxy)benzyl)aminocarbonyl]-cyclobutane-1,2,3-tricarboxylic acid;

(1β,2β,3α,460 )-4-[N-Benzyl-N-(2-chloro-4-(phenoxy)benzyl)aminocarbonyl]-cyclobutane-1,2,3-tricarboxylic acid;

(1β,2β,3α,4α)-4-[N-Benzyl-N-(3-chloro-4-(phenoxy)benzyl)aminocarbonyl]-cyclobutane-1,2,3-tricarboxylic acid;

(±)-(1α,2β,4α)-2-[N-{(2S,3R)-4-(4-Chlorophenyl)-3-(4-biphenylyl)-2-butyl}aminocarbonyl]-4-hydroxymethylcyclobutane-1-carboxylic acid;

(1α,2β,3β,4α)-1-{N-Benzyl-N-[(4S*,5S*)-(4-acetoxy-5-methyl)-6-phenylhexyl]aminocarbonyl}cyclobutane-2,3,4-tricarboxylic acid;

(1α,2β,3β,4α)-4-{N-Propyl-N-[(4S*,5S*)-(5-methyl-4-naphthoyloxy)-6-phenylhexyl]aminocarbonyl}cyclobutane-1,2,3-tricarboxylic acid;

(1α,2α,3β,4β)-4-{N-Propyl-N-[(R)-6-methyl-9-phenyl-(E)-4-nonenyl]aminocarbonyl}cyclobutane-1,2,3-tricarboxylic acid;

(1α,2α,3β,4β)-4-{N-Benzyl-N-[(R)-6-methyl-9-phenyl-(E)-4-nonenyl]aminocarbonyl}cyclobutane-1,2,3-tricarboxylic acid;

(1β,2α,3α,4β)-4-[N-{2S,3R}-4-(3,4-dichlorophenyl)-3-(2-naphthoyloxy)-2-butyl}aminocarbony]]cyclobutane-1,2,3-tricarboxylic acid;

(1S,2S,3S,4S)-2,3-Di(benzyloxycarbonyl)-4-[N-{(2S,3R)-4-(4-chlorophenyl)-3-(4-biphenylyl)-2-butyl}aminocarbonyl]-cyclobutane-1-carboxylic acid;

(1R,2R,3R,4R)-2,3-Di(benzyloxycarbonyl)-4-[N-{(2S,3R)-4-(4-chlorophenyl)-3-(4-biphenylyl)-2-butyl}aminocarbonyl]-cyclobutane-1-carboxylic acid;

(1S,2R,3R,4R)-3-Methoxycarbonyl-4-[N-{(2S,3R)-4-(4-chlorophenyl)-3-(4-biphenylyl)-2-butyl}aminocarbonyl]cyclobutane-1,2-dicarboxylic acid;

(1R,2S,3S,4S)-3-Methoxycarbonyl-4-[N-{(2S,3R)-4-(4-chlorophenyl)-3-(4-biphenylyl)-2-butyl}aminocarbonyl]cyclobutane-1,2-dicarboxylic acid;

(1S,2R,3R,4R)-4-[N-{(2S,3R)-4-(4-chlorophenyl)-3-(4-biphenylyl)-2-butyl}aminocarbonyl]cyclobutane-1,2,3-tricarboxylic acid;

(1R,2S,3S,4S)-4-[N-{(2S,3R)-4-(4-chlorophenyl)-3-(4-biphonylyl)-2-butyl}aminocarbonyl]cyclobutane-1,2,3-tricarboxylic acid;

(1S,2S,3S,4S)-3-Methoxycarbonyl-4-[N-{(2S,3R)-4-(4-chlorophenyl)-3-(4-biphenylyl)-2-butyl}aminocarbonyl]cyclobutane-1,2-dicarboxylic acid;

(1α,2β,3β,4α)-2-Carbomethoxy-4-[N-{(2S,3R)-4-(4-chlorophenyl)-3-(4-biphenylyl)-2-butyl)aminocarbonyl]cyclobutane-1,3-dicarboxylic acid;

(1β,2α,3α,4β)-2-Carbomethoxy-4-[N-{(2S,3R)-4-(4-chlorophenyl)-3-(4-biphenylyl)-2-butyl}aminocarbonyl]cyclobutane-1,3-dicarboxylic acid;

(1α,2β,3β)-3-[N-{(2S,3R)-4-(4-chlorophenyl)-3-(4-biphenylyl)-2-butyl}aminocarbonyl]cyclobutane-1,2-dicarboxylic acid;

(1α,2β,3β)-3-[N-{(2S,3R)-4-(4-chlorophenyl)-3-(4-biphenylyl)-2-butyl}aminocarbonyl]cyclobutane-1,2-dicarboxylic acid; and (1β,2β,3α)-3-[N-{(2S,3R)-4-(4-chlorophenyl)-3-(4-biphenylyl)-2-butyl}aminocarbonyl]cyclobutane-1,2-dicarboxylic acid; or a pharmaceutically acceptable salt thereof.

Preferred compounds are selected from the group consisting of:
- (1α,2β,3β,4α)-1-[N-Benzyl-N-{(4S*,5S*)-(4-hydroxy-5-methyl)-6-phenylhexyl}aminocarbonyl]cyclobutane-2,3,4-tricarboxylic acid;
- (1α,2β,3β,4α)-1-[N-Benzyl-N-(4-phenoxybenzyl)aminocarbonyl]-cyclobutane-2,3,4-tricarboxylic acid;
- (1α,2β,3β,4α)-1-[N-(Thien-2-ylmethyl)-N-(4-phenoxybenzyl)-aminocarbonyl]cyclobutane-2,3,4-tricarboxylic acid;
- (1α,2β,3β,4α)-1-[N-Benzyl-N-(4-phenoxybenzyl)aminocarbonyl]-3-(methyloxycarbonyl)cyclobutane-2,4-dicarboxylic acid;
- (1α,2β,3β,4α)-1-[N-Benzyl-N-(4-phenoxybenzyl)aminocarbonyl]-4-(methyloxycarbonyl)cyclobutane-2,3-dicarboxylic acid;
- (1α,2β,3β,4α)-1-[N-Benzyl-N-(trans-3-phenyl-2-propenyl)-aminocarbonyl]cyclobutane-2,3,4-tricarboxylic acid;
- (−)-(1α,2β,3β,4α)-1-[N-Benzyl-N-(4-phenoxybenzyl)aminocarbonyl]-cyclobutane-2,3,4-tricarboxylic acid;
- (+)-(1α,2β,3β,4α)-1-[N-Benzyl-N-(4-phenoxybenzyl)aminocarbonyl]-cyclobutane-2,3,4-tricarboxylic acid;
- (1S,2R,3R,4R)-3-Methoxycarbonyl-4-[N-[(2S,3R)-4-(3,4-dichlorophenyl)-3-(2-naphthoyloxy)-2-butyl}aminocarbonyl]-cyclobutane-1,2-dicarboxylic acid;
- (1R,2S,3S,4S)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;
- (1S,2R,3R,4R)-4-[N-{(2S,3R)-4-(3,4-Dichlorophenyl)-3-(2-naphthoyloxy)-2-butyl}aminocarbonyl]cyclobutane-1,2,3-tricarboxylic acid;
- (1R,2S,3S,4S)-4-[N-{(2S,3R)-4-(3,4-Dichlorophenyl)-3-(2-naphthoyloxy)-2-butyl}aminocarbonyl]cyclobutane-1,2,3-tricarboxylic acid;
- (1S,2S,3S,4S)-3-Methoxycarbonyl-4-[N-{(2S,3R)-4-(3,4-dichlorophenyl)-3-(2-naphthoyloxy)-2-butyl}aminocarbonyl]cyclobutane-1,2-dicarboxylic acid;
- (1α,2α,3β,4β)-4-[N-{(2S,3R)-4-(4-chlorophenyl)-3-(4-biphenylyl)-2-butyl}aminocarbonyl]cyclobutane-1,2,3-tricarboxylic acid;
- (1α,2β,3β,4α)-2-Carbomethoxy-4-[N-{(1S,2R)-4-(3,4-dichlorophenyl)-3-(2-naphthoyloxy)-2-butyl}aminocarbony]cyclobutane-1,3-dicarboxylic acid;
- (1β,2α,3α4β)-2-Carbomethoxy-4-[N-{(1S,2R)-4-(3,4-dichlorophenyl)-3-(2-naphthoyloxy)-2-butyl}aminocarbony]cyclobutane-1,3-dicarboxylic acid;
- (1α,2β,3β)-3-[N-{(2S,3R)-4-(3,4-Dichlorophenyl)-3-(2-naphthoyloxy)-2-butyl}aminocarbony]cyclobutane-1,2-dicarboxylic acid;
- (1α,2β,3β)-3-[N-{2S,3R}-4-(3,4-Dichlorophenyl)-3-(2-naphthoyloxy)-2-butyl}aminocarbony]cyclobutane-1,2-dicarboxylic acid;
- (1β,2β,3α)-3-[N-{2S,3R}-4-(3,4-Dichlorophenyl)-3-(2-naphthoyloxy)-2-butyl}aminocarbony]cyclobutane-1,2-dicarboxylic acid;
- (1β,2α,3α)-3-[N-{(2S,3R)-4-(4-chlorophenyl)-3-(4-biphenylyl)-2-butyl}aminocarbonyl]cyclobutane-1,2-dicarboxylic acid;
- (1β,2β,3α,4α)-4-[N-Benzyl-N-(10-phenyldecyl)aminocarbonyl]cyclobutane-1,2,3-tricarboxylic acid;
- (1β,2β,3α,4α)-4-[N-Benzyl-N-(8-phenylocyl)aminocarbonyl]cyclobutane-1,2,3-tricarboxylic acid;
- 2-[N-{(2S,3R)-4-(4-Chlorophenyl)-3-(4-biphenylyl)-2-butyl}aminocarbonyl]-cyclobutane-1-carboxylic acid;
- (1β,2β,3α,4α)-4-[N-Benzyl-N-(4-(3-chlorophenoxy)benzyl)aminocarbonyl]-cyclobutane-1,2,3-tricarboxylic acid;
- (1β,2β,3α,4α)-4-[N-Benzyl-N-(2-chloro-4-(phenoxy)benzyl)aminocarbonyl]-cyclobutane-1,2,3-tricarboxylic acid;
- (1β,2β,3α,4α)-4-[N-Benzyl-N-(3-chloro-4-(phenoxy)benzyl)aminocarbonyl]-cyclobutane-1,2,3-tricarboxylic acid;
- (±)-(1α,2β,4α)-2-[N-{(2S,3R)-4-(4-Chlorophenyl)-3-(4-biphenylyl)-2-butyl}aminocarbonyl]-4-hydroxymethylcyclobutane-1-carboxylic acid;
- (1α,2β,3β,4α)-1-{N-Benzyl-N-[(4S*,5S*)-(4-acetoxy-5-methyl)-6-phenylhexyl]aminocarbonyl}cyclobutane-2,3,4-tricarboxylic acid;
- (1α,2β,3β,4α)-4-{N-Propyl-N-[(4S*,5S*)-(5-methyl-4-naphthoyloxy)-6-phenylhexyl]aminocarbonyl}cyclobutane-1,2,3-tricarboxylic acid;
- (1α,2α,3β,4β)-4-{N-Propyl-N-[(R)-6-methyl-9-phenyl-(E)-4-nonenyl]aminocarbonyl}cyclobutane-1,2,3-tricarboxylic acid;
- (1α,2α,3β,4β)-4-{N-Benzyl-N-[(R)-6-methyl-9-phenyl-(E)-4-nonenyl]aminocarbonyl}cyclobutane-1,2,3-tricarboxylic acid; and
- (1β,2α,3α,4β)-4-[N-{2S,3R}-4-(3,4-dichlorophenyl)-3-(2-naphthoyloxy)-2-butyl}aminocarbony]]cyclobutane-1,2,3-tricarboxylic acid; or a pharmaceutically acceptable salt thereof.

More preferred compounds are selected from the group consisting of:
- (1S,2R,3R,4R)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;
- (1R,2S,3S,4S)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;
- (1S,2R,3R,4R)-4-[N-{(2S,3R)-4-(3,4-Dichlorophenyl)-3-(2-naphthoyloxy)-2-butyl}aminocarbonyl]cyclobutane-1,2,3-tricarboxylic acid;
- (1R,2S,3S,4S)-4-[N-{(2S,3R)-4-(3,4-Dichlorophenyl)-3-(2-naphthoyloxy)-2-butyl}aminocarbonyl]cyclobutane-1,2,3-tricarboxylic acid;
- (1S,2S,3S,4S)-3-Methoxycarbonyl-4-[N-{(2S,3R)-4-(3,4-dichlorophenyl)-3-(2-naphthoyloxy)-2-butyl}aminocarbonyl]cyclobutane-1,2-dicarboxylic acid;
- (1α,2α,3β,4β)-4-[N-{(2S,3R)-4-(4-chlorophenyl)-3-(4-biphenylyl)-2-butyl}aminocarbonyl]cyclobutane-1,2,3-tricarboxylic acid;
- (1α,2β,3β,4α)-2-Carbomethoxy-4-[N-{(1S,2R)-4-(3,4-dichlorophenyl)-3-(2-naphthoyloxy)-2-butyl}aminocarbony]cyclobutane-1,3-dicarboxylic acid;
- (1β,2α,3α,4β)-2-Carbomethoxy-4-[N-{(1S,2R)-4-(3,4-dichlorophenyl)-3-(2-naphthoyloxy)-2-butyl}aminocarbony]cyclobutane-1,3-dicarboxylic acid;
- (1α,2β,3β)-3-[N-{(1S,2R)-4-(3,4-Dichlorophenyl)-3-(2-naphthoyloxy)-2-butyl}aminocarbony]cyclobutane-1,2-dicarboxylic acid;
- (1α,2β,3β)-3-[N-{1S,2R}-4-(3,4-Dichlorophenyl)-3-(2-naphthoyloxy)-2-butyl}aminocarbony]cyclobutane-1,2-dicarboxylic acid;
- (1β,2β,3α)-3-[N-{1S,2R}-4-(3,4-Dichlorophenyl)-3-(2-naphthoyloxy)-2-butyl}aminocarbony]cyclobutane-1,2-dicarboxylic acid;
- (1α,2β,3β,4α)-1-[N-Benzyl-N-{(4S*,5S*)-(4-hydroxy-5-methyl)-6-phenylhexyl}aminocarbonyl]cyclobutane-2,3,4-tricarboxylic acid;
- (1α,2β,3β,4α)-1-[N-Benzyl-N-(4-phenoxybenzyl)aminocarbonyl]-cyclobutane-2,3,4-tricarboxylic acid;

(1α,2β,3β,4α)-1-[N-(Thien-2-ylmethyl)-N-(4-phenoxybenzyl)-aminocarbonyl]cyclobutane-2,3,4-tricarboxylic acid;

(1α,2β,3β,4α)-1-[N-Benzyl-N-(4-phenoxybenzyl)aminocarbonyl]-3-(methyloxycarbonyl)cyclobutane-2,4-dicarboxylic acid;

(1α,2β,3β,4α)-1-[N-Benzyl-N-(4-phenoxybenzyl)aminocarbonyl]-4-(methyloxycarbonyl)cyclobutane-2,3-dicarboxylic acid;

(1α,2β,3β,4α)-1-[N-Benzyl-N-(trans-3-phenyl-2-propenyl)-aminocarbonyl]cyclobutane-2,3,4-tricarboxylic acid;

(−)-(1α,2β,3β,4α)-1-[N-Benzyl-N-(4-phenoxybenzyl)aminocarbonyl]-cyclobutane-2,3,4-tricarboxylic acid;

(+)-(1α,2β,3β,4α)-1-[N-Benzyl-N-(4-phenoxybenzyl)aminocarbonyl]-cyclobutane-2,3,4-tricarboxylic acid;

(1β,2,β,3α,4α)-4-[N-Benzyl-N-(3-chloro-4-(phenoxy)benzyl)aminocarbonyi]-cyclobutane-1,2,3-tricarboxylic acid; and (±)-(1α,2β,4α)-2-[N-{(2S,3R)-4-(4-Chlorophenyl)-3-(4-biphenylyi)-2-butyl}aminocarbonyl]-4-hydroxymethylcyclobutane-1-carboxylic acid; or a pharmaceutically acceptable salt thereof.

In general, the compounds of the invention can be prepared by the processes illustrated in Schemes I–V. According to reaction Scheme I 1,1,2,3,4-cyclobutanetetracarboxylic dianhydride (where the two anhydrides are trans to one another) in an inert solvent such as acetonitrile is treated with benzyl alcohol in the presence of an aprotic base such as triethylamine to afford the 1,2-diester (2b) and 1,3-diesters (2), respectively. (The isomeric diesters are separable by crystallization.) The dicarboxylic acids (2 and 2b) can be converted into their mono-amides 3 and 3b using HNR'R" (where R' and R" are $R_1$ and $R_2$ or $R_{41}$ and $R_{42}$ as defined previously herein) and typical peptide coupling conditions (for example, using dicyclohexylcarbodiimide and 1-hydroxybenzotriazole in DMF and $CH_2Cl_2$). Catalytic hydrogenation of 3 (for example, using a palladium on carbon catalyst in methanol) affords the tricarboxylic acid 4.

Alternatively Scheme II illustrates the reaction of 1,2,3,4-cyclobutanetetracarboxylic dianhydride (where the two anhydrides are trans to one another) with one equivalent of HNR'R" (where R' and R" are $R_1$ and $R_2$ or $R_{41}$ and $R_{42}$ as defined previously herein) in an inert solvent such as acetonitrile in the presence of an aprotic base such as diisopropylethylamine to give the mono-amide tricarboxylic acid 5. (This reaction can also be run with an excess of amine and then chromatographed to separate out the desired mono-amide.)

Scheme III illustrates the preparation of mono-amide, mono-ester compounds. The 1,3-mono-amide 3, whose preparation was illustrated in Scheme I, is esterified (for example, treatment with diazomethane in ether to give the methyl ester) to give compound 6. Catalytic hydrogenation of 6 (for example, using a palladium on carbon catalyst in methanol) affords the mono-amide, mono-ester, dicarboxylic acid 7. The 1,2-mono-amide 3b, whose preparation was also illustrated in Scheme I, can also be esterified to give compound 8. Catalytic hydrogenation of 8 (for example, using a palladium on carbon catalyst in methanol) affords the isomeric mono-amide, mono-ester, dicarboxylic acid 9.

Chiral compounds are prepared either by combining chiral intermediates or by induction of stereochemistry using a chiral compound such as norephedrine. One approach is shown in Scheme IV. The 1,2-dibenzyl ester 10, whose preparation (3b) was illustrated in Scheme I, is dissolved in a protic solvent such as ethanol and treated with 2 equivalents of (+)- or (−)-norephedrine to make the bis-ammonium carboxylate salt 11. The isomeric compounds are separated by crystallization and then acidified to give the chiral dicarboxylic acid 12. Treatment of compound 12 with one equivalent of HNR'R" (where R' and R" are $R_1$ and $R_2$ or $R_{41}$ and $R_{42}$ as defined previously herein) in an inert solvent such as DMF and $CH_2Cl_2$ under peptide coupling conditions (for example, EDCl hydrochloride and HOBt monohydrate) affords the chiral mono-amide 13. Catalytic hydrogenation of 13 affords the chiral tricarboxylic acid 14.

An alternate preparation of chiral compounds is shown in Scheme V. Racemic 1,2-dibenzyl ester 10, whose preparation (3b) was illustrated in Scheme I, is dissolved in an inert solvent such as $CH_2Cl_2$ and coupled with a chiral amine under standard peptide coupling conditions (for example, EDCl and HOBt in the presence of dimethylaminopyridine and triethylamine) to give chiral amide 15 (where $R_{12}$ is as previously defined herein). Compound 15 can be mono-esterified (for example, treatment with diazomethane give the methyl ester) to give compound 16. Compound 16 can be subjected to catalytic hydrogenation to give compound 17. The tricarboxylic acid 18 is obtained from compound 15 directly by catalytic hydrogenation.

SCHEME I

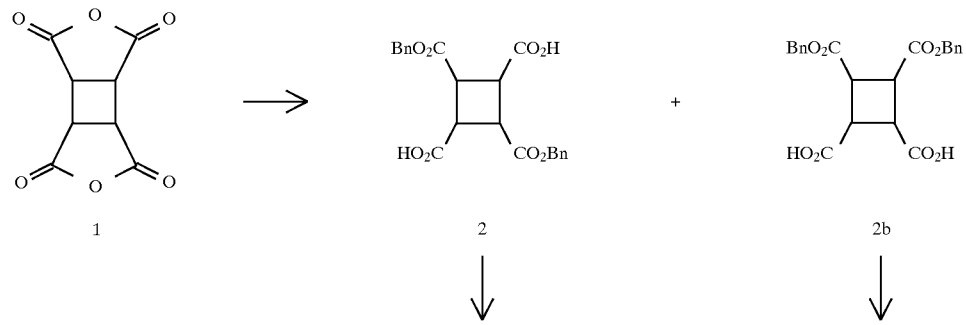

-continued
SCHEME I
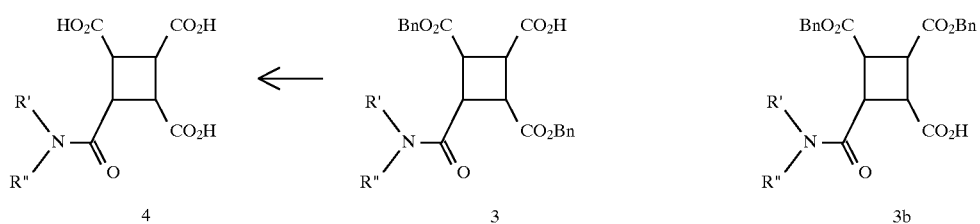
SCHEME II
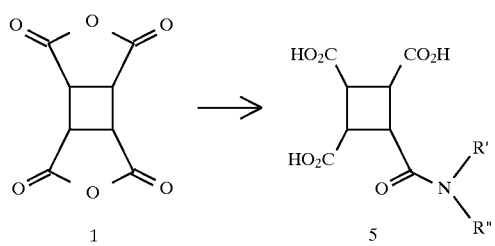
SCHEME III
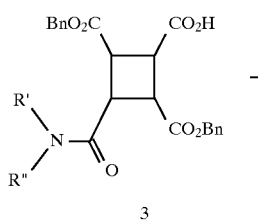
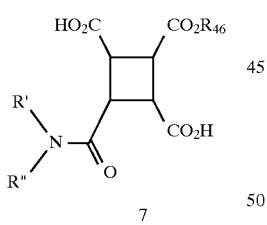
-continued
SCHEME III
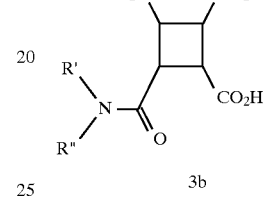
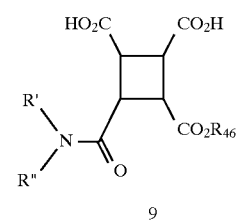

SCHEME IV
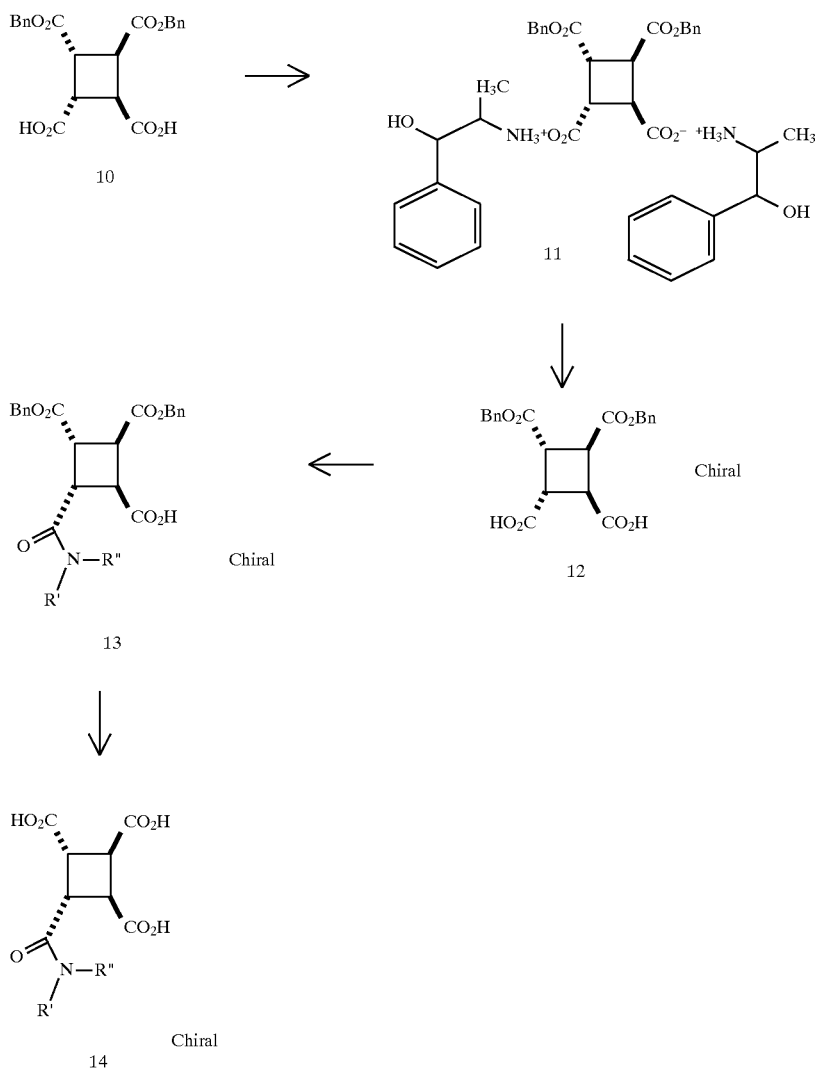
SCHEME V
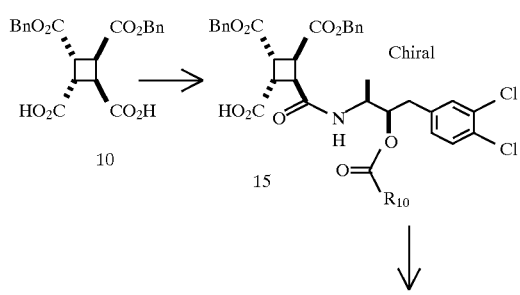

-continued
SCHEME V

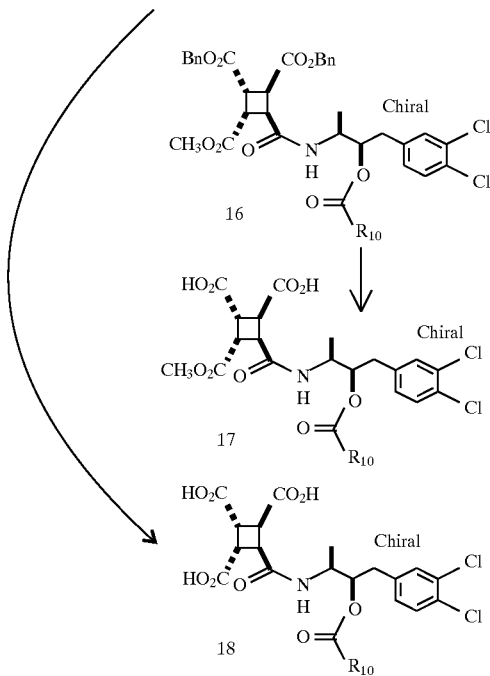

The foregoing may be better understood by reference to the following examples which are provided for illustration and not intended to limit the scope of the inventive concept. The following abbreviations are used: AIBN for azobisisobutyronitrile, n-BuLi for n-butyllithium, DBU for 1,8-diazabicyclo[5.4.0]undec-7-ene, DIBAL for diisobutylaluminun hydride, DMAP for dimethylaminopyridine, DMF for dimethylformamide, DMSO for dimethylsulfoxide, EDCl for 1-(3-dimethylaminopropyl)-3-ethylcarbodiimide hydrochloride, $Et_3N$ for triethylamine, EtOAc for ethyl acetate, EtOH for ethanol, HOAc or AcOH for acetic acid, HOBT for N-hydroxybenzotriazole hydrate, LAH for lithium aluminum hydride, MeOH for methanol, Pd/C for palladium on carbon, and THF for tetrahydrofuran.

EXAMPLE 1

(1α,2β,3β,4α)-1-[N-Benzyl-N-{(4S*,5S*)-(4-hydroxy-5-methyl)-6-phenylhexyl}aminocarbonyl] cyclobutane-2,3,4-tricarboxylic acid

EXAMPLE 1A (1S*,2S*)-(1-methyl-2-hydroxy)-5-benzyloxypentylphenyl ketone $TiCl_4$ (a 1.0M solution in $CH_2Cl_2$, 16.8 mL) was added dropwise to a −78° C. solution of propiophenone (2.05 g, 15.2 mmol) in 77 mL of $CH_2Cl_2$. After 5 minutes at −78° C., $NEt_3$ (2.3 mL, 16.8 mmol) was added, and the reaction mixture was stirred at −78° C. for 0.5 hour. 4-Benzyloxybutyraldehyde (3.0 g, 16.8 mmol), prepared by the procedure described in Heterocycles 28(2): 663, (1989), was added dropwise. The reaction mixture was stirred for 0.5 hours at −78° C. and then was quenched by the addition of 50% saturated $NH_4Cl$ solution. The solution was warmed to room temperature and extracted with $CH_2Cl_2$. The combined organic extracts were washed with saturated NaCl solution, dried over $MgSO_4$, filtered, and concentrated in vacuo. Purification by flash chromatography on silica gel eluting with 15:85 ethyl acetate in hexane afforded the title compound (3.67 g) as a clear oil. $^1H$ NMR (300MHz, $CDCl_3$)δ 1.28 (d, 3H), 1.60 (t,3H), 1.67–1.88 (m, 2H), 3.52 (m, 3H), 4.03 (m, 1H), 4.51 (s, 2H), 7.32 (s, 5H), 7.48 (t, 2H), 7.59 (t, 2H), 7.95 (d, 2H). MS (DCl/$NH_3$) m/e 313 $(M+H)^+$.

EXAMPLE 1B (1S*,2S*)-(1-methyl-2-acetoxy)-5-benzyloxypentylphenyl ketone

Acetic anhydride (1.1 mL, 11.7 mmol) was added dropwise to a 0° C. solution of the compound resulting from Example 1A and a catalytic amount of DMAP in 100 mL $CH_2Cl_2$. The reaction mixture was stirred for 24 hours at room temperature, then 0.1N HCl was added. The mixture was extracted with $CH_2Cl_2$ (3×). The combined organic layers were washed with saturated NaCl solution, dried ($MgSO_4$), filtered, and concentrated to afford the title compound (2.9 g) as a colorless oil. $^1H$ NMR (300 MHz, $CDCl_3$) δ 1.21 (d, 3H), 1.58–1.75 (m, 4H), 2.00 (s, 3H), 3.42 (t, 2H), 3.65 (m,1H), 4.46 (s, 2H), 5.30 (m, 1H), 7.30 (t, 5H), 7.47 (t, 2H), 7.58 (t, 1H), 7.90 (m, 2H). MS (DCl/$NH_3$) m/e 386 $(M+NH_4)^+$.

EXAMPLE 1C

Benzyl-[(4S*,5S*)-(4-acetoxy-5-methyl)-6-hydroxy-6-phenyl]hexyl ether

A solution of the compound resulting from Example 1B (0.5 g, 1.4 mmol), $CeCl_3 \cdot 7H_2O$, and 5 mL of MeOH was stirred at 0° C. as $NaBH_4$ (0.16 g, 4.2 mmol) was added portionwise. The reaction mixture was stirred at 0° C. for 0.25 hours, then 25 mL of 3N HCl was added (cautiously), followed by the addition of saturated NaCl solution. The solution was extracted with ether (3×). The combined organic layers were washed with saturated NaCl solution, dried (MgSO$_4$), filtered, and concentrated in vacuo to afford the title compound (0.5 g) as a colorless oil (as a mixture of diastereomeres). $^1$H NMR (300 MHz, CDCl$_3$) δ 0.60 (d, 1.5H), 0.97 (d, 1.5H), 1.57–1.74 (m, 4H), 1.85–1.98 (m, 1H), 2.02 (s, 1.5H), 2.15 ( s, 1.5H), 3.45 (t, 1H), 3.51 (m, 1H), 4.12 (dd, 0.5H), 4.50 (d, 2H), 4.75 (m, 0.5H), 4.90 (m, 0.5H), 5.43 (m, 0.5H), 7.32 (m, 10H). MS (DCl/NH$_3$) m/e 374 (M+NH$_4$)$^+$.

EXAMPLE 1D

Benzyl [(4S*,5S*)-(4-acetoxy-5-methyl)-6-trifluoroacetoxy-6-phenyl]hexyl ether

Trifluoroacetic anhydride (0.2 mL, 1.4 mmol) was added dropwise to a 0° C. solution of the compound resulting from Example 1C (0.5 g, 1.4 mmol), pyridine (0.11 mL), and 7 mL CH$_2$Cl$_2$. The reaction mixture was stirred at 0° C. for 4.5 hours then quenched with 0.1N HCl and extracted with CH$_2$Cl$_2$ (3×). The combined organic layers were washed with 0.1N HCl, dried (MgSO$_4$), filtered, and concentrated in vacuo to afford the title compound (0.59 g) as a colorless oil (as a mixture of diastereomeres). $^1$H NMR (300 MHz, CDCl$_3$) δ 0.78 (d, 1.5H), 1.10 (d, 1.5H), 1.50 (m, 1H), 1.64 (m, 2H), 1.78 (m, 1H), 2.02 (d, 3H), 2.32 (m, 1H), 3.39 (t, 1H), 3.50 (m, 2H), 4.98 (d, 2H), 4.67 (m, 0.5H), 5.29 (m, 0.5H), 5.52 (d, 0.5H), 5.78 (d, 0.5H), 7.30 (m, 10H). MS (DCl/NH$_3$) m/e 470 (M+NH$_4$)$^+$.

EXAMPLE 1E (4S*,5S*)-(4-Acetoxy-5-methyl)-6-phenyl-1-hexanol

A mixture of the compound resulting from Example 1D (0.59 g, 1.3 mmol), Pd/C (0.16 g, 10%, dry), and 50 mL of EtOAc was hydrogenated in a Parr shaker at room temperature for 39 hours. The mixture was filtered and concentrated in vacuo, and the residue was flash chromatographed on silica gel eluting with 8:2 hexane-EtOAc to afford the title compound (0.18 g) as a colorless oil. $^1$H NMR (300 MHz, CDCl$_3$) δ 0.89 (d, 3H), 1.45–1.60 (m, 3H), 1.69 (m, 2H), 2.00 (br s, 1H), 2.09 (s, 3H), 2.33 (dd, 1H), 2.77 (dd, 1H), 3.64 (t, 2H), 4.92 (m, 1H), 7.08–7.22 (m, 2H), 7.28 (m, 3H). MS (DCl/NH$_3$) m/e 268 (M+NH$_4$)$^+$.

EXAMPLE 1F

1-Iodo-(4S*,5S*)-(4-acetoxy-5-methyl)-6-phenylhexane

A solution of the compound resulting from Example 1E (0.33 g, 1.39 mmol) and 9.2 mL anhydrous CH$_3$CN was stirred at room temperature as the following were added sequentially: imidazole (0.24 g, 3.5 mmol), triphenylphosphine (0.40 g, 1.5 mmol), and iodine (0.39 g, 1.5 mmol). The reaction mixture was stirred at room temperature for 1.25 hours, then H$_2$O was added, and the mixture was extracted with CH$_2$Cl$_2$. The combined organic layers were washed with saturated sodium thiosulfate solution and saturated NaCl, dried (MgSO$_4$), filtered, and concentrated in vacuo to afford a white solid. The solid was triturated with hexane (3×), decanting after each. The hexane layers were combined, concentrated in vacuo, and the residue obtained flash chromatographed on silica gel eluting with 95:5 hexane-EtOAc to afford the title compound (0.38 g) as a colorless oil. $^1$H NMR (300 MHz, CDCl$_3$) δ 1.55 (s, 3H), 1.70 (t, 2H), 1.75–1.86 (m, 2H), 1.99 (m,1H), 2.09 (s, 3H), 2.34 (dd, 1H), 2.77 (dd, 1H), 3.20 (t, 2H), 4.90 (m, 1H), 7.10–7.22 (m, 3H), 7.28 (m, 2H). MS (DCl/NH$_3$) m/e 378 (M+NH$_4$)$^+$.

EXAMPLE 1G

N-(Benzyl)-N-(t-butyloxycarbonyl)-N-[((4S*,5S*)-4-acetoxy-5-methyl)-6-phenylhexyl]amine A solution of N-benzyl-N-t-butyloxycarbonylamine (0.22 g, 1.05 mmol), prepared by the method described in J. Heterocyclic Chem. 22(5): 1173, (1985), and 0.45 mL of anhydrous DMF was added dropwise to a 0° C. suspension of NaH (0.043 g 1.05 mmol, 60% dispersion, hexane washed) in 1.7 mL of anhyrous DMF. The sodium salt was formed for 0.5 hours at room temperature, then a solution of the compound resulting from Example 1F (0.38 g, 1.05 mmol) in 0.5 mL of anhydrous DMF was added dropwise. The reaction mixture was stirred for 2 days at room temperature. Ice water was added and the solution was extracted (3×) with ethyl acetate. The combined organic layers were washed with H$_2$O, cold 0.1N HCl and saturated NaCl solution, dried (MgSO$_4$), filtered, and concentrated in vacuo to afford the title compound (0.46 g) as a colorless oil. $^1$H NMR (300 MHz, CDCl$_3$) δ 0.82 (d, 3H), 1.39–1.57 (m, 13H), 1.92 (br s, 1H), 2.06 (s, 3H), 2.30 (dd, 1H), 2.72 (dd, 1H), 3.18 (br d, 2H), 4.29–4.49 (m, 2H), 4.85 (s, 1H), 7.10 (d, 2H), 7.19–7.38 (m, 8H). MS (DCl/NH$_3$) m/e 440 (M+H)$^+$, 457 (M+NH$_4$)$^+$.

EXAMPLE 1H

N-Benzyl-N-[((4S*,5S*)-4-acetoxy-5-methyl)-6-phenylhexyl]amine

Trifluoroacetic acid (7.7 mL) was added to a 0° C. solution of the compound resulting from Example 1G (0.46 g, 1.07 mmol) and 7.7 mL CH$_2$Cl$_2$. The reaction was stirred for 0.5 hours at 0° C. and for 1.5 hours at room temperature. The solvent was evaporated in vacuo. Toluene was added and evaporated in vacuo (2×). Amberlite resin (IRA-400-OH, 0.5 g, washed successively with H$_2$O, EtOH, ether, and dried) and 15 mL of CH$_2$Cl$_2$ was added and the suspension was stirred for 18 hours at room temperature. The suspension was filtered and concentrated in vacuo to afford the title compound (0.33 g) as a colorless oil. $^1$H NMR (300 MHz, CDCl$_3$) δ 0.85 (d, 3H), 1.58 (m, 4H), 1.95 (s,1H), 2.07 (s, 3H), 2.31 (m, 2H), 2.68 (s,1H), 2.74 (dd, 2H), 3.82 (s, 2H), 4.85 (m, 1H), 7.08–7.22 (m, 3H),7.28 (m, 3H), 7.37 (m, 4H). MS (DCl/NH$_3$) m/e 340 (M+H)$^+$.

EXAMPLE 1I (1α,2β,3β,4α)-1-[N-Benzyl-N-{(4S*,5S*)-(4-acetoxy-5-methyl)-6-phenylhexyl}aminocarbonyl]cyclobutane-2,3,4-tricarboxylic acid tribenzyl ester A solution of dicyclohexylcarbodiimide (0.19 g, 0.94 mmol) and 1.0 mL of DMF was added to a solution of (1α,2β,2β,4α)-cyclobutane tetracarboxylic acid-1,3-dibenzyl ester (0.39 g, 0.94 mmol), prepared from 1,2,3,4-cyclobutanetetracarboxylic dianhydride and benzyl alcohol following the procedures described in Angew. Chem. International Ed. 8: 208 (1969), the compound resulting from Example 1H (0.32 g, 0.94 mmol), 1-hydroxybenztriazole hydrate (0.13 g, 0.94 mmol), and 4.0 mL of DMF. The reaction mixture was stirred for 18 hours at room temperature and then diluted with EtOAc and filtered. The filtrate was washed with 1N HCl, H$_2$O and saturated aqueous NaCl solution, dried over MgSO$_4$, filtered and evaporated in vacuo to afford a yellow oil. Purification by flash chromatography on silica gel eluting with 97:2.5:0.5 CHCl$_3$—MeOH—HOAc to afford the title compound (0.19 g) as a colorless oil. $^1$H NMR (300 MHz, CDCl$_3$) δ 1.32–1.58 (m, 4H), 1.92 (m,1H), 2.05 (d, 3H), 2.30 (m, 1H), 2.39 (s, 3H), 2.70 (m,1H), 3.20 (m, 1H), 3.61–3.90 (m, 4H), 4.10 ( m, 2H), 5.15 (m, 4H), 7.10 (m, 3H), 7.19 (t, 6H), 7.30 (m, 11H). MS (FAB) m/e 734 (M+H)$^+$.

EXAMPLE 1J (1α,2β,3β,4α)-1-[N-Benzyl-N-{(4S*,5S*)-(4-hydroxy-5-methyl)-6-phenylhexyl}aminocarbonyl] cyclobutane-2,3,4-tricarboxylic acid A solution of the compound resulting from Example 1I (0.13 g, 0.18 mmol), 1.0M LiOH in H$_2$O (0.63 mL), and 2.0 mL THF was stirred at room temperature for 18 hours. 0.1N HCl was added and the solution was extracted (4×) with methylene chloride. The combined organic extracts were washed with saturated aqueous NaCl solution, dried over MgSO$_4$, filtered, and evaportated in vacuo to afford a white foam. The crude product was flash chromatographed on silica gel eluting with 94:5:1 CHCl$_3$—MeOH—acetic acid to afford the title compound (20 mg) as a white powder after lyophillization. $^1$H NMR (300 MHz, CD$_3$OD) δ 0.90 (d, 3H), 1.20 (m, 2H), 1.25 (m, 1H), 1.87 (m, 1H), 2.19 (m, 1H), 2.88 (m, 1H), 2.96–3.12 (m, 2H), 3.20 (m, 2H), 3.80–3.92 (m, 3H), 3.98–4.09 (m, 1H), 4.21 (m, 1H), 4.86–4.95 (m, 2H), 7.08 (d, 3H), 7.10–7.20 (m, 7H). MS (FAB) m/e 512 (M+H)$^+$.

EXAMPLE 2

(1α,2β,3β,4α)-1-[-N-Benzyl-N-{(4S*,5S*)-(4-acetoxy-5-methyl)-6-phenylhexyl}aminocarbonyl] cyclobutane-2,3,4-tricarboxylic acid A methanol solution of the compound resulting from Example 1I (60 mg, 0.08 mmol) was hydrogenated at atmospheric pressure at room temperature for 8 hours over palladium on carbon catalyst. The catalyst was removed by filtration and the solvent evaporated in vacuo. The crude product was flash chromatagraphed on silica gel eluting with 95:4:1 CHCl$_3$—MeOH—AcOH to afford 3.7 mg of the title compound as a white powder after lyophillization. $^1$H NMR (300 MHz, CD$_3$OD) δ 0.85 (d, 3H), 1.30 (m, 2H), 1.52 (m, 2H), 2.00 (m, 3H), 2.32 (m, 1H), 2.65 (m, 1H), 3.08 (m, 2H), 3.22 (m, 2H), 3.50–3.75 (m, 3H), 4.40 (m, 1H), 4.72 (s, 2H), 7.06–7.38 (m, 10H). MS (FAB+) m/e 554 (M+H)$^+$.

EXAMPLE 3

(1α,2β,3β,4α)-1-[N-Benzyl-N-(4-phenoxybenzyl) aminocarbonyl]-2,4-di(benzyloxycarbonyl) cyclobutane-3-carboxylic acid

EXAMPLE 3A

N-Benzyl-N-(4-phenoxybenzyl)amine

4-Phenoxybenzaldehyde (10.0 g, 0.05 mol), excess benzyl amine and 1.0 g of 10% Pd/C in 200 mL of ethanol were stirred under an inert atmosphere for 16 hours followed by an atmosphere of hydrogen for 16 hours. After removal of the catalyst by filtration through Celite®, the filtrate was concentrated under reduced pressure to give the crude product as an oil. The oil was dissolved in ether and precipitated by treatment with anhydrous HCl. The solid was filtered, washed with ether, and partitioned between ethyl acetate and 1M NaOH. The ethyl acetate solution was washed with brine, dried over Na$_2$SO$_4$, and evaporated to give the title compound.

EXAMPLE 3B (1α,2β,3β,4α)-1,3-Di(benzyloxycarbonyl) cyclobutane-2,4-dicarboxylic acid To a solution of 1,2,3,4-cyclobutanetetracarboxylic anhydride (21 g, 107.1 mmol) in acetonitrile (530 mL) at −7.5° C. was added benzyl alcohol (70 mL, 680 mmol) all at once. Triethylamine (30 mL, 210 mmol) was added dropwise over 3–5 minutes and the temperature rose to 2.8° C. Dimethylaminopyridine (1.3 g, 10.6 mmol) was added and the temperature returned to −5° C. The reaction mixture was stirred for 18 hours at which time the internal temperature was 9.2° C. and then concentrated in vacuo. The residue was dissolved in ethyl acetate (1 L) and washed with 2M HCl (2×375 mL). The product was then extracted into saturated NaHCO$_3$ solution (2 x 375 mL). The aqueous solution was allowed to stand at ambient temperature and then was cooled in a refrigerator overnight. The solid was collected and washed with cold saturated NaHCO$_3$ solution (200 mL). The combined NaHCO$_3$ filtrate and wash were acidified to pH 2 with concentrated HCl. The resulting white slurry was extracted with ethyl acetate (2×500 mL). The combined organic extracts were washed with 2×100 mL with 10% NaCl solution and dried over anhydrous sodium sulfate, filtered and concentrated in vacuo to afford a white solid. The solid was recrystallized from hot isopropanol to yield the title compound as a white solid. m.p. 179°–181° C.

EXAMPLE 3C (1α,2β,3β,4α)-1-[N-Benzyl-N-(4-phenoxybenzyl) aminocarbonyl]-2,4-di(benzyloxycarbonyl) cyclobutane-3-carboxylic acid The compound resulting from Example 3B (1.0 g, 2.42 mmol), dicyclohexylcarbodiimide (0.50 g, 2.42 mmol), and HOBt (0.37 g, 2.42 mmol) were dissolved in dimethylformamide (2 mL) and diluted with methylene chloride (50 mL). The compound resulting from Example 3A (0.70 g, 2.42 mmol) was added, and the mixture was stirred 18 hours at room temperature. The solution was concentrated in vacuo and partitioned between 1M HCl and ethyl acetate. The organic layer was washed with 1M HCl and brine, dried over Na$_2$SO$_4$, and concentrated under reduced pressure. The residue obtained was chromatographed on silica gel eluting with 50% ethyl acetate in hexane to give the title compound in 52% yield. $^1$H NMR (CDCl$_3$, 500 MHz) δ 3.75 (m, 1H), 3.84 (m, 1H), 4.13 (m, 1H), 4.35 (m, 2H), 4.66 (m, 2H), 4.93 (m, 1H), 5.14 (m, 3H), 5.68 (m, 1H), 6.90–7.54 (m, 24H). MS m/e 684 (M+H)$^+$.

EXAMPLE 4

(1α,2β,3β,4α)-1-[N-Benzyl-N-(4-phenoxybenzyl) aminocarbonyl]cyclobutane-2,3,4-tricarboxylic acid (1α,2β,3β,4α)-1-[N-Benzyl-N-(4-phenoxybenzyl) aminocarbonyl]-2,4-di(benzyloxycarbonyl)cyclobutane-3-carboxylic acid (0.20 g, 0.29 mmol) was dissolved in methanol and treated with 10% Pd/C (5 mg) under an atmosphere of hydrogen for 18 hours. Filtration through Celite® provided 80 mg (53%) of the triacid. $^1$H NMR (CDCl$_3$, 500 MHz) δ 3.48 (m, 4H), 3.92–5.04 (m, 4H), 6.9–7.38 (m, 14H). MS m/e 504 (M+H)$^+$.

EXAMPLE 5

(1α,2β,3β,4α)-1-[N-(Thien-2-ylmethyl)-N-(4-phenoxybenzyl)aminocarbonyl]-2,4-di(benzyloxycarbonyl)cyclobutane-3-carboxylic acid

EXAMPLE 5A

N-(Thien-2-yl)methyl-N-(4-phenoxy)benzylamine

A mixture of 4-phenoxybenzaldehyde (1.98 g, 10 mmol) and 2-thienylmethylamine (1.13 g, 10 mmol) in ethanol (10 mL) was stirred for 1 hour. Acetic acid (1 mL) and sodium cyanoborohydride (1M in THF, 10 mL) were added, and the reaction was stirred for 14 hours. The reaction was then partitioned between ether and 10% aqueous sodium hydroxide solution. The organic layer was further washed with water and brine, dried over anhydrous potassium carbonate, filtered and concentrated to give the title compound (2.87 g, 97%). $^1$H NMR (300 MHz, CDCl$_3$) δ 7.35–6.92 (m, 12H), 4.01 (s, 2H), 3.81 (s,2H).

EXAMPLE 5B (1α,2β,3β,4α)-1-[N-(Thien-2-ylmethyl)-N-(4-phenoxybenzyl)aminocarbonyl]-2,4-di(benzyloxycarbonyl)cyclobutane-3-carboxylic acid The title compound was prepared in 33% yield by the procedures described in Example 3 using the compound resulting from Example 5A. $^1$H NMR (CDCl$_3$, 500 MHz) δ 3.5–5.2 (m, 12H), 6.6–7.4 (m, 22H). MS m/e 690 (M+H)$^+$.

EXAMPLE 6

(1α,2β,3β,4α)-1-[N-(Thien-2-ylmethyl)-N-(4-phenoxybenzyl)aminocarbonyl]cyclobutane-2,3,4-tricarboxylic acid The title compound (117.5 mg, 80%) was prepared by the method described in Example 4 starting with the compound resulting from Example 5. $^1$H NMR (DMSO-d$_6$, 500 MHz) δ 3.5–3.65 (m, 1H), 3.85 (m, 1H), 4.02 (m, 1H), 4.10 (m, 1H), 4.33–4.90 (m, 4H), 6.90–7.48 (m, 12H), 12.5 (bs, 3H). MS m/e 510 (M+H)$^+$.

EXAMPLE 7

(1α,2β,3β,4α)-1-[N-Benzyl-N-(4-phenoxybenzyl)aminocarbonyl]-2,4-di(benzyloxycarbonyl)-3-(methyloxycarbonyl)cyclobutane The compound resulting from Example 3 (50.4 mg, 73.7 μmol) was dissolved in methanol and treated with an excess of ethereal diazomethane, prepared by adding 1-methyl-3-nitro-1-nitrosoguanidine to a mixture of 40% potassium hydroxide and ether and decanting the ether solution of diazomethane. The solution was evaporated to dryness to give the title compound in quantitative yield. $^1$H NMR (CDCl$_3$, 500 MHz) δ 3.53 (d, 3H, J=5 Hz), 3.72 (m, 1H), 3.91 (m, 1H), 4.04 (m, 2H), 4.37 (m, 3H), 4.58 (m, 1H), 4.92 (m, 1H), 5.11 (m, 3H), 6.83–7.39 (m, 24H). MS m/e 698 (M+H)$^+$.

EXAMPLE 8

(1α,2β,3β,4α)-1-[N-Benzyl-N-(4-phenoxybenzyl)aminocarbonyl]-3-(methyloxycarbonyl)cyclobutane-2,4-dicarboxylic acid The compound resulting from Example 7 (50 mg, 0.07 mmol) was converted to the title compound (29 mg, 78%) by the method described in Example 4. $^1$H NMR (CDCl$_3$, 500 MHz) δ 3.42 (m, 1H), 3.73 (d, 3H, J=4 Hz), 3.92 (m, 1H), 3.99 (m, 1H), 4.13 (m, 1H), 4.3 (m, 2H), 4.52 (m, 1H), 4.90 (d, 1H, J=9 Hz), 6.92–7.38 (m, 14H). MS m/e 518 (M+H)$^+$.

EXAMPLE 9

(1α,2β,3β,4α)-1-[N-Benzyl-N-(4-phenoxybenzyl)aminocarbonyl]-3,4-di(benzyloxycarbonyl)cyclobutane-2-carboxylic acid

EXAMPLE 9A (1α,2β,3β,4α)-1,2-Di(benzyloxycarbonyl)cyclobutane-3,4-dicarboxylic acid To a solution of 1,2,3,4-cyclobutanetetracarboxylic anhydride (21 g, 107.1 mmol) in acetonitrile (530 mL) at −7.5° C. was added benzyl alcohol (70 mL, 680 mmol) all at once. Triethylamine (30 mL, 210 mmol) was added dropwise over 3–5 minutes and the temperature rose to 2.8° C. Dimethylaminopyridine (1.3 g, 10.6 mmol) was added and the temperature returned to −5° C. The reaction mixture was stirred for 18 hours at which time the internal temperature was 9.2° C. and then concentrated in vacuo. The residue was dissolved in ethyl acetate (1 L) and washed with 2M HCl (2×375 mL). The product was then extracted into saturated NaHCO$_3$ solution (2×375 mL). The aqueous solution was allowed to stand at ambient temperature and then was cooled in a refrigerator overnight. The solid was collected and washed with cold saturated NaHCO$_3$ solution (200 mL) and then was dissolved in water (500 mL), acidified with 2M HCl (375 mL) and extracted into ethyl acetate (2×375 mL). The combined organic extracts were washed with brine, dried over sodium sulfate and concentrated in vacuo to afford the title compound (25.65 g, 58%) as a white solid. m.p. 164.5°–165.5° C.

EXAMPLE 9B (1α,2β,3β,4α)-1-[N-Benzyl-N-(4-phenoxybenzyl)aminocarbonyl]-3,4-di(benzyloxycarbonyl)cyclobutane-2-carboxylic acid The title compound was prepared in 44% yield by the method described in Example 3 using the compound resulting from Example 9A. $^1$H NMR (CD$_3$OD, 500 MHz) δ 3.45 (m, 1H), 3.59 (m, 1H), 3.76 (m, 1H), 3.93 (m, 1H), 4.42 (m, 4H), 5.05 (m, 4H), 6.92–7.38 (m, 24H). MS m/e 684 (M+H)$^+$.

EXAMPLE 10

(1α,2β,3β,4α)-1-[N-Benzyl-N-(4-phenoxybenzyl)aminocarbonyl]-4-(methyloxycarbonyl)cyclobutane-2,3-dicarboxylic acid The compound resulting from Example 4 (100 mg, 0.2 mmol) was dissolved in methylene chloride (10 mL) with enough DMF to bring the suspension into solution. A solution of dicyclohexylcarbodiimide (41 mg, 0.2 mmol) in methylene chloride (5 mL) was added. After stirring at room temperature for 1 hour, diazomethane in ether was added dropwise until the yellow color persisted. The reaction mixture was stripped to dryness and dissolved in ethyl acetate. The solution was stirred with water 18 hours before washing the organic layer with water and brine, drying over Na$_2$SO$_4$, and concentrating in vacuo. The residue obtained was chromatographed on silica gel eluting with 98:1:1 ethyl acetate-formic acid-water to give 20 mg (20%) of pure title compound. $^1$H NMR (DMSO-d$_6$, 500 MHz) δ 3.44 (d, 3H, J=4 Hz), 3.69 (m, 2H), 3.92 (m, 2H), 4.70 (m, 3H), 5.54 (d, 1H, J=5 Hz), 6.92–7.40 (m, 14H), 12.53 (bs, 2H). MS m/e 518 (M+H)$^+$.

EXAMPLE 11

(1α,2β,3β,4α)-1-[N-Benzyl-N-(4-phenoxybenzyl) aminocarbonyl]-2,3-di(methoxycarbonyl)-4-(diphenylmethyloxycarbonyl)cyclobutane The compound resulting from Example 4 (0.5 g, 0.99 mmol) was dissolved in methylene chloride (250 mL) with enough dimethylformamide to bring the suspension into solution. A solution of dicyclohexylcarbodiimide (0.2 g, 0.99 mmol) in methylene chloride (10 mL) was added. After stirring at room temperature for 1 hour, diphenyldiazomethane (0.19 g, 0.99 mmol, prepared by stirring benzophenone hydrazone and mercury (II) oxide in hexane for 18 hours, filtering, and evaporating to dryness, was added. After 2 hours at room temperature, water was added, and the mixture was stirred for 18 hours. The layers were separated, and the aqueous phase was extracted with methylene chloride. The combined organic extracts were treated with excess ethereal diazomethane. After 30 minutes, the solution was evaporated to dryness and the product purified by chromatography on silica gel eluting with 20 to 50% ethyl acetate in hexane to give 153 mg (22%) of the pure title compound. $^1$H NMR (DMSO-d$_6$, 500 MHz) δ 3.68 (m, 6H), 3.82 (m, 2H), 3.95–4.50 (m, 7H) 6.83–7.38 (m, 24H). MS m/e 698 (M+H)$^+$.

EXAMPLE 12

(1α,2β,3β,4α)-1-[N-Benzyl-N-(4-phenoxybenzyl) aminocarbonyl]-2,3-di(methoxycarbonyl) cyclobutane-4-carboxylic acid The compound resulting from Example 11 (130 mg, 0.19 mmol) was hydrogenated using the procedures described in Example 4 to give the title compound (65 mg, 66%). $^1$H NMR (DMSO-d$_6$, 500 MHz) 3.54 (m, 3H), 3.59 (m, 3H), 3.71 (m, 2H), 3.90–4.38 (m, 4H), 4.8 (M, 2H), 6.89–7.41 (m, 14H). MS m/e 532 (M+H)$^+$.

EXAMPLE 13

(1α,2β,3β,4α)-1-[N-Benzyl-N-(4-phenoxybenzyl) aminocarbonyl]-2-(methyloxycarbonyl)cyclobutane-3,4-dicarboxylic acid

EXAMPLE 13A (1α,2β,3β,4α)-1-[N-Benzyl-N-(4-phenoxybenzyl) aminocarbonyl]-2-(methyloxycarbonyl)-3,4-di(benzyloxycarbonyl)cyclobutane The title compound was prepared in 75% yield by the procedure described in Example 7 using the compound resulting from Example 9.

EXAMPLE 13B (1α,2β,3β,4α)-1-[N-Benzyl-N-(4-phenoxybenzyl) aminocarbonyl]-2-(methyloxycarbonyl)cyclobutane-3,4-dicarboxylic acid The compound resulting from Example 13A (75 mg, 0.11 mmol) was converted to the title compound in 71% yield using the method described in Example 4. $^1$H NMR (DMSO-d$_6$, 500 MHz) δ 3.48 (m, 3H), 3.71 (m, 2H), 3.9–4.9 (m, 5H), 5.57 (d, 1H, J=5 Hz), 6.86–7.41 (m, 14H). MS m/e 518 (M+H)$^+$.

EXAMPLE 14

Alternate Preparation of (1α,2β,3β,4α)-1-[N-Benzyl-N-(4-phenoxybenzyl)aminocarbonyl] cyclobutane-2,3,4-tricarboxylic acid A solution of 1,2,3,4-cyclobutanetetracarboxylic dianhydride (0.86 g, 4.4 mmol) in 40 mL of acetone and 10 mL of acetonitrile was cooled in a salt-ice bath. This solution was then treated with a solution of the compound resulting from Example 3A (1.3 g, 4.4 mmol) and diisopropylethyl amine (0.57 g , 4.4 mmol) dissolved in 10 mL of acetone dropwise over 5 hrs. via syringe pump. After stirring an additional hour in the cooling bath, the reaction mixture was warmed to ambient temperature and evaporated under reduced pressure. To the residue was added 6N HCl (90 mL) and methylene chloride (10 mL), and the mixture was stirred at room temperature for 1 hour. The solid which formed was then filtered off. Flash silica gel chromatography eluting with with 95:4:1 CHCl$_3$—MeOH—HOAc yielded 1.9 g (85.8%) of the title compound. $^1$H NMR (DMSO-d$_6$, 500 MHz) δ 3.50 (m, 4H), 4.00–4.90 (m, 4H), 6.85–7.45 (m, 14H). MS (FAB)$^+$m/e 504 (M+H)$^+$and (FAB)$^-$m/e 502 (M–H)$^-$.

EXAMPLE 15

(1α,2β,3β,4α)-1-[N-Benzyl-N-(trans-3-phenyl-2-propenyl)aminocarbonyl]cyclobutane-2,3,4-tricarboxylic acid

EXAMPLE 15A

N-Benzyl-N-(trans-3-phenyl-2-propenyl)amine

Cinnamaldehyde and benzylamine were dissolved in 1% acetic acid in methanol under an atmosphere of dry nitrogen. Sodium cyanoborohydride (~1 equivalent) was added, and stirring was continued for 18 hours at which time the solvent was removed under reduced pressure. The residue was suspended in ether, washed with 5% NaHCO$_3$ and brine, dried over Na$_2$SO$_4$ and concentrated in vacuo to afford the title compound.

EXAMPLE 15B (1α,2β,3β,4α)-1-[N-Benzyl-N-(trans-3-phenyl-2-propenyl)aminocarbonyl]cyclobutane-2,3,4-tricarboxylic acid To a slurry of 1,2,3,4-cyclobutanetetracarboxylic dianhydride (0.5 g, 2.5 mmol) in CH$_3$CN (10 mL) was added the compound resulting from Example 15A (2.23 g, 10 mmol) in CH$_3$CN (10 mL). The slurry was stirred for 5 minutes at 20° C., resulting in a homogenous solution. The solution was stirred 20 hours at 20° C., then concentrated in vacuo to a white foam. The foam was dissolved in 100 mL ethyl acetate and washed successively with 50 mL of 1N H$_3$PO$_4$ and 10% NaCl, dried over anhydrous sodium sulfate, filtered and concentrated in vacuo to afford 3.2 g of a white foamy solid. The crude product was purified by silica gel chromatography eluting with 94:5:1 CHCl$_3$—MeOH—HOAc. The slowest moving product was isolated using a methanol wash and repurified on silica gel eluting with 38:1:1 EtOAc—

HCO$_2$H—H$_2$O to give the title compound in 12% yield. $^1$H NMR (CDCl$_3$,300 MHz) δ 7.4–7.15 (m, 10), 6.52–6.45 (m, 2H), 4.49–4.12 (m, 6H), 3.94–3.77 (m, 2H). MS (FAB$^+$) m/e 438, (FAB$^-$) 436.

EXAMPLE 16

(1α,2β,3β,4α)-1-[N-Benzyl-N-(trans,trans-5-phenyl-2,4-pentadienyl)aminocarbonyl]cyclobutane-2,3,4-tricarboxylic acid

EXAMPLE 16A

N-Benzyl-N-(trans,trans-5-phenyl-2,4-pentadienyl) amine

Benzylamine (1 g, 9.3 mmole) and vinyl triphenylphosphonium bromide (3.45 g, 9,3 mmole) are treated with 20 mL CH$_3$CN and the resulting slurry is heated for 36 hours at 40° C. and refluxed 5 hours. The reaction mixture is cooled to room temperature and the solvent removed in vacuo. The solid is treated with 20 mL THF, and the resulting slurry is treated with 17 mL 2.0M BuLi in cyclohexane. The red anion solution is stirred 30 minutes at room temperature then cinnamaldehyde (10 mmol) is added, and the resulting suspension is stirred 18 hours at room temperature. The reaction mixture is quenched with 20 mL 5% HCl followed by extraction with ethyl ether (2×50 mL). The aqueous layer is adjusted to pH 10 with 1N NaOH and extracted with CH$_2$Cl$_2$ (2×50 mL). The combined organic extracts are washed with 10% NaCl, dried over anhydrous sodium sulfate, filtered and concentrated in vacuo to afford the title compound.

EXAMPLE 16B (1α,2β,3β,4α)-1-[N-Benzyl-N-(trans,trans-5-phenyl-2,4-pentadienyl)aminocarbonyl]cyclobutane-2,3,4-tricarboxylic acid The title compound is prepared using the compound resulting from Example 16A and the procedures described in Example 15B.

EXAMPLE 17

(1α,2β,3β,4α)-1-[N-Benzyl-N-(cis-4-benzyloxy-2-butenyl)aminocarbonyl]cyclobutane-2,3,4-tricarboxylic acid

EXAMPLE 17A

1-Benzyloxy-cis-2-butene-1,4-diol

Cis-2-Butene-1,4 diol (10 g, 0.113 mol) was dissolved in THF (50 mL) and added to a slurry containing THF (100 mL) and NaH (5.9 g, 0.246 mol, 60% dispersion). The mixture was stirred 15 minutes then benzyl bromide (14.8 mL, 0.124 mole) was added and the mixture was stirred 1.5 hours at room temperature then refluxed 3 hours and finally cooled to room temperature. The reaction mixture was quenched with 20 mL water and concentrated in vacuo to an orange oil. The oil was dissolved in ethyl acetate (100 mL), washed with 10% NaCl (50 mL), dried over anhydrous sodium sulfate, filtered and concentrated in vacuo to afford 15 g of the title compound as a yellow oil.

EXAMPLE 17B

4-Benzyloxy-cis-2-butene-1-carboxaldehyde

The compound resulting from Example 17A in THF is added dropwise to a −70° C. solution containing oxalyl chloride, DMSO and methylene chloride. After addition, the mixture is stirred 45 minutes at −70° C., then added dropwise, maintaining the internal temperature below −50° C., triethylamine in methylene chloride. The mixture is then warmed to 0° C. and 10% citric acid is added. The layers are separated and the organic layer is washed with 10% sodium bicarbonate and 10% sodium chloride, dried over anhydrous magnesium sulfate, filtered and concentrated in vacuo to afford the title compound.

EXAMPLE 17C

N-(4-Benzyloxy-cis-2-butenyl)-N-benzyl amine

The amine is prepared by the reductive amination procedure described in Example 3A from the compound resulting from Example 17B and benzyl amine.

EXAMPLE 17D (1α,2β,3β,4α)-1-[N-Benzyl-N-(4-Benzyloxy-cis-2-butenyl)aminocarbonyl]cyclobutane-2,3,4-tricarboxylic acid The title compound is prepaired using the compound resulting from Example 17C and the procedures described in Example 15B.

EXAMPLE 18

(1α,2β,3β,4α)-1-[N-Benzyl-N-(4-phenoxy-cis-2-butenyl)aminocarbonyl]cyclobutane-2,3,4-tricarboxylic acid

EXAMPLE 18A 1-tert-Butyl dimethylsiloxy-cis-2-butene-1,4-diol

Cis-2-Butene-1,4 diol (10 g, 0.113 mol) was dissolved in 200 mL CH$_2$Cl$_2$ and treated with tert-butyldimethyl silyl chloride (17.9 g, 0.119 mol), triethylamine (18.8 mL, 0.135 mol) and a catalytic amount of N,N-dimethylaminopyridine. The resulting solution was stirred 2 days at room temperature then filtered. The organic layer was washed with distilled water (2×100 mL) and 10% NaCl (2×100 mL), dried over anhydrous magnesium sulfate, filtered and concentrated in vacuo to afford 16.4 g of the title compound as a clear oil.

EXAMPLE 18B

1-Bromo-cis-2-butene-4-tert-butyl dimethylsilyl ether

The compound resulting from Example 18A in acetonitrile is added to a solution containing lithium bromide and trimethylsilyl chloride in acetonitrile. The reaction mixture is stirred at reflux for 2 hours then cooled to room temperature. Water is added to the reaction mixture, and the solvent is removed in vacuo. The residue is extracted with ether (2×50 mL). The combined organic extracts are washed with 10% sodium bicarbonate solution and brine, dried over anhydrous sodium sulfate, filtered and concentrated in vacuo to afford the title compound.

EXAMPLE 18C

1-Phenoxy-cis-2-butene-4-tert-butyl dimethylsilyl ether

The compound resulting from Example 18B is dissolved in DMF and treated with sodium phenoxide in DMF. The resulting mixture is heated at 80° C. for 6 hours then cooled to room temperature and diluted with a mixture of water (20 mL) and ethyl acetate (200 mL). The layers are separated, and the organic layer is washed with saturated sodium bicarbonate and brine, dried over anhydrous sodium sulfate, filtered, and concentrated in vacuo to afford the title compound.

EXAMPLE 18D

4-Phenoxy-cis-2-butene-1-carboxaldehyde

The compound resulting from Example 18C is treated with a THF solution of tetrabutyl ammonium fluoride (TBAF) and stirred 3 hours at room temperature. The solvent is removed in vacuo. The crude alcohol is oxidized to the aldehyde using the same procedure described in Example 17B.

EXAMPLE 18E

N-(4-Phenoxy-cis-2-butenyl)-N-benzyl amine

The amine is prepared by the reductive amination procedure described in Example 3A from the compound resulting from Example 18D and benzyl amine.

EXAMPLE 18F (1α,2β,3β,4α)-1-[N-Benzyl-N-(4-phenoxy-cis-2-butenyl)aminocarbonyl]cyclobutane-2,3,4-tricarboxylic acid The title compound is prepared using the compound resulting from Example 18E and the procedures described in Example 15B.

EXAMPLE 19

(−)-(1α,2β,3β,4α)-1-[N-Benzyl-N-(4-phenoxybenzyl)aminocarbonyl]cyclobutane-2,3,4-tricarboxylic acid

EXAMPLE 19A (+)-(1α,2β,3β,4α)-1,2-Di[benzyloxycarbonyl]cyclobutane-3,4-dicarboxylic acid To a solution of 1,2,3,4-cyclobutanetetracarboxylic anhydride (21 g, 107.1 mmol) in acetonitrile (530 mL) at −7.5° C. was added benzyl alcohol (70 mL, 680 mmol) all at once. Triethylamine (30 mL, 210 mmol) was added dropwise over 3–5 minutes and the temperature rose to 2.8° C. Dimethylaminopyridine (1.3 g, 10.6 mmol) was added and the temperature returned to −5° C. The reaction mixture was stirred for 18 hours at which time the internal temperature was 9.2° C. and then concentrated in vacuo. The residue was dissolved in ethyl acetate (1 L) and washed with 2M HCl (2×375 mL). The product was then extracted into saturated $NaHCO_3$ solution (2×375 mL). The aqueous solution was allowed to stand at ambient temperature and then was cooled in a refrigerator overnight. The solid was collected and washed with cold saturated $NaHCO_3$ solution (200 mL) and then was dissolved in water (500 mL), acidified with 2M HCl (375 mL) and extracted into ethyl acetate (2×375 mL). The combined organic extracts were washed with brine, dried over sodium sulfate and concentrated in vacuo to afford (1α,2β,3β,4α)-1,2-di(benzyloxycarbonyl) cyclobutane-3,4-dicarboxylic acid (25.65 g, 58%) as a white solid. m.p. 164.5°–165.5° C.

To the above prepared compound (1.0 g, 2.4 mmol) dissoved in absolute EtOH (45 mL) was added a solution of (−)-norephedrine (0.74 g, 4.9 mmol) in absolute EtOH (5 mL). The solution was allowed to sit at room temperature overnight. The resultant crystals were filtered and then recrystallized twice from hot absolute EtOH (4.5 mg/mL), then partitioned between 1M $H_3PO_4$ and $Et_2O$. The $Et_2O$ layer was washed with brine, dried over $Na_2SO_4$, filtered and concentrated to give the title compound. $[\alpha]_D$=+17.3° (c=0.92, MeOH).

EXAMPLE 19B (−)-(1α,2β,3β,4α)-1-[N-Benzyl-N-(4-phenoxybenzyl)aminocarbonyl]cyclobutane-2,3,4-tricarboxylic acid To the compound resulting from Example 19A (214 mg, 0.52 mmol) dissolved in DMF (1.5 mL) was added a solution of N-benzyl-N-(4-phenoxybenzyi)amine (148 mg, 0.53 mmol) in $CH_2Cl_2$ (0.5 mL). After cooling to 0° C., $HOBT.H_2O$ (78 mg, 0.51 mmol) and EDCl.HCl (103 mg, 0.54 mmol) were added. The reaction was allowed to warm to room temperature overnight then diluted with EtOAc (20 mL) and washed 2× with saturated $NaHCO_3$, 3× with 1M $H_3PO_4$ and brine. The organic layer was dried over $Na_2SO_4$, filtered, and concentrated to a residue that was purified by chromatography eluting with 1:1 ethyl acetate-hexane followed by 97.5:2.5 $CHCl_3$—MeOH to afford 50 mg (14%) of solid material.

This material was dissolved in EtOAc (3 mL) and treated with 10% Pd/C (12 mg). This slurry was stirred under a hydrogen balloon for 3.5 hours, then filtered through celite and concentrated. The residue was dissolved in $CH_3CN$, triturated with water and lyophilized to give the title compound (30 mg) as a white solid. $^1H$ NMR (DMSO-$d_6$) δ 7.45–7.20, 7.17, 7.00, 6.92 (envelope, m, m, m, total 14H), 4.82, 4.70 (both m, total 2H), 4.25, 4.10 (both m, 2H), 3.82 (m, 1H), 3.55 (m, 3H). MS (FAB$^-$) m/e 502 (M−H)$^-$. $[\alpha]_D$=−60.4° (c=0.695, 3:1 MeOH—$H_2O$).

EXAMPLE 20

(+)-(1α,2β,3β,4α)-[N-Benzyl-N-(4-phenoxybenzyl) aminocarbonyl]cyclobutane-2,3,4-tricarboxylic acid The first EtOH filtrate from Example 19A was concentrated, acidified, and treated with two equivalents of (+)-norephedrine. The resultant crystals were purified by the method of Example 25A to give the (−)-diacid.

The diacid was converted to the title compound by the method of Example 25B. $^1H$ NMR (DMSO-$d_6$) δ 7.45–7.20, 7.17, 7.00, 6.92 (envelope, m, m, m, total 14H), 4.82, 4.70 (both m, total 2H), 4.25, 4.10 (both m, 2H), 3.82 (m, 1H), 3.55 (m, 3H). MS (FAB$^-$) m/e 502 (M−H)$^-$. Anal. calcd for $C_{28}H_{25}NO_8$.1.4 $H_2O$: C, 63.61; H, 5.30; N, 2.65. Found: C, 63.21; H, 4.84; N, 2.76. $[\alpha]_D$=+57.4° (c=0.725, 3:1 MeOH—$H_2O$).

EXAMPLES 21 and 22

(1S,2S,3S,4S)-2,3-Di(benzyloxycarbonyl)-4-[N-{(2S,3R)-4-(3,4-dichlorophenyl)-3-(2-naphthoyloxy)-2-butyl}aminocarbonyl]cyclobutane-1-carboxylic acid (21) and (1R,2R,3R,4R)-2,3-Di(benzyloxycarbonyl)-4-[N-}(2S,3R)-4-(3,4-dichlorophenyl-3-(2-naphthoyloxy)-2-butyl}-aminocarbonyl]cyclobutane-1-carboxylic acid (22)

To a suspension of (2S,3R)-4-(3,4-dichlorophenyl)-3-(2-naphthoyloxy)-2-butylamine hydrochloride (106.2 mg, 0.250 mmol), prepared by the procedures described in European Patent Application EP 611749, published Aug. 24, 1994, and incorporated herein by reference, the compound resulting from Example 9A (110.6 mg, 0.275 mmol) in methylene chloride (20 mL) and THF (3 mL) was added 1-ethyl-3-(3-dimethylaminopropyl)carbodiimide hydrochloride (EDC.HCl, 74.0 mg, 0.375 mmol), triethylamine (0.10 mL, 0.725 mmol), 4-dimethylaminopyridine (15 mg). The reaction was stirred overnight. Ethyl acetate (40 mL) was added to the reaction mixture, and the resulting mixture was washed with 0.2M HCl (10 mL), potassium dihydrogenphosphate (half saturated, 10 mL) and brine (10 mL), dried over magnesium sulfate, filtered and concentrated in vacuo. The crude product was purified by chromatography eluting with 1:1 hexane-ethyl acetate (50 mL), ethyl acetate (100 mL) and 3% methanol in ethyl acetate to give Example 22 as the first fraction (76.1 mg, 39%) and Example 21 as the second fraction (89.5 mg, 46%). Example 21: $^1$H NMR(300 MHz, CDCl$_3$) δ 8.45–7.20 (20H), 5.40 (1H), 5.20–4.96 (4H), 4.27 (2H), 3.95–3.60 (4H), 3.02–2.85 (3H), 1.10 (3H); MS (FAB+) m/e 782 [$^{35}$Cl, M+H]. Example 22: $^1$H NMR (300 MHz, CDCl$_3$) δ 8.43–7.05 (20H), 5.32–4.96 (5H), 4.30 (1H), 3.90–3.60 (4H), 3.43 (1H), 2.94 (3H), 1.17 (3H); MS (FAB+) m/e 782 [$^{35}$Cl, M+H].

EXAMPLE 23

(1S,2R,3S,4R)-3-Methoxycarbonyl-4-[N-{(2S,3R)-4-(3,4-dichlorophenyl)-3-(2-naphthoyloxy)-2-butyl}-aminocarbonyl]cyclobutane-1,2-dicarboxylic acid To a 0° C. solution of the compound resulting from Example 21 (29.1 mg, 0.037 mmol) in 1:1 methanol-ether (4 mL) was added (trimethylsilyl)diazomethane (2.0M in hexane, 1 mL). The solvent was evaporated, and to the residue was added 10% palladium on activated carbon (20 mg) and ethanol (3 mL). A hydrogen ballon was then attached to the reaction vessel, which was flushed with hydrogen three times and then stirred under a hydrogen atmosphere. After 10 hours, the reaction mixture was filtered through celite and concentrated to give the title compound (13.7 mg, 60%). $^1$H NMR (500 MHz, CD$_3$OD) δ 8.58 (s, 1H), 8.03 (d, 1H), 7.95 (dt, 1H), 7.92 (d, 2H), 7.63 (dt, 1H), 7.58 (dt, 1H), 7.49 (d, 1H), 7.31 (d, 1H), 7.22 (dd, 1H), 5.30 (m, 1H), 4.26 (m, 1H), 3.89 (m, 1H), 3.70 (s, 3H), 3.72–3.60 (m, 3H), 3.18 (m, 1H), 3.04 (m, 1H), 1.26 (d, 3H). MS (FAB$^+$) m/e 616 [$^{35}$Cl, M+H]$^+$.

EXAMPLE 24

(1R,2S,3R,4S)-3-Methoxycarbonyl-4-[N-{(2S,3R)-4-(3,4-dichlorophenyl)-3-2-naphthoyloxy)-2-butyl}-aminocarbonyl]cyclobutane-1,2-dicarboxylic acid To a 0° C. solution of the compound resulting from Example 22 (32.1 mg, 0.041 mmol) in 1:1 methanol-ether (4 mL) was added (trimethylsilyl)diazomethane (2.0M in hexane, 1 mL). The solvent was evaporated, and to the residue was added 10% palladium on activated carbon (20 mg) and ethanol (3 mL). A hydrogen ballon was then attached to the reaction vessel, which was flushed with hydrogen three times and then stirred under a hydrogen atmosphere. After 10 hours, the reaction mixture was filtered through celite and concentrated to give the title compound (17.4 mg, 69%). $^1$H NMR (500 MHz, CD$_3$OD) δ 8.54 (1H), 8.04–7.91 (m, 4H), 7.65–7.53 (m, 2H), 7.33–7.12 (m, 4H), 5.30 (m, 1H), 4.24 (m, 1H), 3.89 (m, 1H), 3.61 (s, 3H), 3.72–3.55 (m, 3H), 3.3 (m, 2H), 1.31 (2 d's, 3H). MS (FAB$^-$) m/e 614 [$^{35}$Cl, M–H]$^+$.

EXAMPLE 25

(1S,2S,3S,4R)-4-[N-{(2S,3R)-4-(3,4-Dichlorophenyl)-3-(2-naphthoyloxy)-2-butyl}aminocarbonyl]cyclobutane-1,2,3-tricarboxylic acid A suspension of the compound resulting from Example 21 (22.9 mg, 0.029 mmol) and palladium (10%) on activated carbon (10 mg) in ethanol (3 mL) was flushed with nitrogen, then hydrogen. A hydrogen ballon was then attached to the reaction mixture, and it was stirred for 10 hours. The mixture was then filtered through celite and concentrated to give the title compound (12.8 mg, 73%). $^1$H NMR (500 MHz, CD$_3$OD) δ 8.58 (s, 1H), 8.03 (d, 1H), 7.95 (dt, 1H), 7.92 (d, 2H), 7.63 (dt, 1H), 7.58 (dt, 1H), 7.47 (d, 1H), 7.33 (d, 1H), 7.21 (dd, 1H), 5.30 (m, 1H), 4.26 (m, 1H), 3.90 (m, 1H), 3.74–3.60 (m, 3H), 3.18 (m, 1H), 3.03 (m, 1H), 1.26 (d, 3H). MS (FAB$^+$) m/e 602 [$^{35}$Cl, M+H]$^+$.

EXAMPLE 26

(1R,2R,3R,4S)-4-[N-{(2S,3R)-4-(3,4-Dichlorophenyl)-3-(2-naphthoyloxy)-2-butyl}aminocarbonyl]cyclobutane-1,2,3-tricarboxylic acid A suspension of the compound resulting from Example 22 (23.0 mg, 0.029 mmol) and palladium (10%) on activated carbon (10 mg) in ethanol (3 mL) was flushed with nitrogen, then hydrogen. A hydrogen ballon was then attached to the reaction mixture, and it was stirred for 10 hours. The mixture was then filtered through celite, and concentrated to give the title compound (9.5 mg, 54%). $^1$H NMR (500 MHz, CD$_3$OD) δ 8.54 (1H), 8.06–7.91 (m, 4H), 7.65–7.56 (m, 2H), 7.35–7.10 (m, 4H), 5.27 (m, 1H), 4.25 (m, 1H), 3.90 (m, 1H), 3.72–3.55 (m, 3H), 3.3 (m, 2H), 1.31 (d, 3H). MS (FAB$^+$) m/e 602 [$^{35}$Cl, M+H]$^+$.

EXAMPLE 27

(1S,2S,3S,4S)-3-Methoxycarbonyl-4-[N-{(2S,3R)-4-(3,4-dichlorophenyl)-3-(2-naphthoyloxy)-2-butyl}-aminocarbonyl]cyclobutane-1,2-dicarboxylic acid To a suspension of (1S,2R)-3-(3,4-dichlorophenyl)-1-methyl-2-(2-naphthoyloxy)propylamine hydrochloride (42.5 mg, 0.10 mmol), prepared by the procedures described in European Patent Application EP 611749, published Aug. 24, 1994, and incorporated herein by reference, 1,2,3,4-cyclobutanetetracarboxylic dianhydride (100 mg, 0.50 mmol) in 1:1 etheracetonitrile (10 mL) at −78° C. was added triethylamine (15 mg, 0.15 mmol). The reaction mixture was allowed to warm to 22° C. overnight and then cooled with an ice-water bath. Diazomethane in ether was added to it until the solution remained slightly yellow. Formic acid (0.5 mL) was added immediately, followed by ethyl acetate (60 mL) and water (5 mL). The organic layer was washed with water (5 mL) and brine (5 mL), dried over anhydrous magnesium sulfate, filtered, and concentrated. The crude product was purified with column chromatography eluting with ethyl acetate (80 mL), followed by 95:5:1 ethyl acetate-methanol-formic acid to give the title compound (51.3 mg). The proton NMR showed about a 1:1 ratio of rotomers. $^1$H NMR (300 MHz, DMSO-D$_6$) δ 8.59, 8.55 (s, 1H), 8.37, 8.27 (d, 1H), 8.16–7.89 (m, 4H), 7.70–7.45 (m, 3H), 7.25 (t, 1H), 5.33 & 5.19 (m, 1H), 4.10 (m, 1H), 3.62 (s, 3H), 3.57–3.45 (m, 3H), 3.35 (m, 1H), 3.08 (m, 1H), 2.97 (m, 1H), 1.09, 1.07 (s, 3H). MS (FAB$^+$) m/e 616 [$^{35}$Cl, M+H]$^+$.

EXAMPLE 28

Alternate Preparation of (1S,2S,3S,4S)-2,3-Di (benzyloxycarbonyl)-4-[N-{(2S,3R)-4-(3,4-dichlorophenyl)-3-(2-naphthoyloxy)-2-butyl}aminocarbony]cyclobutane-1-carboxylic acid To a suspension of (1S,2R)-3-(3,4-dichlorophenyl)-1-methyl-2-(2-naphthoyloxy)propylamine hydrochloride (9 mg, 0.022 mmol) and the compound resulting from Example 19A (10 mg, 0.024 mmol) in methylene chloride (1 mL) and THF (1 mL) was added 1-ethyl-3-(3-dimethylaminopropyl) carbodiimide hydrochloride (EDC HCl, 4.8 mg, 0.024 mmol), triethylamine (1 drop), 4-dimethylaminopyridine (1 mg). The reaction was stirred overnight. The reaction was worked up by the procedures described in Example 19 to give the title compound.

EXAMPLE 29

(1α,2α,3α,4α)-4-[N-{(2S,3R)-4-(4-chlorophenyl)-3-(4-biphenylyl)-2-butyl}aminocarbonyl]cyclobutane-1,2,3-tricarboxylic acid The compound resulting from Example 28A (300 mg, 0.728 mmol) in 50 mL of methylene chloride was treated with 2 mL of oxalyl chloride. After 3 hours all volatiles were removed under reduced pressure. The resulting oil was dissolved in 50 mL of methylene chloride, to which was added 271 mg (0.728 mmol) of (1RS,2SR)-2-(4-biphenylyl)-3-(4-chlorophenyl)-1-methylpropylamine hydrochloride, prepared by the procedures described in Example 114 of European Patent Application EP 611749, published Aug. 24, 1994, and incorporated herein by reference, to form a slurry. The mixture was cooled to 0° C., whereupon 197 mg (1.53 mmol) of N,N-diisopropylethylamine in 10 mL of methylene dichloride was added dropwise. After 24 hours all volatiles were removed under reduced pressure. The resulting oil was dissolved in 50 mL of methylene dichloride, and the solution was washed with dilute HCl. The organic phase was dried ($MgSO_4$) and all volatiles were removed under reduced pressure.

To the resulting oil dissolved in 10 mL of ethanol was added 20 mg of 10% Pd/C, and an atmosphere of hydrogen was introduced. The mixture was stirred for 24 hours. The mixture was filtered, and all volatiles were removed under reduced pressure. The resulting oil was purified by flash column chromatography on silica gel, first eluting with 5:1 hexane-EtOAc, then with 2:1 hexane-EtOAc, and finally with 1800:1:1 EtOAc—$HCO_2H$—$H_2O$ to give 25 mg (33%) of the title compound. $^1H$ NMR ($CDCl_3$, 300 MHz) δ 0.93 and 0.96 (two doublets, J=6 Hz, 3H), 2.7–3.0 (m, 2H), 3.3–3.5 (m, 1H), 3.5–3.9 (m, 4H), 4.1–4.3 (m, 1H), 6.9–7.6 (m, 13H). MS ($FAB^+$) m/e 550 $(M+H)^+$.

EXAMPLE 30

(1α,2β,3β,4α)-2-Carbomethoxy-4-[N-{(2S,3R)-4-(3,4-dichlorophenyl)-3-(2-naphthoyloxy)-2-butyl}-aminocarbony]cyclobutane-1,3-dicarboxylic acid and (1β,2α,3α,4β)-2-Carbomethoxy-4-[N-{(2S,3R)-4-(3,4-dichlorophenyl)-3-(2-naphthoyloxy)-2-butyl}aminocarbony]cyclobutane-1,3-dicarboxylic acid

EXAMPLE 30A

Dibenzyl (1α,2β,3β,4α)-2-Carbomethoxy-4-[N-{(2S,3R)-4-(3,4-dichlorophenyl)-3-(2-naphthoyloxy)-2-butyl}aminocarbony]cyclobutane-1,3-dicarboxylate and Dibenzyl (1β,2α,3α,4β)-2-Carbomethoxy-4-[N-{(2S,3R)-4-(3,4-dichlorophenyl)-3-(2-naphthoyloxy)-2-butyl}aminocarbony]cyclobutane-1,3-dicarboxylate To a mixture of the compound resulting from Example 9A (351 mg, 0.85 mmol), (2S,3R)-4-(3,4-dichlorophenyl)-3-(2-naphthoyloxy)-2-butylamine hydrochloride (90.5 mg, 0.21 mmol), 1-ethyl-3-(3-dimethylaminopropyl)carbodiimide hydrochloride (EDC HCl, 82 mg, 0.42 mmol) at −78° C. was added THF (10 mL), dichloromethane (10 mL), and triethylamine (0.12 mL, 0.85 mmol). The reaction was left to warm to 25° C. overnight and then partitioned between ethyl acetate (80 mL) and 10% HCl (aqueous, 15 mL). The organic layer was washed with water (15 mL×2), saturated potassium dihydrophosphate (10 mL), and brine (10 mL), dried over anhydrous magnesium sulfate, filtered, and concentrated in vacuo. The residue was then dissolved in 1:1 dichloromethane-methanol (5 mL), and an excess amount of (trimethylsilyl)diazomethane (2.0M in hexane, 2 mL) was added. The resulting green-yellow solution was concentrated in vacuo, and the residue was purified with silica gel column chromatography eluting with ethyl acetate and 2% methanol in ethyl acetate to give the title compound (137.5 mg, 81%) as a diastereomeric mixture (1:1 ratio, based on $^1H$ NMR). $^1H$ NMR ($CDCl_3$, 300 MHz) δ 8.52 (2 br s's, 1H), 7.96 (m, 2H), 7.87 (m. 2H), 7.59 (m, 2H), 7.39–7.22 (m, 11H), 7.18 (m, 1H), 7.09 (2 t's, 1H), 6.51, 6.39 (2 br d's, 1H), 5.40, 5.28 (2 m's, 1H), 5.25–4.75 (m, 4H), 4.25 (m, 1H), 3.98–3.47 (m, 4H), 3.46, 3.45 (2 s's, 3H), 2.95 (m, 2H), 1.22 & 1.19 (2 d's, 3H).

EXAMPLE 30B (1α,2β,3β,4α)-2-Carbomethoxy-4-[N-{(2S,3R)-4-(3,4-dichlorophenyl)-3-(2-naphthoyloxy)-2-butyl}-aminocarbony]cyclobutane-1,3-dicarboxylic acid and (1β,2α,3α,4β)-2-Carbomethoxy-4-[N-{(2S,3R)-4-(3,4-dichlorophenyl)-3-(2-naphthoyloxy)-2-butyl}-aminocarbony]cyclobutane-1,3-dicarboxylic acid A suspension of the mixture resulting from Example 30A (113 mg, 0.14 mmol) and 10% palladium on carbon (50 mg) in ethanol (5 mL) was hydrogenated using a hydrogen balloon source for 5 hours. The reaction mixture was then filtered through celite and concentrated. The residue was purified by column chromatography eluting with 1:1 chloroform-ethyl acetate, followed by 50:50:5:1 chloroform-ethyl acetate-methanol-formic acid to give the title compounds as a diastereomeric mixture (ratio~1:1, 71.3 mg, 82%). $^1H$ NMR (DMSO-$d_6$, 500 MHz) δ 2.8–12.2 (br s, 2H), 8.59, 8.56 (2 s's, 1H), 8.37, 8.25 (2 br d's, 1H), 8.10 (dd, 1H), 8.02 (m, 2H), 7.93 (dt, 1H), 7.67 (t, 1H), 7.62 (dt, 1H), 7.55 (t, 1H), 7.45 (dd, 1H), 7.25 (dt, 1H), 5.33 & 5.17 (2 m's 1H), 4.12 (m, 1H), 3.60, 3.59 (2 s's, 3H), 3.70–3.34 (m, 4H), 3.14, 3.08 (2 dd's, 1H), 2.94 (m, 1H), 1.18, 1.13 (2 d's, 3H). MS (FAB+) m/e 616 [$^{35}$Cl, $M+H$]$^+$.

EXAMPLE 31

(1α,2β,3β)-3-[N-{(2S,3R)-4-(3,4-Dichlorophenyl)-3-(2-naphthoyloxy)-2-butyl}aminocarbony] cyclobutane-1,2-dicarboxylic acid

EXAMPLE 31A (±)-(1α,2β,3β,4α)-1,2-Di(benzyloxycarbonyl)-4-[(2-trimethylsilylethyloxy)carbonyl]cyclobutane-3-carboxylic acid A solution of the compound resulting from Example 28A (3.53 g, 8.56 mmol), 1-ethyl-3-(3-dimethylaminopropyl)-carbodiimide hydrochloride (EDC HCl, 1.50 g, 7.84 mmol) and triethylamine (1.2 mL, 8.6 mmol) in 1:1 dichloromethane-THF (170 mL) was stirred for 15 minutes and then cooled to 0° C. To this reaction mixture was added trimethylsilylethyl alcohol (1.02 mL, 7.13 mmol), followed by 4-dimethylaminopyridine (30 mg). The reaction mixture was stirred 3 hours and partitioned between ethyl acetate (150 mL) and 10% HCl (50 mL). The organic phase was washed with water and brine, dried over anhydrous magnesium sulfate, filtered, and concentrated. The residue was then purified by column chromatography eluted with 30% ethyl acetate-hexane and ethyl acetate to give the title compound (2.69 g, 61%). $^1$H NMR (CDCl$_3$, 300 MHz) δ 7.40–7.28 (m, 10H), 5.13 (s, 4H), 4.05 (m, 2H), 3.80 (m, 4H), 0.89 (t, 2H), 0.02 (s, 9H).

EXAMPLE 31 B

Dibenzyl (2β,3β,4α)-1-iodo-4-[(2-trimethylsilylethyloxy)carbonyl]cyclobutane-2,3-dicarboxylate A solution of the compound resulting from Example 31A (3.95 g, 7.71 mmol), iodobenzene diacetate (6.20 g, 19.3 mmol) and iodine (5.87 g, 23.1 mmol) in carbon tetrachloride (200 mL) was deoxygenated with nitrogen and then irradiated with a 500 watt halogen lamp. The reaction was refluxed from the heat generated from the irradiation. After 20 hours, the reaction was cooled and filtered through a thick layer of silica gel (about 100 g), and washed with ether. The residue after concentration of the filtrate was purified by column chromatography eluted sequentially with 5%, 10%, 15%, and 20% ethyl acetate in hexane, to give two products (α- and β-iodides), which were combined to give the title compound (3.45 g, 75%). $^1$H NMR (CDCl$_3$, 300 MHz) of the less polar diastereomer δ 7.45–7.30 (m, 10H), 5.24 (d, 1H), 5.20 (d, 1H), 5.11 (s, 2H), 5.02 (dd, 2H), 4.15–3.96 (m, 3H), 3.79 (m, 2H), 0.92 (t, 2H), 0.03 (s, 9H). $^1$H NMR (CDCl$_3$, 300 MHz) of the more polar diastereomer δ 7.45–7.30 (m, 10H), 5.23–5.07 (m, 4H), 4.65 (m, 1H), 4.25–4.10 (m, 3H), 3.60 (m, 2H), 0.98 (m, 2H), 0.03 (s, 9H).

EXAMPLE 31C

Dibenzyl (1α,2β,3β)-3-[(2-trimethylsilylethyloxy)carbonyl]cyclobutane-1,2-dicarboxylate A solution of the compound resulting from Example 31B (3.45 g, 5.81 mmol), tributyltin hydride (3.1 mL, 11.6 mmol) and AIBN (20 mg) in toluene (20 mL) was heated at 90° C. for 6 hours. The solvent was evaporated in vacuo, and the residue was dissolved in ether (40 mL). To this well stirred solution was added water (0.1 mL), followed by DBU (2 mL). The resulting milky mixture was filtered through silica gel (30 g) and washed with ether. The residue resulting from concentration of the filtrate was purified by column chromatography eluted sequentially with hexane, 5%, 10%, 15% ethyl acetate in hexane to give the title compound as a sticky oil, which solidified on standing at 25° C. (1.75 g, 74%). $^1$H NMR (CDCl$_3$, 300 MHz) δ 7.34 (m, 10H), 5.15 (s, 2H), 5.10 (s, 2H), 4.05 (m, 2H), 3.75 (m, 2H), 3.35 (m, 1H), 2.43 (m, 2H), 0.89 (t, 2H), 0.02 (s, 9H).

EXAMPLE 31D (1α,2β,3β)-1,2-Di(benzyloxycarbonyl)cyclobutane-3-carboxylic acid A solution of the compound resulting from Example 31C (300 mg, 0.64 mmol) and tetrabutylammonium fluoride monohydrate (335 mg, 1.28 mmol) in DMF (6 mL) was stirred at room temperature for 3 hours. The reaction mixture was then diluted with ethyl acetate (80 mL) and washed with 1% HCl (15 mL), water (15 mL), 1M potassium dihydrophosphate (15 mL), and brine (15 mL), dried over anhydrous magnesium sulfate, filtered, and concentrated. The residue was then purified by column chromatography eluted with 30% ethyl acetate in hexane, followed by 100% ethyl acetate to give the title compound (193 mg, 82%). $^1$H NMR (CDCl$_3$, 300 MHz) δ 7.34 (m, 10H), 5.14 (m, 4H), 3.77 (m, 2H), 3.42 (m, 2H), 2.48 m (2H).

EXAMPLE 31E

Dibenzyl (1β,2α,3α)-3-[N-{2S,3R}-4-(3,4-dichlorophenyl)-3-(2-naphthoyloxy)-2-butyl}aminocarbonyl]cyclobutane-1,2-dicarboxylate (i) and Dibenzyl (1α,2β,3β)-3-[N-{2S,3R}-4-(3,4-dichlorophenyl)-3-(2-naphthoyloxy)-2butyl}-aminocarbonyl]cyclobutane-1,2-dicarboxylate (ii)

To a solution of the compound resulting from Example 31D (82.5 mg, 0.224 mmol) in dichloromethane (5 mL) was added oxalyl chloride (2.0M in dichloromethane, 0.5 mL), followed by a small drop of 1:4 DMF-dichloromethane. After 10 minutes, the reaction solvent was evaporated using a stream of nitrogen, and the residue was placed under vacuum (2 mm Hg) for 15 minutes. The acid chloride was re-dissolved in dichloromethane (5 mL) and was cooled to 0° C. To this solution was added (2S,3R)-4-( 3,4-dichlorophenyl)-3-(2-naphthoyloxy)-2-butylamine hydrochloride (104.7, 0.246 mmol), followed by triethylamine (0.093 mL, 0.67 mmol) and 4-dimethylaminopyridine (5 mg). After 30 minutes at 25° C., the reaction mixture was filtered through silica gel, washed with ethyl acetate, and the filtrate was concentrated in vacuo. The residue obtained was purified by column chromatography eluted with 30% ethyl acetate in hexane to give 31E(i) as the first fraction (53.5 mg, 32%), and compound 31E(ii) as the second fraction (62.3 mg, 37%). $^1$H NMR (CDCl$_3$, 300 MHz) of compound 31E(i) δ 8.51 (s, 1H), 7.96 (m, 2H), 7.90 (m, 2H), 7.59 (m, 2H), 7.40–7.26 (m, 12H), 7.11 (dd, 1H), 5.85 (d, 1H), 5.48 (m, 1H), 5.12 (s, 2H), 5.12 (d, 1H), 5.08 (d, 1H), 4.26 (m, 1H), 3.92 (q, 1H), 3.68 (m, 1H), 3.14–2.90 (m, 3H), 2.52 (m, 1H), 2.33 (m, 1H), 1.17 (d, 3H). $^1$H NMR (CDCl$_3$, 300 MHz) of compound 31E(ii) δ 8.51 (s, 1H), 7.97 (m, 2H), 7.89 (m, 2H), 7.60 (m, 2H), 7.40–7.26 (m, 12H), 7.09 (dd, 1H), 6.10 (d, 1H), 5.24 (m, 1H), 5.17–5.02 (m, 4H), 4.29 (m, 1H), 3.91 (m, 1H), 3.72 (m, 1H), 3.19 (m, 1H), 3.00 (m, 2H), 2.48–2.30 (m, 2H), 1.24 (d, 3H).

EXAMPLE 31F (1β,2α,3α)-3-[N-{2S,3R}-4-(3,4-Dichlorophenyl)-3-(2-naphthoyloxy)-2-butyl}aminocarbonyl]cyclobutane-1,2-dicarboxylic acid A suspension of the compound resulting from Example 31E(i) (52.6 mg, 0.071 mmol) and palladium (10%) on carbon (50 mg) in DMF (5 mL) was hydrogenated using a hydrogen balloon source for 1 hour. The reaction mixture was then filtered through celite, washed with 4:1 ethyl acetate-methanol, and the filtrate concentrated. The residue was diluted to 45 mL with ethyl acetate and was washed with 1% HCl (10 mL), potassium dihydrophosphate (saturated, 10 mL), water and brine, dried over anhydrous magnesium sulfate, filtered, and concentrated in vacuo. The residue was then purified by column chromatography eluted with 5% methanol in ethyl acetate followed by 50:50:5:1 chloroform-ethyl acetate-methanol-formic acid to give the title diacid (34 mg, 81%). $^1$H NMR (DMSO-d$_6$, 500 MHz) δ 8.59 (s, 1H), 8.25 (m, 2H), 8.01 (m, 2H), 7.93 (m, 1H), 7.68 (m, 1H), 7.62 (m, 1H), 7.25 (dd, 1H), 7.21 (m, 1H), 5.18 (m, 1H), 4.13 (m, 1H), 3.51–3.10 (m, 4H), 2.95 (m, 1H), 2.15 (m, 2H), 1.10 (d, 3H). MS (FAB+) m/e 558 [$^{35}$Cl, M+H]$^+$.

EXAMPLE 32

(1α,2β,3β)-3-[N-{2S,3R}-4-(3,4-Dichlorophenyl)-3-(2-naphthoyloxy)-2-butyl}aminocarbonyl] cyclobutane-1,2-dicarboxylic acid The compound resulting from Example 31E(ii) (61.3 mg, 0.083 mmol) was reacted by the procedures described in Example 31F to give the title compound (45.0 mg, 97%). $^1$H NMR (DMSO-d$_6$, 500 MHz) δ 8.56 (s, 1H), 8.11 (m, 2H), 8.01 (m, 2H), 7.92 (m, 1H), 7.67 (m, 1H), 7.62 (m, 1H), 7.24 (m, 2H), 5.36 (m, 1H), 4.12 (m, 1H), 3.51–3.10 (m, 3H), 3.10–2.95 (m, 2H), 2.12 (m, 2H), 1.04 (d, 3H). MS (FAB+) m/e 558 [$^{35}$Cl, M+H]$^+$.

EXAMPLE 33

(1β,2β,3α)-3-[N-{2S,3R}-4-(3,4-Dichlorophenyl)-3-(2-naphthoyloxy)-2-butyl}aminocarbonyl] cyclobutane-1,2-dicarboxylic acid

EXAMPLE 33A (1β,2α,3α)-1-[(2-Trimethylsilylethyloxy)carbonyl] cyclobutane-2,3-dicarboxylic acid A suspension of the compound resulting from Example 31C (104 mg, 0.26 mmol) and 10% palladium on carbon (100 mg) in ethanol (5 mL) was hydgogenated using a hydrogen balloon source for 15 hours. The reaction mixture was then filtered through celite and concentrated in vacuo to give the title compound (76 mg, 100%). $^1$H NMR (DMSO-d$_6$, 300 MHz) δ 4.07 (m, 2H), 3.50–3.25 (m, 3H), 2.23 (m, 2H), 0.91 (m, 2H), 0.03 (s, 9H).

EXAMPLE 33B (1β,2α,3α)-3-[N-{2S,3R}-4-(3,4-Dichlorophenyl)-3-(2-naphthoyloxy)-2-butyl}aminocarbonyl]-1-[(2-trimethylsilylethyloxy)carbonyl]cyclobutane-2-carboxylic acid A solution of the compound resulting from Example 33A (64.2 mg, 0.223 mol), 1-ethyl-3-(3-dimethylaminopropyl)-carbodiimide hydrochloride (EDC HCl, 43 mg, 0.223 mmol) and triethylamine (0.046 mL, 0.31 mmol) in 1:1 dichloromethane-THF (170 mL) was stirred for 15 minutes and then was cooled to –20° C. To this solution was added (2S,3R)-4-(3,4-dichlorophenyl)-3-(2-naphthoyloxy)-2-butylamine hydrochloride (80 mg, 0.19 mmol) followed 4-dimethylaminopyridine (4 mg). The reaction was gradually warmed to room temperature over 15 hours. The reaction mixture was then diluted with ethyl acetate (80 mL), and was washed with 1% HCl (10 mL), water (10 mL) and brine, dried over anhydrous magnesium sulfate, filtered, and concentrated. The residue was then purified by column chromatography eluted sequentially with 1:1 hexane-ethyl acetate, 100% ethyl acetate and 5% methanol in ethyl acetate to give first fraction as the mixture of both diastereomers of diamide and a second fraction as the title compound (34.1 mg, 23%). $^1$H NMR (CDCl$_3$, 300 MHz) δ 8.49 (s, 1H), 7.95 (m, 2H), 7.87 (m, 2H), 7.59 (m, 2H), 7.37 (d, 1H), 7.32 (dd, 1H), 7.11 (dd, 1H), 5.52 (m, 1H), 4.28 (m, 1H), 4.17 (m, 2H), 3.65 (m, 1H), 3.46 (m, 1H), 3.23 (m, 1H), 2.99 (m, 2H), 2.57 (m, 1H), 2.10 (m, 1H), 1.32 (d, 3H), 0.96 (m, 2H), 0.03 (s, 9H).

EXAMPLE 33C (1β,2β,3α)-3-[N-{2S,3R}-4-(3,4-Dichlorophenyl)-3-(2-naphthoyloxy)-2-butyl}aminocarbonyl] cyclobutane-1,2-dicarboxylic acid A solution of the compound resulting from Example 13B (39.7 mg, 0.060 mmol) and tetrabutylammonium fluoride monohydrate (50 mg) in DMF (3 mL) was stirred at room temperature for 2 hours. The reaction mixture was then diluted with ethyl acetate (50 mL), washed with 1% HCl (5 mL), water (5 mL), 1M potassium dihydrophosphate (5 mL), and brine (5 mL), dried over anhydrous magnesium sulfate, filtered, and concentrated. The residue was then purified by column chromatography eluted sequentially with 5% methanol in ethyl acetate followed by 50:50:5:1 chloroform-ethyl acetate-methanol-formic acid to give the title compound (33.0 mg, 98%). $^1$H NMR (DMSO-d$_6$, 500 MHz) δ 8.56 (s, 1H), 8.11 (m, 2H), 8.01 (d, 2H), 7.92 (dd, 1H), 7.66 (t, 1H), 7.62 (t, 1H), 7.55 (d, 1H), 7.45 (d, 1H), 7.22 (dd, 1H), 5.26 (m, 1H), 4.10 (m, 1H), 3.51–3.30 (m, 2H), 3.15 (dt, 1H), 3.07 (dd, 1H), 2.95 (dd, 1H), 2.10 (m, 2H), 1.17 (d, 3H). MS (FAB+) m/e 558 (M+H, Cl–35)$^+$.

EXAMPLE 34D (1β,2α,3α)-3-[N-{(2S,3R)-4-(4-chlorophenyl)-3-(4-biphenylyl)-2-butyl}aminocarbonyl]cyclobutane-1,2-dicarboxylic acid A mixture of 130 mg (0.353 mmol) of the compound resulting from Example 31D in 5 mL of dichloromethane was treated with 0.5 mL of oxalyl chloride. After 4 hours all volatiles were removed under reduced pressure to afford an oil. The oil was dissolved in 10 mL of dichloromethane, 131 mg (0.353 mmol) of (1RS,2SR)-2-(4-biphenylyl)-3-(4-chlorophenyl)-1-methylpropylamine hydrochloride, prepared by the procedures described in Example 114 of European Patent Application EP 611749, published Aug. 24, 1994, and incorporated herein by reference, was added followed by 114 mg (0.883 mmol) of diisopropylethylamine. After 24 hours the solution was washed with brine, and all volatiles were removed under reduced pressure to give 203 mg (84%) of a yellow oil. A tlc on silica gel eluting with hexane/ethyl acetate (2:1) revealed two inseparable spots at R$_f$=~0.4, which are presumably diastereomers.

A mixture of this product in 6 mL of methanol and 2 mL of water with 27.4 mg (0.652 mmol) of lithium hydroxide hydrate was heated to reflux under an atmosphere of nitrogen for 6 hours. The volatiles were removed under reduced pressure, the product was mixed with 5 mL of water and the mixture was extracted with ethyl acetate. The combined extracts were dried (MgSO$_4$) and all volatiles were removed under reduced pressure. The resulting semisolid was purified by flash column chromatography on silica gel eluting with 95:5 chloroform-methanol to give 27 mg (18%) of the title compound. $^1$H NMR (300 MHz, CD$_3$OD) δ 0.92 (d, J=7 Hz, 3H), 2.3–2.4 (m, 2H), 2.8–2.9 (m, 2H), 3.3–3.4 (m, 2H), 3.6–3.8 (m, 2H), 4.2–4.3 (m, 1H), 6.9–7.6 (m, 13H). MS (FAB)$^+$ m/e 505 (M+H)$^+$.

EXAMPLE 35

(1β,2β,3α,4α)-4-[N-Benzyl-N-(10-phenyidecyl) aminocarbonyl]cyclobutane-1,2,3-tricarboxylic acid

EXAMPLE 35A

N-Benzyl-10-phenyidecanamide

To a solution of 10-phenyldecanoic acid (1.101 g, 4.43 mmol) in 20 mL of CH$_2$Cl$_2$ at room temperature was added oxalyl chloride (1.41 g, 11.08 mmol) and 1 drop of DMF, and the reaction mixture was stirred for 1 hour under nitrogen. The $CH_2Cl_2$ and excess oxalyl chloride were evaporated. The reaction was redissolved in $CH_2Cl_2$ and benzylamine (1.42 g, 13.3 mmol) and 2 mL of saturated aqueous $NaHCO_3$ were added and the reaction stirred for 12 hours. The reaction was taken up in EtOAc and washed with 1N HCl×2, followed by saturated aqueous NaCl, and evaporated to give 1.462 g (98%) of an oil that was used without further purification. $^1$H NMR ($CDCl_3$, 300 MHz) δ 1.30 (m, 10H), 1.55–1.72 (m, 4H), 2.20 (t, 2H), 2.59 (t, 2H), 4.45 (d, 2H), 5.68 (bs, 1H), 7.12–7.38 (m, 10H). MS ($DCl—NH_3$) m/e $(M+H)^+$ 338.

EXAMPLE 35B

N-Benzyl-N-(10-phenyidecyl)amine

The compound resulting from Example 35A (1.462 g, 4.33 mmol) was dissolved in THF and lithium aluminum hydride (8.66 mL, 1.0M solution in THF) was added by syringe, and the reaction was heated to reflux for 6 hours under nitrogen. The reaction was cooled and quenched with water and 15% aqueous sodium hydroxide, then filtered and evaporated to give 1.32 g (94%) of the title compound as an oil that was used without further purification. $^1$H NMR ($CDCl_3$, 300 MHz) δ 1.30 (m, 13H), 1.50 (m, 2H), 1.60 (m, 2H), 2.60 (app q, 4H), 3.75 (s, 2H), 7.10–7.35 (m, 10H). MS ($DCl—NH_3$) m/e $(M+H)^+$, 324.

EXAMPLE 35C (1β,2β,3α,4α)-4-[N-Benzyl-N-(10-phenyldecyl) aminocarbonyl]cyclobutane-1,2,3-tricarboxylic acid To a solution of 1,2,3,4-cyclobutanecarboxylic dianhydride (647 mg, 330 mmol) in 10 mL DMF at 0° C. was added a dropwise addition of the compound resulting from Example 35B (212 mg, 0.66 mmol) in 10 mL THF and the reaction stirred for 12 hours. The reaction was quenched with 5 mL of 1N HCl and then taken up in EtOAc. The organic phase was washed with saturated aqueous sodium chloride, dried over sodium sulfate and evaporated to an oil. The crude product was purified by silica gel chromatography eluting with 95:5:1 EtOAc—MeOH—$HCO_2H$ to give 284 mg of a white solid. $^1$H NMR ($CD_3OD$), 300 MHz) δ 1.20–1.32 (m, 13H), 1.45 –1.65 (m, 4H), 2.56 (t, 2H), 3.32 (s, 2H), 3.60–3.83 (m, 2H), 3.95–4.10 (m, 2H), 4.35–4.42 (m, 1H), 7.08–7.35 (m, 10H) MS ($DCl—NH_3$) m/e $(M+H)^+$, 537.

EXAMPLE 36

(1β,2β,3α,4α)-4-[N-Benzyl-N-(8-phenylocyl) aminocarbonyl]cyclobutane-1,2,3-tricarboxylic acid N-Benzyl-8-phenyl octanamide was prepared by the procedures described in Example 35A from 8-phenyloctanoic acid. $^1$H NMR ($CDCl_3$, 300 MHz) δ 1.34 (s, 6H), 1.52–1.72 (m, 4H), 2.20 (t, 2H), 2.60 (t, 2H), 4.44 (d, 2H), 5.68 (bs, 1H), 7.12–7.35 (m, 10H). MS ($Cl—NH_3$) m/e $(M+H)^+$, 310.

N-Benzyl-N-(8-phenyl)octylamine was prepared by the procedures described in Example 35B. $^1$H NMR ($CDCl_3$, 300 MHz) δ 1.30 (m, 8H), 1.42–1.70 (m, 5H), 2.60 (app q, 4H), 3.78 (s, 2H), 7.10–7.35 (m, 10H). MS ($Cl—NH_3$) m/e $(M+H)^+$ 296.

The title compound was prepared from N-Benzyl-N-(8-phenyl)octylamine and 1,2,3,4-cyclobutanetetracarboxylic dianhydride by the procedures described in Example 35C. $^1$H NMR ($CD_3OD$), 300 MHz) δ 1.20–1.32 (m, 8H), 1.45–1.62 (m, 6H), 2.52 (t, 2H), 3.45–3.83 (m, 3H), 3.97–4.10 (m, 1H), 435–4.42 (dd, 1H), 4.47–4.85 (m, 1H) 7.08–7.35 (m, 10H) MS ($DCl—NH_3$) m/e $(M+H)^+$ 509.

EXAMPLE 37

2-[N-{(2S,3R)-4-(4-Chlorophenyl)-3-(4-biphenylyl)-2-butyl}aminocarbonyl]cyclobutane-1-carboxylic acid

EXAMPLE 37A

2-[N-{(2S,3R)-4-(4-Chlorophenyl)-3-(4-biphenylyl)-2-butyl}aminocarbonyl]cyclobutane-1-carboxylic acid methyl ester To a solution of 56 mg (0.31 mmol) trans-1,2-cyclobutanedicarbonylchloride in 3 mL of ethyl ether at –10° C. was added a solution of 106 mg (0.31 mmol) of (1RS,2SR)-2-(4-biphenylyl)-3-(4-chlorophenyl)-1-methylpropylamine hydrochloride, prepared by the procedures described in Example 114 of European Patent Application EP 611749, published Aug. 24, 1994, 0.25 mL (6.2 mmol) of methanol and 65 µL (0.46 mmol) of triethylamine in 3 mL of $CH_2Cl_2$ dropwise. The mixture was stirred overnight during which time the cold bath melted. The mixture was poured into a separatory funnel containg 50 mL of ethyl ether and 20 mL of $H_2O$ and the phases were separated. The organic phase was extracted with 1N aqueous HCl and then dried over $MgSO_4$, filtered and concentrated. The residue was purified by column chromatography on $SiO_2$ eluting with 40% ethyl acetate in hexanes to give 52 mg (35%) of the title compound as a 1:1 mixture of diastereomers. $^1$H NMR ($CDCl_3$) δ 7.57 (m, 2H), 7.49 (m, 2H), 7.43 (m, 2H), 7.32 (m, 1H), 7.13 (m, 4H), 6.92 (m, 2H), 5.74 (bd, 1H), 4.33 (m, 1H), 3.64, 3.67, (2s, total 3H), 2.87–3.35 (m, 5H), 1.91–2.38 (m, 4H), 1.02 (2d, total 3H). MS (DCl $NH_3$) m/e $(M+H)^+$.

EXAMPLE 37B

2-[N-{(2S,3R)-4-(4-Chlorophenyl)-3-(4-biphenylyl)-2-butyl}aminocarbonyl]cyclobutane-1-carboxylic acid To a solution of 50 mg (0.10 mmol) of the compound resulting from Example 37A in 1.5 mL of THF at 0° C. was added a solution of 8 mg (0.20 mmol) of $LiOH.H_2O$ in 0.5 mL of $H_2O$. After stirring the mixture for 2 hours the reaction was quenched by the addition of 0.25 mL of 3N aqueous HCl. The reaction mixture was poured into 5 mL of $H_2O$ and extracted with 2×10 mL portions of ethyl acetate. The combined organic phases were extracted with brine, dried over $MgSO_4$, filtered and concentrated to give 44 mg (96%) of the title compound. $^1$H NMR (DMSO-$d_6$) δ 7.76 (m, 1H), 7.62 (m, 2H), 7.53 (d, 2H), 7.44 (m, 2H), 7.33 (m, 1H), 7.18 (m, 4H), 7.02 (m, 2H), 4.05 (m, 1H), 2.78–3.38 (m, 5H), 1.86–2.09 (m, 4H), 0.85 (2d, total 3H). MS (DCl $NH_3$) m/e 479 $(M+H+NH_3)^+$. HRMS (FAB) Calcd for $C_{28}H_{29}ClNO_3$: 462.1836. Found: 462.1840.

EXAMPLE 38

(1β,2β,3α,4α)-4-[N-Benzyl-N-(4-(3-chlorophenoxy) benzyl)aminocarbonyl]cyclobutane-1 2,3-tricarboxylic acid

EXAMPLE 38A 4-(3-Chlorophenoxy)benzaldehyde

3-Chlorophenol (0.52 g, 4 mmol), 4-fluorobenzaldehyde (0.50 g, 4 mmol), and potassium carbonate (0.56 g, 4 mmol)

were stirred in DMF (5 mL) at 80° C. for 48 hours. The reaction mixture was diluted with ethyl acetate and washed with water and brine, dried over Na$_2$SO$_4$, filtered and evaporated to give the title compound in 95% yield. $^1$H NMR (CDCl$_3$, 300 MHz) δ 6.95–7.40 (m, 9H), 7.85–8.31 (m, 4H), 9.94 (s, 1H). MS m/e 233 (M+H)$^+$.

EXAMPLE 38B (1β,2β,3α,4α)-4-[N-Benzyl-N-(4-(3-chlorophenoxy) benzyl)aminocarbonyl]cyclobutane-1,2,3-tricarboxylic acid The title compound was prepared by the procedures described in Example 3 using the compound resulting from Example 38A. $^1$H NMR (CDCl$_3$, 500 MHz) δ 3.6 (m, 2H), 3.92–4.95 (m, 6H), 6.9–7.38 (m, 13H). MS m/e 538 (M+H)$^+$.

EXAMPLE 39

(1β,2β,3α,4α)-4-[N-Benzyl-N-(2-chloro-4-(phenoxy)benzyl)aminocarbonyl]cyclobutane-1,2,3-tricarboxylic acid The title compound was prepared by the procedures described in Example 3 from 4-phenoxy-2-chlorobenzaldehyde, prepared by analogy to the procedure used for 4-(3-chlorophenoxy)benzaldehyde. $^1$H NMR (CDCl$_3$, 500 MHz) δ 3.59 (m, 2H), 3.85–4.90 (m, 6H), 6.89–7.68 (m, 13H). MS m/e 538 (M+H)$^+$.

EXAMPLE 40

(1β,2β,3α,4α)-4-[N-Benzyl-N-(3-chloro-4-(phenoxy)benzyl)aminocarbonyl]cyclobutane-1,2,3-tricarboxylic acid The title compound was prepared by the procedures described in Example 3 from 4-phenoxy-3-chlorobenzaldehyde, prepared by analogy to the procedure used for 4-(3-chlorophenoxy)benzaldehyde. $^1$H NMR (CDCl$_3$, 500 MHz) δ 3.57 (m, 2H), 3.90–4.89 (m, 6H), 6.90–7.51 (m, 13H). MS m/e 538 (M+H)$^+$.

EXAMPLE 41

(±)-(1α,2β,4α)-2-[N-{(2S,3R)-4-(4-Chlorophenyl)-3-(4-biphenylyl)-2-butyl}aminocarbonyl]-4-hydroxymethylcyclobutane-1-carboxylic acid sodium salt

EXAMPLE 41A (±)-(1β,2α,4α)-3-Hydroxymethyl-1,2-dicarboxylic acid dibenzyl ester To a −20° C. solution of the compound resulting from Example 31D (551 mg, 1.50 mmol) and N-methylmorpholine (0.329 mL, 3.0 mmol) in THF (8 mL) was added isobutyl chloroformate (0.292 mL, 2.24 mmol). After 45 minutes sodium borohydride (277 mg, 7.50 mmol) was added, followed by addition of methyl alcohol (0.5 mL). After 1.5 hours at −20° C., saturated aqueous ammonium chloride solution (1 mL) was added to the reaction. The reaction mixture was diluted with ether (80 mL), washed with water (2×10 mL) and brine, dried over anhydrous magnesium sulfate, filtered, and concentrated in vacuo. The residue was then purified with column chromatography eluting with 5% ether in chloroform to give the title compound (395 mg, 74%). $^1$H NMR (300 MHz, CDCl$_3$) δ 7.34 (m, 10H), 5.155 (d, 1H), 5.150 (d, 1H), 5.13 (s, 2H), 3.60 (m, 3H), 2.76 (m, 1H), 2.32 (m, 1H), 2.17 (t, 1H), 2.05 (m, 1H).

EXAMPLE 41 B (±)-(1β,2α,4α)-1-Benzyloxycarbonylcyclobutane-2,3-gamma-lactone A solution of the compound resulting from Example 41A (157.5 mg) and DBU (34 mg) in toluene (5 mL) was heated at 100° C. for 1 hour. After the reaction mixture was cooled to room temperature, it was filtered through silica gel (5 g) and rinsed with ethyl acetate. The filtrate was evaporated in vacuo to give the title compound which was used without purification. $^1$H NMR (300 MHz, CDCl$_3$) δ 7.48 (m, 5H), 5.20 (s, 2H), 4.40 9dd, 1H), 4.27 (dd, 1H), 3.40 (m, 1H), 3.30 (m, 2H), 2.60 (m, 1H), 2.39 (m, 1H).

EXAMPLE 41C (±)-(1β,2α,4α)-2,3-gamma-Lactone cyclobutane-1-carboxylic acid

A mixture of the compound resulting from Example 41B and 10% palladium on carbon (100 mg) in ethyl aceate was hydrogenated under a hydrogen balloon for 2.5 hours. The mixture was then filtered through celite and rinsed with ethyl acetate. The filtrate was evaporated in vacuo to give the title compound which was used without further purification (67 mg, 97% for 2 steps). $^1$H NMR (300 MHz, DMSO-d$_6$) δ 4.36 (dd, 1H), 4.25 (dd, 1H), 3.25 9m, 1H), 3.10 (m, 2H), 2.43 (m, 1H), 2.28 (m, 1H).

EXAMPLE 41 D (±)-(1α,2β,4α)-1-[N-{(2S,3R)-4-(4-Chlorophenyl)-3-(4-biphenylyl)-2-butyl}aminocarbonyl] cyclobutane-2,3-gamma-Lactone To a solution of the compound resulting from Example 41C (63 mg, 0.40 mmol) in dichloromethane (5 mL) was added oxalyl chloride (2.0M solution in dichloromethane, 0.24 mL) and a tiny drop of dimethylformamide in dichloromethane (25 volume %). After 1 hour, the solvent was evaporated, and the resulting acid chloride was dried under the high vacuum for 0.5 hour. The residue was redissolved in dichloromethane (15 mL), and (1RS,2SR)-2-(4-biphenylyl)-3-(4-chlorophenyl)-1-methylpropylamine hydrochloride, prepared by the procedures described in Example 114 of European Patent Application EP 611749, published Aug. 24, 1994, (163.7 mg, 0.44 mmol) was added to the solution. After stirring overnight, the reaction mixture was filtered through silica gel and rinsed with ethyl acetate. The filtrate was evaporated in vacuo, and the residue was purified by column chromatography eluting with 100% ether to give the title compound (89.7 mg, 47%) as a mixture of two diastereomers (ratio, 1:1). $^1$H NMR (300 MHz, CDCl$_3$) δ 7.60–7.30 (m, 7H), 7.15 (m, 4H), 6.96 (m, 2H), 5.26 (m, 1H), 4.45 (m, 1H), 4.39 (m, 1H), 4.30 (dd, 1H), 3.32 (m, 2H), 3.10–2.90 (m, 4H), 2.71 (m, 1H), 2.25 (m, 1H), 1.05 (2 doublets, 3H).

EXAMPLE 41E (±)-(1α,2β,4α)-2-[N-{(2S,3R)-4-(4-Chlorophenyl)-3-(4-biphenylyl)-2-butyl}aminocarbonyl]-4-hydroxymethylcyclobutane-1-carboxylic acid sodium salt To a solution of the lactone resulting from Example 42D (41 mg, 0.083 mmol) in THF was added NaOH (1.0M in water, 0.091 mL), and the reaction mixture was stirred overnight. The solvent was evaporated to give the title compound. $^1$H NMR (500 MHz, DMSO-d$_6$) δ 9.66, 7.98 (2 m's, 1H), 7.64 (m, 2H, 7.45 (m, 2H), 7.43 (m, 2H), 7.33 (m, 1H), 7.18 (m, 4H), 7.04 (m, 2H). 4.40–4.00 (4 m's, 2H), 3.72, 3.60 (2 t's, 1H), 3.27–2.93 (m, 4H), 2.86 (m, 2H), 2.34 (m, 1H), 1.97 (m, 1H), 1.25 (m, 1H), 0.86 (2 d's, 3H). MS (FAB−) m/e 472 (M−H).

EXAMPLE 42

(1α,2β,3β,4α)-1-{N-Benzyl-N-[(4S*,5S*)-(4-acetoxy-5-methyl-6-phenylhexyl] aminocarbonyl}cyclobutane-2,3,4-tricarboxylic acid

EXAMPLE 42A syn-(1-Methyl-2-hydroxy)-5-benzyloxypentylphenyl ketone

TiCl$_4$ (1.0M solution in CH$_2$Cl$_2$, 16.8 mL) was added dropwise to a −78° C. solution of propiophenone (2.05 g, 15.2 mmol) in 77 mL of CH$_2$Cl$_2$. After 5 minutes at −78° C. Et$_3$N (2.3 mL, 16.8 mmol) was added, and the reaction mixture was stirred at −78° C. for 0.5 hours. 4-Benzyloxybutyraldehyde (3.0 g, 16.8 mmol), prepared by the method described in Heterocycles 28(2): 663, (1989), was added dropwise, neat. The reaction mixture was stirred for 0.5 hours at −78° C. and then quenched by the addition of 50% saturated NH$_4$Cl solution. The solution was warmed to room temperature and extracted with CH$_2$Cl$_2$. The combined organic extracts were washed with saturated NaCl solution, dried (MgSO$_4$), filtered, concentrated, and flash chromatographed on silica gel eluting with 85:15 hexane-ethyl acetate to afford the title compound (3.67 g) as a clear oil. $^1$H NMR (300 MHz, CDCl$_3$) δ 1.28 (d, 3H), 1.60 (t, 3H), 1.67–1.88 (m, 2H), 3.52 (m, 3H), 4.03 (m, 1H), 4.51 (s, 2H), 7.32 (s, 5H), 7.48 (t, 2H), 7.59 (t, 2H), 7.95 (d, 2H). MS (DCl/NH$_3$) m/e 313 (M+H)$^+$.

EXAMPLE 42B syn-(1-Methyl-2-acetoxy)-5-benzyloxypentylphenyl ketone

Acetic anhydride (1.1 mL, 11.7 mmol) was added dropwise to a 0° C. solution of the compound resulting from Example 42A and a catalytic amount of DMAP in 100 mL of CH$_2$Cl$_2$. The reaction mixture was stirred for 24 hours at room temperature, then 0.1N HCl was added. The mixture was extracted with CH$_2$Cl$_2$ (3×). The combined organic layers were washed with saturated NaCl solution, dried (MgSO$_4$), filtered, and concentrated to afford the title compound (2.9 g) as a colorless oil. $^1$H NMR (300 MHz, CDCl$_3$) δ 1.21 (d, 3H), 1.58–1.75 (m, 4H), 2.00 (s, 3H), 3.42 (t, 2H), 3.65 (m, 1H), 4.46 (s, 2H), 5.30 (m, 1H), 7.30 (t, 5H), 7.47 (t, 2H), 7.58 (t, 1H), 7.90 (m, 2H). MS (DCl/NH$_3$) m/e 386 (M+NH$_4$)$^+$.

EXAMPLE 42C

Benzyl-[syn-(4-acetoxy-5-methyl)-6-hydroxy-6-phenyl]hexyl ether

A solution of the compound resulting from Example 45B (0.5 g, 1.4 mmol), CeCl$_3$.7H$_2$O, and 5 mL of MeOH was stirred at 0° C. as NaBH$_4$ (0.16 g, 4.2 mmol) was added portionwise. The reaction mixture was stirred at 0° C. for 0.25 hours, then 25 mL of 3N HCl was added (cautiously), followed by the addition of saturated NaCl solution. The solution was extracted with ether (3×). The combined organic layers were washed with saturated NaCl solution, dried (MgSO$_4$), filtered, and concentrated in vacuo to afford the title compound (0.5 g) as a colorless oil (as a mixture of diastereomers). $^1$H NMR (300 MHz, CDCl$_3$) δ 0.60 (d, 1.5H), 0.97 (d, 1.5H), 1.57–1.74 (m, 4H), 1.85–1.98 (m, 1H), 2.02 (s, 1.5H), 2.15 ( s, 1.5H), 3.45 (t, 1H), 3.51 (m, 1H), 4.12 (dd, 0.5H), 4.50 (d, 2H), 4.75 (m, 0.5H), 4.90 (m, 0.5H), 5.43 (m, 0.5H), 7.32 (m, 10H). MS (DCl/NH$_3$) m/e 374 (M+NH$_4$)$^+$.

EXAMPLE 42D

Benzyl[syn-(4-acetoxy-5-methyl)-6-trifluoroacetoxy-6-phenyl]hexyl ether

Trifluoroacetic anhydride (0.2 mL, 1.4 mmol) was added dropwise to a 0° C. solution of the compound resulting from Example 42C (0.5 g, 1.4 mmol), pyridine (0.11 mL), and 7 mL of CH$_2$Cl$_2$. The reaction mixture was stirred at 0° C. for 4.5 hours then quenched with 0.1N HCl and extracted with CH$_2$Cl$_2$ (3×). The combined organic layers were washed with 0.1N HCl, dried (MgSO$_4$), filtered, and concentrated in vacuo to afford the title compound (0.59 g) as a colorless oil (as a mixture of diastereomers). $^1$H NMR (300 MHz, CDCl$_3$) δ 0.78 (d, 1.5H), 1.10 (d, 1.5H), 1.50 (m, 1H), 1.64 (m, 2H), 1.78 (m, 1H), 2.02 (d, 3H), 2.32 (m, 1H), 3.39 (t, 1H), 3.50 (m, 2H), 4.98 (d, 2H), 4.67 (m, 0.5H), 5.29 (m, 0.5H), 5.52 (d, 0.5H), 5.78 (d, 0.5H), 7.30 (m, 10H). MS (DCl/NH$_3$) m/e 470 (M+NH$_4$)$^+$.

EXAMPLE 42E syn-(4-Acetoxy-5-methyl)-6-phenyl-1-hexanol

A mixture of the compound resulting from Example 42D (0.59 g, 1.3 mmol), anhydrous 10% Pd/C (0.16 g) and 50 mL of EtOAc was hydrogenated in a Parr shaker at room temperature for 39 hours. The mixture was filtered and concentrated in vacuo, and the residue was flash chromatographed on silica gel eluting with 8:2 hexane-EtOAc to afford the title compound (0.18 g) as a colorless oil. $^1$H NMR (300 MHz, CDCl$_3$) δ 0.89 (d, 3H), 1.45–1.60 (m, 3H), 1.69 (m, 2H), 2.00 (br s, 1H), 2.09 (s, 3H), 2.33 (dd, 1H), 2.77 (dd, 1H), 3.64 (t, 2H), 4.92 (m, 1H), 7.08–7.22 (m, 2H), 7.28 (m, 3H). MS (DCl/NH$_3$) m/e 268 (M+N H$_4$)$^+$.

EXAMPLE 42F

1-Iodo-syn-(4-acetoxy-5-methyl)-6-phenylhexane

A solution of the compound resulting from Example 42E (0.33 g, 1.39 mmol), and 9.2 mL of anhydrous CH$_3$CN was stirred at room temperature as the following was added sequentially: imidazole (0.24 g, 3.5 mmol), triphenylphosphine (0.40 g, 1.5 mmol) and iodine (0.39 g, 1.5 mmol). The reaction mixture was stirred at room temperature for 1.25 hours, then H$_2$O was added, and the mixture was extracted with CH$_2$Cl$_2$. The combined organic layers were washed with saturated sodium thiosulfate solution followed by saturated NaCl solution, dried (MgSO$_4$), filtered, and concentrated in vacuo to afford a white solid. The solid was triturated with hexane (3×), decanting after each. The hexane layers were combined, concentrated in vacuo, and flash chromatographed on silica gel eluting with 95:5 hexane-EtOAc to afford the title compound (0.38 g) as a colorless oil. $^1$H NMR (300 MHz, CDCl$_3$) δ 1.55 (s, 3H), 1.70 (t, 2H), 1.75–1.86 (m, 2H), 1.99 (m, 1H), 2.09 (s, 3H), 2.34 (dd, 1H), 2.77 (dd, 1H), 3.20 (t, 2H), 4.90 (m, 1H), 7.10–7.22 (m, 3H), 7.28 (m, 2H). MS (DCl/NH$_3$) m/e 378 (M+NH$_4$)$^+$.

EXAMPLE 42G

N-(Benzyl)-N-(t-butoxycarbonyl)-N-[(syn-4-acetoxy-5-methyl)-6-phenylhexyl]amine

A solution of N-benzyl-N-t-butoxycarbonylamine (0.22 g, 1.05 mmol), prepared by the method described in J. Heterocyclic Chem. 22(5), 1173 (1985), and 0.45 mL of anhydrous DMF was added dropwise to a 0° C. suspension of NaH (0.043 g 1.05 mmol, 600%o dispersion, hexane washed) and 1.7 mL of anhyrous DMF. The sodium salt was formed for 0.5 hours at room temperature, then a solution of the compound resulting from Example 42F (0.38 g, 1.05 mmol) and 0.5 mL of anhydrous DMF was added dropwise. The reaction mixture was stirred for 2 days at room temperature. Ice water was added and the solution was extracted (3x) with ethyl acetate. The combined organic layers were washed with H$_2$O , cold 0.1N HCl, and saturated NaCl solution, dried (MgSO$_4$), filtered, and concentrated in vacuo to afford the title compound (0.46 g) as a colorless oil. $^1$H NMR (300 MHz, CDCl$_3$) δ 0.82 (d, 3H), 1.39–1.57 (m, 13H), 1.92 (br s, 1H), 2.06 (s, 3H), 2.30 (dd, 1H), 2.72 (dd, 1H), 3.18 (br d, 2H), 4.29–4.49 (m, 2H), 4.85 (s, 1H), 7.10 (d, 2H), 7.19–7.38 (m, 8H). MS (DCl/NH$_3$) m/e 440 (M+H)$^+$, 457 (M+NH$_4$)$^+$.

EXAMPLE 42H

N-Benzyl-N-[(syn-4-acetoxy-5-methyl)-6-phenylhexyl]amine

Trifluoroacetic acid (7.7 mL) was added to a 0° C. solution of the compound resulting from Example 42G (0.46 g, 1.07 mmol) and 7.7 mL of CH$_2$Cl$_2$. The reaction was stirred for 0.5 hours at 0° C. and for 1.5 hours at room temperature. The solvent was evaporated in vacuo, toluene was added and evaporatedin vacuo (2x). Amberlite resin (IRA-400-OH, 0.5 g, washed successively with H$_2$O , EtOH, ether, and dried) and 15 mL of CH$_2$Cl$_2$ was added, and the suspension was stirred for 18 hours at room temperature. The suspension was filtered and concentrated in vacuo to afford the title compound (0.33 g) as a colorless oil. $^1$H NMR (300 MHz, CDCl$_3$) δ 0.85 (d, 3H),1.58 (m, 4H), 1.95 (s, 1H), 2.07 (s, 3H), 2.31 (m, 2H), 2.68 (s, 1H), 2.74 (dd, 2H), 3.82 (s, 2H), 4.85 (m, 1H), 7.08–7.22 (m, 3H), 7.28 (m, 3H), 7.37 (m, 4H). MS (DCl/NH$_3$) m/e 340 (M+H)$^+$.

EXAMPLE 42I (1α,2β,3β,4α)-4-{N-Benzyl-N-[syn-(4-acetoxy-5-methyl)-6-phenylhexyl]aminocarbonyl}cyclobutane-1,2,3-tricarboxylic acid 1,3-dibenzyl ester A solution of dicyclohexylcarbodiimide (0.19 g, 0.94 mmol) and 1.0 mL of DMF was added to a solution of (1α,2β,3β,4α)-cyclobutanetetracarboxylic acid 1,3-dibenzyl ester (0.39 g, 0.94 mmol), the compound resulting from Example 42H (0.32 g, 0.94 mmol), 1-hydroxybenzotriazole hydrate (0.13 g, 0.94 mmol), and 4.0 mL of DMF. The reaction mixture was stirred for 18 hours at room temperature. EtOAc was added and the solid removed by filtration. The filtrate was washed with 1N HCl, H$_2$O and saturated aqueous NaCl solution, dried (MgSO$_4$), filtered and concentrated in vacuo to afford a yellow oil which was purified by flash chromatography on silica gel eluting with 97:2.5:0.5 CHCl$_3$—MeOH-acetic acid to afford the title compound (0.19 g) as a colorless oil. $^1$H NMR (300 MHz, CDCl$_3$) δ 1.32–1.58 (m, 4H), 1.92 (m, 1H), 2.05 (d, 3H), 2.30 (m, 1H), 2.39 (s, 3H), 2.70 (m, 1H), 3.20 (m, 1H), 3.61–3.90 (m, 4H), 4.10 ( m, 2H), 5.15 (m, 4H), 7.10 (m, 3H), 7.19 (t, 6H), 7.30 (m, 11H). MS (FAB) m/e 734 (M+H)$^+$.

EXAMPLE 42J (1α,2β,3β,4α)-4-{N-Benzyl-N-[(4S*,5S*)-(4-acetoxy-5-methyl)6-phenylhexyl]aminocarbonyl}cyclobutane-1,2,3-tricarboxylic acid The compound resulting from Example 42I (0.06 g, 0.08 mmol) was hydrogenated over a catalytic amount of Pd/C using a hydrogen balloon. The reaction mixture was filtered, the solvent evaporated and the residue flash chromatagraphed eluting with 94:5:1 CHCl$_3$—MeOH—AcOH to afford the title compound (3.7 mg) as a white powder. $^1$H NMR (300 MHz, CD$_3$OD) δ 0.85 (m, 3H), 1.20 (s, 2H), 1.55 (m, 2H), 2.02 (m, 2H) 2.19–2.28 (m, 1H), 2.62–2.72 (m, 1H), 3.08 (m, 2H), 3.18 (m, 2H), 3.5–3.72 (m, 3H) 4.90 (s, 2H), 7.06–7.17 (t, 8H), 7.20–7.38 (m, 12H). MS (FAB) m/e 554 (M+H)$^+$.

EXAMPLE 43

(1α,2β,3β,4α)-4-{N-Propyl-N-[(4S*,5S*)-(5-methyl-4-napthoyloxy)-6-phenylhexyl]aminocarbonyl}cyclobutane-1,2,3-tricarboxylic acid

EXAMPLE 43A (4S*,5S*)-[1-Methyl-2-(2-naphthoyloxy)]-5-benzyloxypentylphenyl ketone A mixture of the compound resulting from Example 42A (4.1 g, 13.1 mmol), 2-naphthoic acid (2.4 g, 14.3 mmol), EDAC (5.3 g, 27 mmol), DMAP (3.4 g, 27 mmol), and 110 mL of anhydrous THF was stirred at room temperature for 18 hours. The THF was evaporated in vacuo, and water was added to the residue. The mixture was extracted with EtOAc, and the combined organic extracts were washed with saturated sodium bicarbonate, 1N HCl, and saturated sodium chloride solution, dried over MgSO$_4$, filtered, and concentrated in vacuo. The crude product was purified by flash chromatography on silica gel eluting with 95:5 hexane-ethyl acetate to afford the title compound (3.3 g) as a colorless oil. $^1$H NMR (300 MHz, CDCl$_3$) δ 1.35 (d, 3H), 1.72 (m, 2H), 1.88 (m, 2H), 3.48 (t, 2H), 3.97 (m, 1H), 4.45 (s, 2H), 5.62 (m, 1H), 7.28 (m, 5H), 7.4 (t, 3H), 7.50–7.60 (m, 3H), 7.80–8.00 (m, 6H), 8.45 (s, 1H). MS (DCl/NH$_3$) m/e 484 (m+NH$_4$)$^+$.

EXAMPLE 43B

Benzyl-{syn-[5-methyl-4-(2-naphthoyloxy)]-6-hydroxy-6-phenyl}hexyl ether

Using the compound resulting from Example 43A and the procedure described for Example 42C afforded the title compound as a mixture of diastereomers. $^1$H NMR (300 MHz, CDCl$_3$) δ 0.82 (d, 1.5H), 1.20 (d, 1.5H), 1.60–2.00 (m, 4H), 2.02–2.28 (m, 2H), 3.42–3.60 (m, 2H), 3.77 (d, 0.5H), 4.25 (dd, 2H), 4.50 (d, 2H), 5.20 (m, 0.5H), 5.80 (m, 0.5H), 7.21–7.42 (m, 10H), 7.54–7.68 (m, 2H), 7.85–8.15 (m, 4H), 8.60 (d, 1H). MS (DCl/NH$_3$) m/e 486 (M+NH$_4$)$^+$.

EXAMPLE 43C

Benzyl{syn-[5-methyl-4-(2-naphthoyloxy)]-6-trifluoroacetyloxy-6-phenyl}hexyl ether Using the procedure described for Example 42D and the compound resulting from Example 43B afforded the title compound as a mixture of diastereomers. $^1$H NMR (300 MHz, CDCl$_3$) δ 0.82 (d, 1.5H), 1.30 (d, 1.5H), 1.51–1.68 (m, 1H), 1.68–2.05 (m, 3H), 2.49 (m, 1H), 3.38–3.45 (dt, 1H), 3.48–3.60 (m, 1H), 4.48 (d, 2H), 4.98 (dt, 0.5H), 5.56 (d, 0.5H), 5.65 (m, 0.5H), 5.90 (d, 0.5H), 7.20–7.40 (m, 10H), 7.52–7.68 (m, 2H), 7.86–8.08 (m, 4H), 8.55 (d, 1H). MS (DCI/NH$_3$) m/e 482 (M+NH$_4$)$^+$.

EXAMPLE 43D syn-[5-Methyl-4-(2-naphthoyloxy)]-6-phenyl-1-hexanol

A mixture of the compound resulting from Example 43C (0.43 g, 0.76 mmol), PdOH (43 mg) and 12 mL of MeOH was hydrogenated at room temperature for 18 hours using a hydrogen balloon. The reaction mixture was filtered and concentrated in vacuo. The crude product was flash chromatagraphed on silica gel eluting with 9:1 hexane-ethyl acetate to afford the title compound (0.11 g) as a colorless oil. $^1$H NMR (300 MHz, CDCl$_3$) δ 1.06 (d, 3H), 1.67 (m, 2H), 1.78–1.96 (m, 3H), 2.19 (m, 1H), 2.48 (dd, 1H), 2.90 (dd, 1H), 3.70 (q, 2H), 5.25 (m, 1H), 7.15 (m, 3H), 7.25 (m, 2H), 7.60 (m, 2H), 7.90 (d, 2H), 7.99 (d, 1H), 8.10 (dd, 1H), 8.61 (s, 1H). MS (DCI/NH$_3$) m/e 380 (M+NH$_4$)$^+$.

EXAMPLE 43E syn-[5-Methyl-4-(2-naphthoyloxy)]-6-phenyl-1-methanesulfonylhexanol Using the procedure described in Example 42F and the product resulting from Example 43D afforded the title compound. $^1$H NMR (300 MHz, CDCl$_3$) δ 1.08 (d, 3H), 1.85 (m, 4H), 2.18 (m, 1H), 2.48 (dd, 1H), 2.85 (dd, 1H), 2.98 (s, 3H), 4.28 (m, 2H), 5.25 (m, 1H) 7.15 (m, 4H), 7.28 (m,$_1$H), 7.60 (m, 2H), 7.90 (d, 2H), 8.0 (d, 1H), 8.08 (dd, 1H), 8.60 (s, 1H). MS (DCI/NH$_3$) m/e 458 (M+NH$_4$)$^+$.

EXAMPLE 43F

N-{syn-[5-Methyl-4-(2-naphthoyloxy)]-6-phenyl-1-hexyl}-N-propylamine

A solution of the compound resulting from Example 43E (0.1 g, 0.23 mol), n-propylamine (0.029 mL, 0.35 mmol), diisopropylethylamine (0.044 mL, 0.25 mmol) and 1.0 mL of CH$_3$CN was stirred at 90° C. for 3 hours. The reaction mixture was concentrated in vacuo, and the resultant residue was flash chromatagraphed on silica gel eluting with 9:1 hexane-ethyl acetate saturated with NH$_3$ to provide the title compound (0.05 g) as a colorless oil. $^1$H NMR (300 MHz, CDCl$_3$) δ 0.09 (t, 3H), 1.04 (d, 3H), 1.46 (q, 2H), 1.58 (q, 2H), 1.68–1.92 (m, 2H), 2.15 (m, 1H), 2.45 (dd, 1H), 2.54 (t, 2H), 2.61 (t, 2H), 2.90 (dd, 1H), 5.22 (m, 1H), 7.15 (q, 3H), 7.25 (m, 2H), 7.60 (m, 2H), 7.90 (d, 2H), 7.98 (d, 1H), 8.10 (dd, 1H), 8.60 (s, 1H). MS (DCI/NH$_3$) m/e 404 (M+H)$^+$.

EXAMPLE 43G (1α,2β,3β,4α)-Cyclobutanetetracarboxylic acid-1,2,3-tribenzyl ester A suspension of (1α,2β,3β,4α)-cyclobutanetetracarboxylic acid 1,3-dibenzyl ester (2.5 g, 6.1 mmol), benzyl alcohol (0.42 mL, 4.1 mmol), EDAC (1.19 g, 6.1 mmol), DMAP (0.77 g, 6.1 mmol), and 61 mL of anhydrous THF was stirred at room temperature for 6 hours. The THF was evaporated in vacuo, and the residue was dissolved in methylene chloride. The solution was washed with 1N HCl and saturated NaCl solution, dried (MgSO$_4$), filtered, and concentrated in vacuo. The crude product was flash chromatagraphed on silica gel eluting with 98:1.5:0.5 CHCl$_3$—MeOH—AcOH to provide the title compound (1.27 g) as a white solid. $^1$H NMR (300 MHz, CDCl$_3$) δ 3.84 (m, 4H), 5.00 (m, 6H), 7.30 (m, 15H). MS (FAB) m/e 503 (M+H)$^+$.

EXAMPLE 43H (1α,2β,3β,4α)-4-{N-Propyl-N-[(4S*,5S*)-(5-methyl-4-naphthoyloxy)-6-phenylhexyl]aminocarbonyl}cyclobutane-1,2,3-tricarboxylic acid tribenzyl ester A mixture of the compound resulting from Examples y43F (0.12 g, 0.31 mmol), the compound resulting from Example 43G (0.17 g, 0.34 mmol), EDAC (66 mg, 0.34 mmol), DMAP (42 mg, 0.34 mmol), and 3.1 mL of anhydrous THF was stirred for 18 hours at room temperature. The reaction mixture was diluted with methylene chloride and washed with saturated sodium bicarbonate, 0.5N HCl, and saturated sodium chloride solution, dried (MgSO$_4$), filtered and concentrated in vacuo. The product was purified by flash chromatography eluting with 9:1 hexane-ethyl acetate to afford the title compound (0.10 g) as a colorless oil. $^1$H NMR (300 MHz, CDCl$_3$) δ 0.068–0.082 (m, 3H), 1.02 (d, 3H), 1.38 (m, 2H), 1.55 (m, 2H), 1.80 (m, 2H), 2.10 (m, 1H), 2.42 (t, 1H), 2.80 –3.32(m, 2H), 3.70–4.08 (m, 4H), 4.81–5.10 (m, 6H), 7.08–7.35 (m, 15H), 7.58 (m, 2H), 7.82–8.12 (m, 4H), 8.60 (dd, 1H). MS (FAB) m/e 926 (M+K)$^+$.

EXAMPLE 43I (1α,2β,3β,4α)-4-{N-Propyl-N-[(4S*,5S*)-(5-methyl-4-naphthoyloxy)-6-phenylhexyl]aminocarbonyl}cyclobutane-1,2,3-tricarboxylic acid Using the procedure described for Example 42E and the product resulting from Example 43H provided the title compound. $^1$H NMR (300 MHz, CDCl$_3$) δ 0.069–0.095 (m, 3H), 1.05 (t, 3H), 1.38–1.88 (m, 6H) 2.10 (m, 1H), (m, 1H), 2.80 (m, 1H), 3.0 (m, 2H), 3.22 (m, 2H), 3.75 (m, 2H), 3.95 ( m, 2H) 5.02–5.25 (m, 1H), 7.05 (t, 3H), 7.22 (q, 2H), 7.58 (m, 2H), 7.88 (m, 2H), 7.92 (t, 1H), 8.05 (d,1H), 8.60 (s, 1H). MS (FAB) m/e 618 (M+H)$^+$.

EXAMPLE 44

(1α,2α,3β,4β)-4-{N-Propyl-N-[(R)-6-methyl-9-phenyl-(E)-4-nonenyl]aminocarbonyl}cyclobutane-1,2,3-tricarboxylic acid

EXAMPlE 44A (−)-N-Propyl-N-[(R)-6-methyl-9-phenyl-(E)-4-nonethyl]amine

Using the procedure described in Example 43F and the compound resulting from Example 45B afforded the title compound. $^1$H NMR (300 MHz, CDCl$_3$) δ 0.095 (m, 6H), 1.30 (m, 2H), 1.36–1.54 (m, 3H), 1.60 (m, 4H), 2.05 (m, 3H), 2.54–2.65 (m, 6H), 5.20–5.40 (m, 2H), 7.18 (d, 6H), 7.28 (t, 2H). MS (DCI/NH$_3$) m/e 274 (M+H)$^+$.

EXAMPLE 44B (1α,2α,3β,4β)-4-{N-Propyl-N-[(R)-6-methyl-9-phenyl-(E)-4-nonenyl]aminocarbonyl}cyclobutane-1,2,3-tricarboxylic acid tribenzyl ester Using the procedure descibed in Example 43H and the compound resulting from Example 44A provided the title compound. $^1$H NMR (300 MHz, CDCl$_3$) δ 0.080 (m, 3H), 0.095 (t, 3H), 1.30 (m, 2H), 1.45 (m, 4H), 1.58 (m, 2H), 1.90 (m, 2H), 2.05 (m, 1H), 2.58 (q, 2H), 2.88–3.25 (m, 4H), 3.71–3.95 (m, 3H), 4.05 (dd, 1H), 4.85–5.15 (m, 6H), 5.25 (m, 2H), 7.17 (m, 3H), 7.30 (m, 17H). (FAB) m/e 758 (M+H)$^+$.

EXAMPLE 44C (1α,2α,3β,4β)-4-{N-Propyl-N-[(R)-6-methyl-9-phenyl-(E)-4-nonethyl]aminocarbonyl}cyclobutane-1,2,3-tricarboxylic acid tribenzyl ester Using the procedure described for Example 45E with the compound resulting from Example 44B provided the title compound. $^1$H NMR (300 MHz, CDCl$_3$) δ 0.085 (m, 3H), 0.095 (t, 3H), 1.80 (m, 2H), 1.58 (m, 6H), 1.95 (m, 2H), 2.19 (m, 1H), 2.08 (t, 2H), 3.01–3.45 (m, 4H), 3.79 (t, 2H), 4.00 (m, 2H), 5.30 (m, 2H), 7.12 (m, 3H), 7.25 (m, 2H). MS (FAB) m/e 488 (M+H)$^+$.

EXAMPLE 45

(1α,2α,3β,4β)-4-{N-Benzyl-N-[(R)-6-methyl-9-phenyl-(E)-4-nonethyl]aminocarbonyl}cyclobutane-1,2,3-tricarboxylic acid

EXAMPLE 45A (−)-(R)-6-Methyl-9-phenyl-(E)-4-nonenol

A solution of (−)-(R)-6-methyl-9-phenyl-(E)-4-nonenoic acid ethyl ester, prepared by the procedure described in J. Org. Chem., 59(8), 2253 (1994), (1.0 g, 3.8 mmol) and 7.9 mL of anhydrous THF was added dropwise to a 0° C. suspension of LAH (0.03 g, 7.9 mmol) and 7.9 mL of anhydrous THF. The reaction mixture was stirred for 2 hours at 0° C. and for 1 hour at room temperature. After cooling again to 0° C., 1.2 mL of MeOH was added slowly. The mixture was stirred for 0.25 hours at room temperature, then concentrated in vacuo. Saturated aqueous Rochelle's salt was added, and the mixture was extracted with isopropyl acetate. The organic layer was dried over MgSO$_4$, filtered, and concentrated in vacuo to provide the title compound (0.84 g) as a colorless oil. $^1$H NMR (300 MHz, CDCl$_3$) δ 0.095 (d, 3H), 1.21–1.38 (m, 3H), 1.51–1.70 (m, 4H), 2.02–2.15 (m, 3H), 2.58 (t, 2H), 3.65 (q, 2H), 5.23–5.45 (m, 2H), 7.18 (m, 3H), 7.28 (m, 2H). MS (DCl/NH$_3$) m/e 250 (M+NH$_4$)$^+$.

EXAMPLE 45B (−)-(R)-6-Methyl-9-phenyl-1-methanesulfonyl-(E)-4-nonenol

Using the procedure described for Example 42F and the compound resulting from Example 45A provided the title compound. $^1$H NMR (300 MHz, CDCl$_3$) δ 0.095 (d, 3H), 1.30 (t, 2H), 1.58 (m, 1H), 1.80 (m, 2H), 2.20 (m, 2.58 (t, 2H), 2.98 (s, 3H), 4.20 (t, 2H), 5.30 (m, 2H), 7.18 (m, 3H), 7.28 (m, 2H). MS (DCl/NH$_3$) m/e 328 (M+NH$_4$)$^+$.

EXAMPLE 45C (−)-N-Benzyl-N-[(R)-6-methyl-9-phenyl-(E)-4-nonenyl]amine

Using the procedure described for Example 43F, but substituting benzylamine for propylamine and using the compound resulting from Example 45B, provided the title compound. $^1$H NMR (300 MHz, CDCl$_3$) δ 0.095 (d, 3H), 1.30 (t, 2H), 1.40 (s, 1H), 1.60 (m, 4H), 2.05 (m, 3H), 2.60 (m, 4H), 3.78 (s, 3H), 5.20–5.40 (m, 2H), 7.16 (m, 3H), 7.25 (m, 3H), 7.32 (m, 4H). MS (DCl/NH$_3$) m/e 322 (M+H)$^+$.

EXAMPLE 45D (1α,2α,3β,4β)-4-{N-Benzyl-N-[(R)-6-methyl-9-phenyl-(E)-4-nonenyl]aminocarbonyl}cyclobutane-1,2,3-tricarboxylic acid tribenzyl ester Using the procedure described in Example 43H with the product resulting from Example 45C provided the title compound. $^1$H NMR (300 MHz, CDCl$_3$) δ 0.095 (dd, 3H), 1.28 (q, 2H), 1.48 (m, 4H), 1.82 (s, 1H), 1.92 (s, 1H), 2.55 (q, 2H), 3.00–3.22 (m, 2H), 3.65–4.12 (m, 4H), 4.45 (m, 2H), 4.82–5.28 (m, 8H), 7.00 (s, 1H), 7.11–7.41 (m, 24H). MS (FAB) m/e 806 (M+H)$^+$.

EXAMPLE 45E (1α,2α,3β,4β)-4-{N-Benzyl-N-[(R)-6-methyl-9-phenyl-(E)-4-nonenyl]aminocarbonyl}cyclobutane-1,2,3-tricarboxylic acid A solution of the compound resulting from Example 45D (0.27 g, 0.34 mmol), 1.3 mL 1M NaOH, and 5 mL THF was stirred at room temperature for 18 hours. 1N HCl (2 Ml) was added, and the mixture was extracted with methylene chloride. The organic layer was washed with saturated NaCl, dried over MgSO$_4$, filtered, concentrated in vacuo, and purified by flash chromatography on silica gel eluting with 94:5:1 CHCl$_3$—MeOH—AcOH to provide the title compound (10.2 mg) as a white powder. $^1$H NMR (300 MHz, DMSO-d$_6$) δ 0.088 (m, 3H), 1.20 (m, 2H), 1.50 (m, 3H), 1.90 (m, 2H), 2.05 (m, 1H), 2.75–3.20 (m 9H), 4.18–4.42 (m, 1H), 4.62–4.78 (m, 1H), 5.15–5.38 (m, 2H), 7.15 (d, 3H), (d, 3H), 7.25 (t, 6H), 7.30 (q, 1H). MS (FAB) m/e 558 (M+Na)$^+$.

EXAMPLE 46

(1α,2α,3β,4β)-4-[N-{2S,3R}-4-(3,4-dichlorophenyl)-3-(2-naphthoyloxy)-2-butyl}aminocarbonyl]]cyclobutane-1,2,3-tricarboxylic acid The title compound was prepared by the procedures described in Example 1 using N-(3,4-dichlorbenzyl)-N-(4-phenoxybenzyl)amine in place of N-benzyl-N-(4-phenoxybenzyl)amine. $^1$H NMR (DMSO-d$_6$, 300 MHz) δ 3.50 (m, 4H), 4.00–4.90 (m, 4H) 6.80–7.45 (m, 12H), 7.65 (m, 1H), 7.80 (m, 1H). MS (FAB)$^+$ m/e 572 (M+H)$^+$ and (FAB)$^−$ m/e 570 (M−H)$^−$.

The following compounds can be prepared according to the methods in the previous examples.

| Ex. No. | Name |
| --- | --- |
| 47 | (1S,2S,3S,4S)-2,3-Di(benzyloxycarbonyl)-4-[N-{(2S,3R)-4-(4-chlorophenyl)-3-(4-biphenylyl)-2-butyl}aminocarbonyl]cyclobutane-1-carboxylic acid; |
| 48 | (1R,2R,3R,4R)-2,3-Di(benzyloxycarbonyl)-4-[N-{(2S,3R)-4-(4-chlorophenyl)-3-(4-biphenylyl)-2-butyl}aminocarbonyl]cyclobutane-1-carboxylic acid; |
| 49 | (1S,2R,3R,4R)-3-Methoxycarbonyl-4-[N-{(2S,3R)-4-(4-chlorophenyl)-3-(4-biphenylyl)-2-butyl}aminocarbonyl]cyclobutane-1,2-dicarboxylic acid; |
| 50 | (1R,2S,3S,4S)-3-Methoxycarbonyl-4-[N-{(2S,3R)-4-(4-chlorophenyl)-3-(4-biphenylyl)-2-butyl}aminocarbonyl]cyclobutane-1,2-dicarboxylic acid; |

-continued

| Ex. No. | Name |
|---|---|
| 51 | (1R,2S,3S,4S)-4-[N-{2S,3R)-4-(4-chlorophenyl)-3-(4-biphenylyl)-2-butyl}aminocarbonyl]cyclobutane-1,2,3-tricarboxylic acid; |
| 52 | (1S,2S,3S,4S)-3-methoxycarbonyl-4-[N-{(2S,3R)-4-(4-chlorophenyl)-3-(4-biphenylyl)-2-butyl}aminocarbonyl]cyclobutane-1,2-dicarboxylic acid; |
| 53 | (1α,2β,3β,4α)-2-Cabromethoxy-4-[N-{(2S,3R)-4-(4-chlorophenyl)-3-(4-biphenylyl)-2-butyl}aminocarbonyl]cyclobutane-1,3-dicarboxylic acid; |
| 54 | (1β,2α,3α,4β)-2-Carboxymethoxy-4-[N-{(2S,3R)-4-(4-chlorophenyl)-3-(4-biphenyl)-2-butyl}aminocarbonyl]cyclobutane-1,3-dicarboxylic acid; and |
| 55 | (1β,2β,3α)-3-[N-{(2S,3R)-4-(4-chlorophenyl)-3-(4-biphenylyl)-2-butyl}aminocarbonyl]cyclobutane-1,2-dicarboxylic acid. |

Inhibition of Squalene Synthase

In vitro inhibition of squalene synthase may be measured by the following procedure.

Rat liver microsomal squalene synthase activity was measured using radioactive farnesyl diphosphate as a substrate and quantitating squalene synthesis by counting the radioactive squalene formed.

Rat liver microsomes, the source of enzyme, were prepared according to the method of Gillies, P. J., et al., Exp. Molc. Pathol. 44: 329–339 (1986), a modification of the procedure of Erickson, S. K., and Cooper, A. D., Metabolism, 29: 991–996 (1980). Approximately 30 μg of microsomal protein was incubated for 10 minutes at 37° C. with 5°–11 μM of $^3$H-farnesyl diphosphate, 49 mCi/mmol, and test compound in the presence of squalene (2 μL), Mg++, KF, reduced B-nicotinamide adenine dinucleotide phosphate, dithiothreitol, and $K_2PO_4$, pH 7.35, in a total volume of 200 μL. Oxygen was excluded from the closed incubation tube by degassing with nitrogen. The reaction was terminated by the addition of ethanolic KOH and after degassing with $N_2$, the microsomal membranes were solubilized by heating at 60° C. for 30 minutes. The squalene was extracted into hexane, and the squalene was separated from all other radioactive molcules by passage over an activated alumina column. The solution was collected in scintillation vials, evaporated to dryness, liquid scintillation fluid was added, and the radioactivity was determined in a liquid scintillation counter. The percent inhibition at a dose of 1 μM compared to controls with no test compound was determined. The % inhibition values for the compounds of the invention are shown in Table 1. The data show that the compounds of the invention are inhibitors of squalene synthase.

TABLE 1

In vitro Inhibition of Squalene Synthase

| Example No. | % Inhibition at 1 μM | Example No. | % Inhibition at 1 μM |
|---|---|---|---|
| 23 | 98 | 24 | 27 |
| 25 | 35 | 26 | 52 |
| 27 | 98 | 29 | 81* |
| 34 | 94 | 35 | 47 |
| 37 | 90 | 41 | 80 |
| 43 | 63 | 44 | 25 |
| 45 | 67 | 46 | 53 |

*% Inhibition at 0.15 μM

Inhibition of Protein Farnesyltransferase

In vitro inhibition of protein farnesyltransferase may be measured by the following procedure. (Procedures for determination of the inhibition of farnesylation of the oncogene protein Ras are described by Goldstein, et al., J. Biol. Chem., 266:15575–15578 (1991) and by Singh in U.S. Pat. No. 5,245,061 both of which are incorporated herein by reference.)

Rat brain protein farnesyltransferase activity was measured using an Amersham Life Science commercial scintillation proximity assay kit and substituting a biotin-K Ras B fragment (biotin-Lys-Lys-Ser-Lys-Thr-Lys-Cys-Val-Ile-Met-$CO_2$H), 0.1 μM final concentration, for the biotin-lamin substrate provided by Amersham. The enzyme was purified according to Reiss, Y., et al., Cell, 62:81–88 (1990), utilizing steps one through three. The specific activity of the enzyme was approximately 10 nmol substrate farnesylated/mg enzyme/hour. The percent inhibition of the farnesylation caused by the compounds of the invention (at $10 \times 10^{-6}$M) compared to an uninhibited control sample was evaluated in the same Amersham test system. The results for the compounds of the invention are shown in Table 2. The data show that the compounds of the invention are inhibitors of protein farnesyltransferase.

TABLE 2

In vitro Inhibition of Protein Farnesyltransferase

| Ex. No. | % Inhibition at 1 μM | Example No. | % Inhibition at 1 μM |
|---|---|---|---|
| 1 | 92 | 3 | 45 |
| 4 | 99 | 5 | 21 |
| 6 | 89 | 8 | 79 |
| 10 | 81 | 13 | 55 |
| 15 | 81 | 19 | 99 |
| 20 | 99 | 22 | 27 |
| 25 | 35 | 26 | 52 |
| 27 | 15 | 29 | 49 |
| 35 | 89 | 36 | 95 |
| 38 | 90 | 39 | 97 |
| 40 | 98 | 42 | 93 |
| 43 | 86 | 44 | 78 |
| 45 | 95 | 46 | 97 |

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, gluconheptanoate, glycerophosphate, hemisulfate, heptanoate, hexanoate, fumarate, hydrochloride, hydrobromide, hydroiodide, 2-hydroxyethanesulfonate lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the formula (I) of the invention are useful (in humans and other mammals) for inhibiting squalene synthase. The compounds of the formula (I) of the invention are also useful for inhibiting cholesterol biosynthesis. The compounds of the formula (I) of the invention are also useful for treating atherosclerosis and inhibiting progression of atherosclerosis. The compounds of the formula (I) of the invention are also useful for treating hyperlipidemia. The compounds of the formula (I) of the invention are also useful for treating fungal infections.

The compounds of the formula (I) of the invention are also useful for treating acne in humans. Methods to demonstrate this activity, appropriate doses and means of administration are disclosed in PCT patent application WO 94/22870, published Oct. 13, 1994 which is incorporated herein by reference.

The ability of the compounds of the formula (I) of the invention to inhibit cholesterol biosynthesis can be demonstrated in vivo according to the following method. The in vivo inhibition of cholesterol synthesis can be determined in a monkey model in which the monkeys are dosed, fasted overnight and bled in the morning. Plasma samples are prepared and analyzed for total cholesterol, HDL-cholesterol and triglycerides.

The ability of the compounds of the formula (I) of the invention to treat fungal infections can be demonstrated according to the method described by S. Shadomy and M. A. Pfaller. 1991. Laboratory Studies with Antifungal Agents: Susceptibility Tests and Quantitation in Body Fluids, pp. 1173–1183. In A. Balows, W. J. Hausler, Jr., K. L. Herrmann, H. Isenberg and H. J. Shadomy, Eds. Manual of Clinical Microbiology, 5th Ed. American Society for Microbiology, Washington, D.C. The antifungal activity of squalene synthase inhibitors has been reported by a number of researchers including Dufresne, et al., Tetrahedron 48/47 10221–10226 (1992) and Dawson, M. J., et al., J. Antibiot. (Tokyo) 45: 639–647 (1992).

The compounds of the formula (I) or (II) of the invention are useful (in humans and other mammals) for inhibiting protein farnesyltransferase and the farnesylation of Ras. These inhibitors of protein farnesyltransferase are also useful for inhibiting or treating cancer in humans and other mammals. Examples of the kinds of cancers which can be inhibited or treated with the compounds of the invention include, but are not limited to, carcinomas, such as lung, colorectal, exocrine pancreatic, cervical, esophageal, stomach, and small intestinal; sarcomas, such as oesteroma, osteosarcoma, lepoma, liposarcoma, hemanioma, and hemangiosarcoma; melanomas, such as amelanotic and melanotic; mixed types of cancers such as carcinosarcoma, lymphoid tissue type, follicular reticulum, cell sarcoma and Hodgkins disease; and leukemias, such as myeloid, acute lymphoblastic, chronic lymphocytic, acute myloblastic and chronic mylocytic.

The ability of the compounds of the formula (I) or (II) of the invention to inhibit or treat carcinoma can be demonstrated according to the methods referenced below; the determination of in vitro and in vivo anti-cancer activity of several different classes of compounds is described. Mazerska Z., Woynarowska B., Stefanska B., Borowski S., Drugs Exptl. Clin. Res. 13(6): 345–351 (1987). Bissery, M C, Guenard F, Guerritte-Voegelein F, Lavelle F., Cancer Res. 51: 4845–4852 (1991). Rose W., Anti-cancer Drugs 3: 311–321 (1992). Rygaard J, and Povlsen C. O., Acta Pathol. Microbiol. Scand. 77: 758 (1969).

These inhibitors of protein farnesyltransferase are also useful for treating or preventing restenosis in humans and other mammals. The ability of the compounds of the formula (I) or (II) of the invention to prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993).

For use as a lipid lowering or antifungal agent, the total daily dose administered to a host in single or divided doses may be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the formula (I) of the invention can be administered as the sole active pharmaceutical agent for lipid lowering, they can also be used in combination with one or more other cardiovascular agents independently selected from HMG CoA reductase inhibitors, antihyperlipoproteinemic agents and serum cholesterol lowering agents.

Representative HMG CoA reductase inhibitors include lovastatin, pravastatin, velostatin, simvastatin and the like.

Representative antihyperlipoproteinemic agents include probucol and the like.

Representative serum cholesterol lowering agents include Lopid® (gemfibrozil), bile acid sequestrants such as cholestyramine, colestipol, polidexide (DEAE-Sephadex), clofibrate, nicotinic acid and its derivatives, neomycin, p-aminosalicylic acid, bezafibrate and the like.

The above compounds to be employed in combination with the squalene synthase inhibitor of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions which are given at the same time or different times, or the therapeutic agents can be given as a single composition.

While the compounds of the formula (I) or (II) of the invention can be administered as the sole active pharmaceutical agent for the inhibition or treatment of cancer, they can also be used in combination with one or more other chemotherapeutic agents. When administered as a combination, the therapeutic agents can be formulated as separate compositions which are given at the same time or different times, or the therapeutic agents can be given as a single composition.

Representative examples of chemotherapeutic agents are described in Holleb, et al., *Clinical Oncology*, American Cancer Society, United States (1991) p 56 et seq. These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine, vinblastine) and etoposide (VP-16); hormones and hormone antagonists (tamoxifen and corticosteroids); and miscellaneous agents (cisplatin, taxol, brequinar).

The above compounds to be employed in combination with the farnesyl protein transferase inhibitor of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied so as to obtain a desired therapeutic response depending on the route of administration, severity of the disease and the response of the patient.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound of the formula

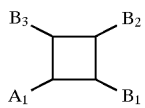

wherein
$A_1$ is —C(O)NR$_1$R$_2$ wherein
 $R_1$ is selected from the group consisting of (i) hydrogen, (ii) loweralkyl, (iii) alkenyl, (iv) alkynyl, (v) aryl, (vi) arylalkyl, and (vii) heterocyclicalkyl, and
 $R_2$ is

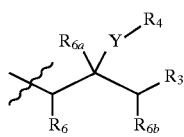

wherein $R_3$ is aryl, aryl substituted with aryl, aryl substituted with heterocyclic or heterocyclic; $R_4$ is aryl, aryl substituted with aryl, aryl substituted with heterocyclic or heterocyclic; $R_6$, $R_{6a}$ and $R_{6b}$ are independently selected from the group consisting of hydrogen and loweralkyl; and Y is a single covalent bond, —CH$_2$—, —CH$_2$CH$_2$—, —CH=CH—, —O—C(O)—, —C(O)—O—, —O—CH$_2$—, —CH$_2$—O—, —S—CH$_2$— or —CH$_2$—S—; and $B_1$, $B_2$ and $B_3$ are independently selected from
(1) hydrogen,
(2) —Q—D
wherein at each occurrence D is independently selected from the group consisting of
 (i) —C(O)R$_{46}$ wherein at each occurrence R$_{46}$ is independently selected from the group consisting of (a) —OR$_{46a}$ wherein at each occurrence R$_{46a}$ is independently selected from the group consisting of hydrogen, a carboxy-protecting group and arylalkyl wherein the alkyl part is substituted with an aryl group, (b) an alpha-amino acid or a beta-amino acid which is bonded via the alpha- or beta-amino group and (c) a di-, tri- or tetrapeptide which is bonded via the amino terminal amino group,
 (ii) —C(O)H,
 (iii) —CH$_2$OH,
 (iv) —C(O)CF$_3$,
 (v) —CH(OH)CF$_3$,
 (vi) —C(OH)(CF$_3$)$_2$,
 (vii) —C(O)NH$_2$,
 (viii) —C(O)NHOH,
 (ix) —CH(=NOH),
 (x) —S(O)$_2$NH$_2$,
 (xi) —NHS(O)$_2$CH$_3$ or —NHS(O)$_2$CF$_3$,
 (xii) 5-tetrazolyl,

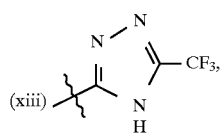
(xiii)

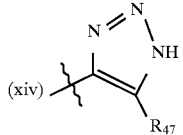
(xiv)

wherein $R_{47}$ is —CN, —NO$_2$, or —CO$_2$R$_{48}$ wherein $R_{48}$ is hydrogen, aryl or loweralkyl,

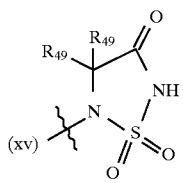
(xv)

wherein at each occurrence $R_{49}$ is independently selected from the group consisting of hydrogen and loweralkyl,

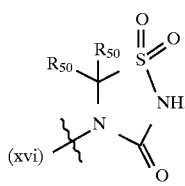
(xvi)

wherein at each occurrence $R_{50}$ is independently selected from the group consisting of hydrogen and loweralkyl,

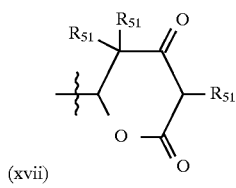
(xvii)

wherein at each occurrence $R_{51}$ is independently selected from the group consisting of hydrogen, loweralkyl, alkenyl, alkoxyalkyl and benzyl,

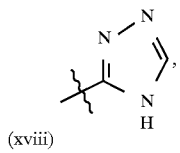
(xviii)

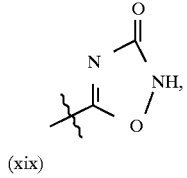
(xix)

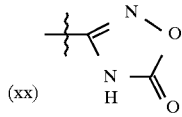
(xx)

-continued

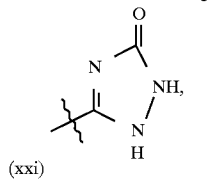
(xxi)

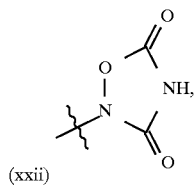
(xxii)

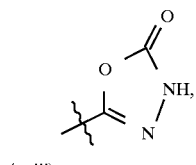
(xxiii)

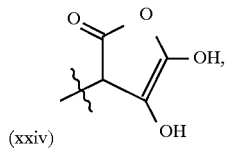
(xxiv)

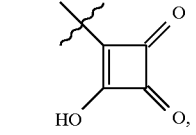
(xxv)

and wherein at each occurrence Q is independently selected from the group consisting of (i) a covalent bond, (ii) —OCH$_2$—, (iii) alkylene, (iv) alkenylene, (v) —C(O)NH, (vi) —NHC(O)NH—, (vii) —CH(OH)— and (viii) —NHC(O)(CH$_2$)$_r$— wherein r is 0 to 4;

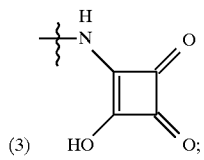
(3)

(4) —CH$_2$—N(OH)—C(O)—R$_{52}$ wherein R$_{52}$ is hydrogen, methyl or trifluoromethyl; and (5) —C(O)—NH—S(O)$_2$—R$_{53}$ wherein R$_{53}$ is aryl, heterocyclic, arylalkyl, (heterocyclic)alkyl, C$_3$–C$_7$-cycloalkyl, C$_1$–C$_8$-alkyl or perfluoro-C$_1$–C$_4$-alkyl;

with the proviso that only one or two of B$_1$, B$_2$ and B$_3$ can be hydrogen;

or a pharmaceutically acceptable salt thereof.

2. A compound as defined by claim 1 wherein

A$_1$ is —C(O)NR$_1$R$_2$ wherein R$_1$ is selected from (i) hydrogen, (ii) loweralkyl, (iii) arylalkyl and (iv) heterocyclicalkyl and R$_2$ is

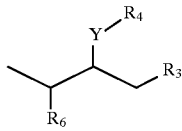

wherein R$_3$ aryl, aryl substituted with aryl, aryl substituted with aryl, aryl substituted with heterocyclic or heterocyclic; R$_4$ is aryl, aryl substituted with aryl, aryl substituted with aryl, aryl substituted with heterocyclic or heterocyclic; R$_6$ is hydrogen or lower alkyl; and Y is a single covalent bond, —CH$_2$—, —CH$_2$CH$_2$—, —CH=CH—, —O—C(O)—, —C(O)—O—, —O—CH$_2$—, —CH$_2$—O—, —S—CH$_2$— or —CH$_2$—S—; and B$_1$, B$_2$ and B$_3$ at each occurrence are independently selected from hydrogen, —CH$_2$OH, and —C(O)—OR$_{46a}$ wherein at each occurrence R$_{46a}$ is independently selected from the group consisting of (i) hydrogen, (ii) arylalkyl wherein the alkyl part is substituted with aryl and (iii) a carboxy protecting group, with the proviso that only one or two of B$_1$, B$_2$ and B$_3$ can be hydrogen; or a pharmaceutically acceptable salt thereof.

3. A compound as defined by claim 1 wherein

A$_1$ is —C(O)NR$_1$R$_2$ wherein R$_1$ is selected from (i) hydrogen, (ii) lower alkyl, and (iii) arylalkyl and R$_2$ is

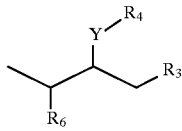

wherein R$_3$ and R$_4$ are independently selected from (i) phenyl, (ii) phenyl substituted with one or two substituents independently selected from loweralkyl, halo, hydroxy, alkoxy, and aryl or heterocyclic wherein the aryl or heterocyclic group is unsubstituted or substituted with one or two substituents independently selected from lower alkyl, halo and alkoxy, (iii) naphthyl and (iv) naphthyl substituted with one or two substituents independently selected from loweralkyl, halo, hydroxy, alkoxy and aryl or heterocyclic wherein the aryl or heterocyclic group is unsubstituted or substituted with one or two substituents independently selected from loweralkyl, halo and alkoxy; R$_6$ is lower alkyl; and Y is a single covalent bond, —CH$_2$—, —CH$_2$CH$_2$—, —CH=CH—, —O—C(O)—, —C(O)—O—, —O—CH$_2$, —CH$_2$—O—, —S—CH$_2$— or —CH$_2$—S—; and B$_1$, B$_2$ and B$_3$ at each occurrence are independently selected from hydrogen, —CH$_2$OH, and —C(O)—OR$_{46a}$ wherein at each occurrence R$_{46a}$ is independently selected from the group consisting of hydrogen and a carboxy protecting group, with the proviso that only one or two of B$_1$, B$_2$ and B$_3$ can be hydrogen;

or a pharmaceutically acceptable salt thereof.

4. A compound as defined by claim 1 wherein

A$_1$ is —C(O)NR$_1$R$_2$ wherein R$_1$ is selected from hydrogen, methyl, benzyl, naphthylmethyl and (heterocyclic)methyl and R$_2$ is

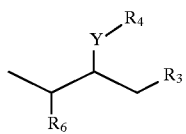

wherein R₃ is phenyl, 3-chlorophenyl, 4-chlorophenyl, 4-fluorophenyl, 4-methylphenyl, 3,4-dichlorophenyl, 4-methoxyphenyl, 3-bromophenyl, 3-biphenylyl, 4-biphenylyl, 4'-chloro-4-biphenylyl, 2-fluoro-4-biphenylyl, 6-fluoro-3-biphenylyl, 3-(2-naphthyl)phenyl, 3-(1-naphthyl)phenyl, 4-(2-naphthyl)phenyl, 1-naphthyl, 2-naphthyl, pyridyl, thienyl, quinolinyl, benzothiophenyl, or 3-(3-thienyl)phenyl; R₄ is 4-biphenylyl, 4-chlorophenyl, 4-methylphenyl, 4-bromophenyl, 4-t-butylphenyl, 4-methoxyphenyl, 3-chlorophenyl, 2-naphthyl, 4'-chloro-4-biphenylyl, 4-(3-thienyl)phenyl, 4-(3-pyridyl)phenyl, 3'-chloro-4-biphenylyl, 3,4-dichlorophenyl, 3,4-difluorophenyl, 3,4-dimethylphenyl, 3-chloro- 4-methylphenyl, 4-chloro-3-methylphenyl, 3,4-dimethoxyphenyl, 3,4,-methylenedioxphenyl, 3-bromophenyl, 4-(2-naphthyl)phenyl, 2-fluoro-4-biphenylyl, 4-(2-furyl)phenyl, 3',4'-methylenedioxy-4-biphenylyl, 2'-fluoro-4-biphenylyl, 2'-methoxy-4-biphenylyl, 4-(5-oxazolyl)phenyl or 2-naphthyl; R₆ is lower alkyl; and Y is a single covalent bond, —CH₂—, —CH₂CH₂—, —CH=CH—, —O—C(O)—, —C(O)—O—, —O—CH₂—, —CH₂—O—, —S—CH₂— or —CH₂—S—; and B₁, B₂ and B₃ at each occurrence are independently selected from hydrogen, —CH₂OH, and —C(O)—OR₄₆ₐ wherein at each occurrence R₄₆ₐ is independently selected from hydrogen and a carboxy protecting group, with the proviso that only one or two of B₁, B₂ and B₃ can be hydrogen;

or a pharmaceutically acceptable salt thereof.

5. A compound as defined by claim 1 wherein A₁ is —C(O)NR₁R₂ wherein R₁ is hydrogen and R₂ is —CH(CH₃)CH(OC(O)-2-naphthyl)(3,4-dichlorobenzyl) or —CH(CH₃)CH(4-biphenylyl)(4-chlorobenzyl); and B₁, B₂ and B₃ at each occurrence are independently selected from hydrogen, —CH₂OH, and —C(O)—OR₄₆ₐ wherein at each occurrence R₄₆ₐ is independently selected from hydrogen and a carboxy protecting group, with the proviso that only one or two of B₁, B₂ and B₃ can be hydrogen;

or a pharmaceutically acceptable salt thereof.

6. A compound selected from the group consisting of:
(1S,2R,3R,4R)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;
(1R,2S,3S,4S)-3-Methoxycarbonyl-4-[N-{(2S,3R)-4-(3,4-dichlorophenyl)-3-(2-naphthoyloxy)-2-butyl}aminocarbonyl]-cyclobutane-1,2-dicarboxylic acid;
(1S,2R,3R,4R)-4-[N-{(2S,3R)-4-(3,4-Dichlorophenyl)-3-(2-naphthoyloxy)-2-butyl}aminocarbonyl]cyclobutane-1,2,3-tricarboxylic acid;
(1R,2S,3S,4S)-4-[N-{(2S,3R)-4-(3,4-Dichlorophenyl)-3-(2-naphthoyloxy)-2-butyl}aminocarbonyl]cyclobutane-1,2,3-tricarboxylic acid;
(1S,2S,3S,4S)-3-Methoxycarbonyl-4-[N-{(2S,3R)-4-(3,4-dichlorophenyl)-3-(2-naphthoyloxy)-2-butyl}aminocarbonyl]cyclobutane-1,2-dicarboxylic acid;
(1α,2α,3β,4β)-4-[N-{(2S,3R)-4-(4-chlorophenyl)-3-(4-biphenylyl)-2-butyl}aminocarbonyl]cyclobutane-1,2,3-tricarboxylic acid;
(1α,2β,3β,4α)-2-Carbomethoxy-4-[N-{(2S,3R)-4-(3,4-dichlorophenyl)-3-(2-naphthoyloxy)-2-butyl}aminocarbonyl]cyclobutane-1,3-dicarboxylic acid;
(1β,2α,3α,4β)-2-Carbomethoxy-4-[N-{(2S,3R)-4-(3,4-dichlorophenyl)-3-(2-naphthoyloxy)-2-butyl}aminocarbonyl]cyclobutane-1,3-dicarboxylic acid;
(1α,2β,3β)-3-[N-{(2S,3R)-4-(3,4-Dichlorophenyl)-3-(2-naphthoyloxy)-2-butyl}aminocarbonyl]cyclobutane-1,2-dicarboxylic acid;
(1α,2β,3β)-3-[N-{2S,3R}-4-(3,4-Dichlorophenyl)-3-(2-naphthoyloxy)-2-butyl}aminocarbonyl]cyclobutane-1,2-dicarboxylic acid;
(1β,2β,3α)-3-[N-{2S,3R}-4-(3,4-Dichlorophenyl)-3-(2-naphthoyloxy)-2-butyl}aminocarbonyl]cyclobutane-1,2-dicarboxylic acid; and
(±)-(1α,2β,4α)-2-[N-{(2S,3R)-4-(4-Chlorophenyl)-3-(4-biphenylyl)-2-butyl}aminocarbonyl]-4-hydroxymethylcyclobutane-1-carboxylic acid or a pharmaceutically acceptable salt thereof.

7. A pharmaceutical composition for inhibiting protein farnesyltransferase comprising a therapeutically effective amount of a compound according to claim 1 and a pharmaceutically acceptable carrier.

8. A pharmaceutical composition for inhibiting squalene synthase comprising a therapeutically effective amount of a compound according to claim 1 and a pharmaceutically acceptable carrier.

9. A method for inhibiting farnesylation of Ras protein in a human or lower mammal in need of such treatment comprising administering a therapeutically effective amount of a compound according to claim 1.

10. A method for inhibiting squalene synthase in a human or lower mammal in need of such treatment comprising administering a therapeutically effective amount of a compound according to claim 1.

11. A method for inhibiting cholesterol biosynthesis in a human or lower mammal in need of such treatment comprising administering a therapeutically effective amount of a compound according to claim 1.

12. A method for inhibiting or treating cancer comprising administering to a mammal in need of such treatment a therapeutically effective amount of a compound as defined by claim 1.

13. A method for inhibiting or treating hyperlipidemia comprising administering to a mammal in need of such treatment a therapeutically effective amount of a compound as defined by claim 1.

14. A method for preventing restenosis comprising administering to a mammal in need of such treatment a therapeutically effective amount of a compound as defined by claim 1.

15. A method for inhibiting or treating cancer comprising administering to a mammal in need of such treatment a therapeutically effective amount of a compound as defined by claim 1 in combination with one or more chemotherapeutic agents.

16. A method for inhibiting or treating atherosclerosis comprising administering to a mammal in need of such treatment a therapeutically effective amount of a compound as defined by claim 1.

17. A method for treating a fungal infection comprising administering to a mammal in need of such treatment a therapeutically effective amount of a compound as defined by claim 1.

18. A method for inhibiting or treating hyperlipidemia comprising administering to a mammal in need of such treatment a therapeutically effective amount of a compound as defined by claim 1 in combination with another cardiovascular agent.

19. A method for inhibiting squalene synthase in a human or lower mammal in need of such treatment comprising administering a therapeutically effective amount of a compound according to claim 6.

20. A method for inhibiting cholesterol biosynthesis in a human or lower mammal in need of such treatment comprising administering a therapeutically effective amount of a compound according to claim 6.

21. A method for inhibiting or treating cancer comprising administering to a mammal in need of such treatment a therapeutically effective amount of a compound as defined by claim 6.

22. A method for preventing restenosis comprising administering to a mammal in need of such treatment a therapeutically effective amount of a compound as defined by claim 6.

23. A compound of the formula

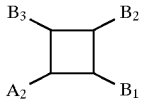

wherein
$A_2$ is
(1) —X—T—G
wherein T is selected from the group consisting of
a) a covalent bond,
b) —C(O)—,
c) —C(S)— and
d) —S(O)$_2$—,
X is selected from the group consisting of
a) a covalent bond,
b) —CH$_2$—,
c) —O—,
d) —S— and
e) —N($R_a$)— wherein $R_a$ is hydrogen, loweralkyl, cycloalkyl, cycloalkylalkyl or arylalkyl,
and G is selected from the group consisting of
a) $R_{42}$,
b) —N($R_{41}$)($R_{42}$)
wherein $R_{41}$ is selected from the group consisting of
(i) —CH($R_d$)C(O)O$R_e$ wherein $R_d$ is selected from the group consisting of loweralkyl, cycloalkyl, cycloalkylalkyl, alkoxyalkyl, thioalkoxyalkyl, hydroxyalkyl, aminoalkyl, carboxyalkyl, alkoxycarbonylalkyl, arylalkyl and alkylsulfonylalkyl and $R_e$ is selected from the group consisting of hydrogen and carboxy-protecting group,
(ii) aryl,
(iii) arylalkyl,
(iv) heterocyclic,
(v) (heterocyclic)alkyl,
(vi) cycloalkylalkyl and
(vii) aryl, heterocyclic, arylalkyl or (heterocyclic)alkyl wherein the aryl group, the aryl part of the arylalkyl group, the heterocyclic group or the heterocyclic part of the (heterocyclic)alkyl group is substituted with one or two substituents —W—$R_{43}$
wherein at each occurrence W is independently selected from the group consisting of
(a) a covalent bond, (b) —C(O)—, (c) —CH$_2$—, (d) —O—, (e) —S(O)$_p$— wherein p is 0, 1 or 2, (f) —N($R_c$)— wherein $R_c$ is hydrogen or loweralkyl, (g) —CH$_2$O—, (h) —CH$_2$S(O)$_p$— wherein p is 0, 1 or 2 and (i) —CH$_2$N($R_c$)— wherein $R_c$ is hydrogen or loweralkyl and
at each occurrence $R_{43}$ is independently selected from the group consisting of
(a) aryl, (b) arylalkyl, (c) cycloalkyl, (d) cycloalkylalkyl, (e) heterocyclic and (f) (heterocyclic)alkyl, and
$R_{42}$ is selected from the group consisting of
(i) aryl,
(ii) arylalkyl,
(iii) alkenyl,
(iv) alkynyl,
(v) arylalkenyl,
(vi) arylalkynyl,
(vii) (heterocyclic)alkyl,
(viii) aryloxyalkyl,
(ix) aryloxyalkenyl,
(x) arylalkoxyalkenyl,
(xi) arylalkyl wherein the alkyl group is substituted with (a) —O$R_{10}$ wherein $R_{10}$ is hydrogen or alkanoyl or (b) —C(O)O$R_h$ wherein $R_h$ is hydrogen or a carboxy-protecting group,
(xii) aroyloxyalkyl, and
(xiii) aryl, arylalkyl or (heterocyclic)alkyl wherein the aryl group, the the aryl part of the arylalkyl group or the heterocyclic part of the (heterocyclic) alkyl group is substituted with one or two substituents —W'—$R_{44}$ wherein at each occurrence W' is independently selected from the group consisting of (a) a covalent bond, (b) —C(O)—, (c) —CH$_2$—, (d) —O—, (e) —S(O)$_m$— wherein m is 0, 1 or 2, (f) —N($R_b$)— wherein $R_b$ is hydrogen or loweralkyl, (g) —CH$_2$O—, (h) —CH$_2$S(O)$_m$— wherein m is 0, 1 or 2 and (i) —CH$_2$N($R_b$)— wherein $R_b$ is hydrogen or loweralkyl and at each occurrence $R_{44}$ is independently selected from the group consisting of (a) aryl, (b) arylalkyl, (c) cycloalkyl, (d) cycloalkylalkyl, (e) heterocyclic and (f) (heterocyclic)alkyl, and
c) —NHR$_{42a}$ or —OR$_{42a}$
wherein $R_{42a}$ is selected from the group consisting of
(i) arylalkyl and
(ii) heterocyclicalkyl,
wherein the alkyl part of the arylalkyl group or the heterocyclicalkyl group is substituted with an arylalkyl group and wherein the aryl part of the arylalkyl group or the heterocyclic part of the heterocyclicalkyl group is substituted with one or two substituents —W"—$R_{45}$ wherein at each occurrence W" is independently selected from the group consisting of (a) a covalent bond, (b) —C(O)—, (c) —CH$_2$—, (d) —O—, (e) —S(O)$_{m'}$— wherein m' is 0, 1 or 2, (f) —N($R_{b'}$)— wherein $R_{b'}$ is hydrogen or loweralkyl, (g) —CH$_2$O—, (h) —CH$_2$S(O)$_{m'}$— wherein m' is 0, 1 or 2 and (i) —CH$_2$N($R_{b'}$)— wherein $R_{b'}$ is hydrogen or loweralkyl and at each occurrence $R_{45}$ is independently selected from the group consisting of (a) aryl, (b) arylalkyl, (c) cycloalkyl, (d) cycloalkylalkyl, (e) heterocyclic and (f) (heterocyclic)alkyl;
(2) —C(O)$R_{42a}$ wherein at each occurrence $R_{42a}$ is independently defined as above;
(3) —CH(OH)$R_{42a}$ wherein at each occurrence $R_{42a}$ is independently defined as above;

(4) —CH=C(R$_{42b}$)(R$_{42c}$) wherein at each occurrence R$_{42b}$ is independently selected from arylalkyl and at each occurrence R$_{42c}$ is independently selected from the group consisting of aryl and heterocyclic wherein the aryl or heterocyclic ring is subsubstituted with —W"—R$_{45}$ wherein at each occurrence W" and R$_{45}$ are independently defined as above; or (5) —C(O)—CH(R$_{42a}$)CH(R$_{42d}$)C(O)OR$_g$ wherein at each occurrence R$_{42a}$ is independently defined as above, at each occurrence R$_{42d}$ is independently selected from aryl and at each occurrence R$_g$ is independently selected from the group consisting of hydrogen and a carboxy-protecting group; and B$_1$, B$_2$ and B$_3$ are independently selected from
(1) hydrogen,
(2) —Q—D wherein at each occurrence D is independently selected from the group consisting of
(i) —C(O)R$_{46}$ wherein at each occurrence R$_{46}$ is independently selected from the group consisting of (a) —OR$_{46a}$ wherein at each occurrence R$_{46a}$ is independently selected from the group consisting of hydrogen, a carboxy-protecting group and arylalkyl wherein the alkyl part is substituted with an aryl group, (b) an alpha-amino acid or a beta-amino acid which is bonded via the alpha- or beta-amino group and (c) a di-, tri- or tetrapeptide which is bonded via the amino terminal amino group,
(ii) —C(O)H,
(iii) —CH$_2$OH,
(iv) —C(O)CF$_3$,
(v) —CH(OH)CF$_3$,
(vi) —C(OH)(CF$_3$)$_2$,
(vii) —C(O)NH$_2$,
(viii) —C(O)NHOH,
(ix) —CH(=NOH),
(X) —S(O)$_2$NH$_2$,
(xi) —NHS(O)$_2$CH$_3$ or —NHS(O)$_2$CF$_3$,
(xii) 5-tetrazolyl,

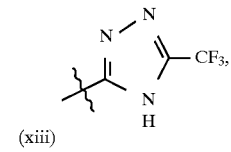
(xiii)

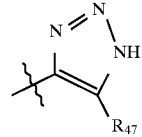
(xiv)

wherein R$_{47}$ is —CN, —NO$_2$, or —CO$_2$R$_{48}$ wherein R$_{48}$ is hydrogen, aryl or loweralkyl,

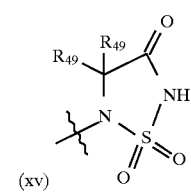
(xv)

wherein at each occurrence R$_{49}$ is independently selected from the group consisting of hydrogen and loweralkyl,

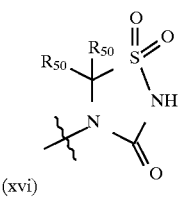
(xvi)

wherein at each occurrence R$_{50}$ is independently selected from the group consisting of hydrogen and loweralkyl,

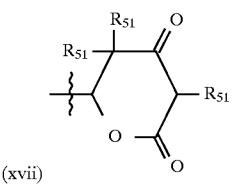
(xvii)

wherein at each occurrence R$_{51}$ is independently selected from the group consisting of hydrogen, loweralkyl, alkenyl, alkoxyalkyl and benzyl,

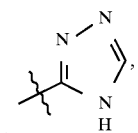
(xviii)

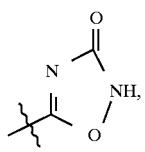
(xix)

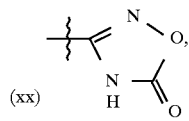
(xx)

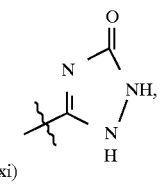
(xxi)

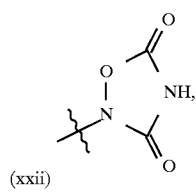
(xxii)

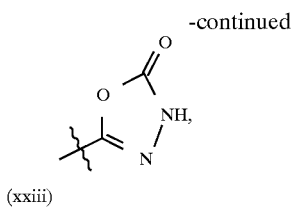

(xxiii)

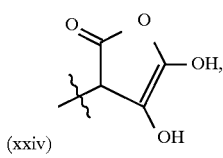

(xxiv)

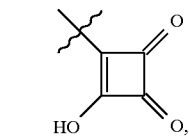

(xxv)

and wherein at each occurrence Q is independently selected from the group consisting of (i) a covalent bond, (ii) —OCH₂—, (iii) alkylene, (iv) alkenylene, (v) —C(O)NH, (vi) —NHC(O)NH—, (vii) —CH(OH)— and (viii) —NHC(O)(CH₂)ᵣ— wherein r is 0 to 4;

(3)

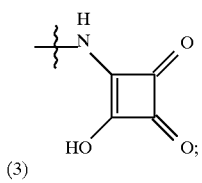

(3)

(4) —CH₂—N(OH)—C(O)—R₅₂ wherein R₅₂ is hydrogen, methyl or trifluoromethyl; and (5) —C(O)—NH—S(O)₂—R₅₃ wherein R₅₃ is aryl, heterocyclic, arylalkyl, (heterocyclic)alkyl, C₃-C₇-cycloalkyl, C₁-C₈-alkyl or perfluoro-C₁-C₄-alkyl;

with the proviso that only one or two of B₁, B₂ and B₃ can be hydrogen;

or a pharmaceutically acceptable salt thereof.

24. A compound as defined by claim 1 wherein
A₂ is —C(O)NR₄₁R₄₂, —N(Rₐ)—C(O)NR₄₁R₄₂ wherein Rₐ is hydrogen, loweralkyl, cycloalkyl, cycloalkylalkyl or arylalkyl, —O—C(O)NR₄₁R₄₂ or —CH₂—C(O)NR₄₁R₄₂ wherein R₄₁ is selected from the group consisting of
(i) aryl, (ii) arylalkyl, (iii) heterocyclic, and (iv) (heterocyclic)alkyl, and R₄₂ is selected from (i) aryl, (ii) arylalkyl, (iii) alkenyl, (iv) alkynyl, (v) arylalkenyl, (vi) arylalkynyl, (vii) (heterocyclic)alkyl, (viii) aryloxyalkyl, (ix) aryloxyalkenyl, (x) arylalkoxyalkenyl, (xi) arylalkyl wherein the alkyl group is substituted with —OR₁₀ wherein R₁₀ is hydrogen or alkanoyl, and (xii) aryl, arylalkyl or (heterocyclic)alkyl wherein the aryl group, the aryl part of the arylalkyl group or the heterocyclic part of the (heterocyclic)alkyl group is substituted with —W'—R₄₄ wherein W' is selected from the group consisting of (a) a covalent bond, (b) —C(O)—, (c) —CH₂—, (d) —O—, (e) —S(O)ₚ— wherein p is 0, 1 or 2, (f) —N(Rᵦ)— wherein Rᵦ is hydrogen or loweralkyl, (g) —CH₂O—, (h) —CH₂S(O)ₘ— wherein m is 0, 1 or 2 and (i) —CH₂N(Rᵦ)— wherein Rᵦ is hydrogen or loweralkyl and R₄₄ is selected from the group consisting of (a) aryl, (b) arylalkyl, (c) cycloalkyl, (d) cycloalkylalkyl, (e) heterocyclic and (f) (heterocyclic)alkyl;

and B₁, B₂ and B₃ at each occurrence are independently —C(O)—OR₄₆ₐ wherein at each occurrence R₄₆ₐ is independently selected from the group consisting of (i) hydrogen, (ii) arylalkyl wherein the alkyl part is substituted with aryl and (iii) a carboxy protecting group;

or a pharmaceutically acceptable salt thereof.

25. A compound as defined by claim 1 wherein
A₂ is —C(O)NR₄₁R₄₂ wherein R₄₁ is (i) arylalkyl or (ii) (heterocyclic)alkyl and R₄₂ is selected from the group consisting of (i) arylalkyl, (ii) arylalkenyl, (iii) aryloxyalkyl, (iv) aryloxyalkenyl, (v) arylalkoxyalkenyl, (vi) arylalkyl wherein the alkyl group is substituted with —OR₁₀ wherein R₁₀ is hydrogen or alkanoyl, and (vii) aryl, arylalkyl or (heterocyclic)alkyl wherein the aryl group, the the aryl part of the arylalkyl group or the heterocyclic part of the (heterocyclic)alkyl group is substituted with —W'-R₄₄ wherein W' is selected from the group consisting of (a) a covalent bond, (b) —CH₂—, and (c) —O— and R₄₄ is selected from (a) aryl, (b) arylalkyl, (c) heterocyclic and (d) (heterocyclic)alkyl; and B₁, B₂ and B₃ at each occurrence are independently —C(O)—OR₄₆ₐ wherein at each occurrence R₄₆ₐ is independently selected from the group consisting of hydrogen and a carboxy protecting group;

or a pharmaceutically acceptable salt thereof.

26. A compound as defined by claim 1 wherein
A₂ is —C(O)NR₄₁R₄₂ wherein R₄₁ is benzyl or (heterocyclic)methyl and R₄₂ is selected from the group consisting of 4-(phenoxy)benzyl, (4-hydroxy-5-methyl)-6-phenylhexyl, 4-acetoxy-5-methyl-6-phenylhexyl, 5-phenyl-2,4-pentadienyl, and 3-phenyl-2-propenyl; and B₁, B₂ and B₃ at each occurrence are independently —C(O)—OR₄₆ₐ wherein at each occurrence R₄₆ₐ is independently selected from the group consisting of hydrogen and a carboxy protecting group;

or a pharmaceutically acceptable salt thereof.

27. A compound as defined by claim 1 wherein
A₂ is —C(O)NR₄₁R₄₂ wherein R₄₁ is benzyl or (heterocyclic)methyl and R₄₂ is selected from the group consisting of 3-chloro-4-(phenoxy)benzyl, 4-(phenoxy)benzyl, (4-hydroxy-5-methyl)-6-phenylhexyl, 4-acetoxy-5-methyl-6-phenylhexyl, 5-phenyl-2,4-pentadienyl, and 3-phenyl-2-propenyl; and B₁, B₂ and B₃ at each occurrence are independently —C(O)—OR₄₆ₐ wherein at each occurrence R₄₆ₐ is independently selected from the group consisting of hydrogen and a carboxy protecting group;

or a pharmaceutically acceptable salt thereof.

28. A compound selected from the group consisting of:
(1α,2β,3β,4α)-1-[N-Benzyl-N-{(4S*,5S*)-(4-hydroxy-5-methyl)-6-phenylhexyl}aminocarbonyl]cyclobutane-2,3,4-tricarboxylic acid;

(1α,2β,3β,4α)-1-[N-Benzyl-N-(4-phenoxybenzyl)aminocarbonyl]-cyclobutane-2,3,4-tricarboxylic acid;

(1α,2β,3β,4α)-1-[N-(Thien-2-ylmethyl)-N-(4-phenoxybenzyl)-aminocarbonyl]cyclobutane-2,3,4-tricarboxylic acid;

(1α,2β,3β,4α)-1-[N-Benzyl-N-(4-phenoxybenzyl)aminocarbonyl]-3-(methyloxycarbonyl)cyclobutane-2,4-dicarboxylic acid;

(1α,2β,3β,4α)-1-[N-Benzyl-N-(4-phenoxybenzyl)
aminocarbonyl]-4-(methyloxycarbonyl)cyclobutane-2,3-
dicarboxylic acid;
(1α,2β,3β,4α)-1-[N-Benzyl-N-(trans-3-phenyl-2-propenyl)
-aminocarbonyl]cyclobutane-2,3,4-tricarboxylic acid;
(−)-(1α,2β,3β,4α)-1-[N-Benzyl-N-(4-phenoxybenzyl)
aminocarbonyl]-cyclobutane-2,3,4-tricarboxylic acid;
(+)-(1α,2β,3β,4α)-1-8 N-Benzyl-N-(4-phenoxybenzyl)
aminocarbonyl]-cyclobutane-2,3,4-tricarboxylic acid;
and
(1α,2β,3β,4α)-4-[N-Benzyl-N-(3-chloro-4-(phenoxy)
benzyl)aminocarbonyl]-cyclobutane-1,2,3-tricarboxylic
acid
or a pharmaceutically acceptable salt thereof.

29. A pharmaceutical composition for inhibiting protein farnesyltransferase comprising a therapeutically effective amount of a compound according to claim 23 and a pharmaceutically acceptable carrier.

30. A method for inhibiting farnesylation of Ras protein in a human or lower mammal in need of such treatment comprising administering a therapeutically effective amount of a compound according to claim 23.

31. A method for inhibiting or treating cancer comprising administering to a mammal in need of such treatment a therapeutically effective amount of a compound as defined by claim 23.

32. A method for preventing restenosis comprising administering to a mammal in need of such treatment a therapeutically effective amount of a compound as defined by claim 23.

33. A method for inhibiting or treating cancer comprising administering to a mammal in need of such treatment a therapeutically effective amount of a compound as defined by claim 23 in combination with one or more chemotherapeutic agents.

34. A method for inhibiting or treating cancer comprising administering to a mammal in need of such treatment a therapeutically effective amount of a compound as defined by claim 28.

35. A method for preventing restenosis comprising administering to a mammal in need of such treatment a therapeutically effective amount of a compound as defined by claim 28.

* * * * *

UNITED STATES PATENT AND TRADEMARK OFFICE
CERTIFICATE OF CORRECTION

PATENT NO. : 5,831,115
DATED : November 3, 1998
INVENTOR(S) : Arendsen et al.

It is certified that error appears in the above-identified patent and that said Letters Patent is hereby corrected as shown below:

Column 87, line 8, change "1-8 N" to --1-[N--.

Signed and Sealed this

Fourth Day of May, 1999

Attest:

Q. TODD DICKINSON

Attesting Officer

Acting Commissioner of Patents and Trademarks